(12) United States Patent
Seki

(10) Patent No.: US 8,530,506 B2
(45) Date of Patent: Sep. 10, 2013

(54) PROCESS FOR PRODUCTION OF BIPHENYL DERIVATIVE

(75) Inventor: Masahiko Seki, Osaka (JP)

(73) Assignee: Mitsubishi Tanabe Pharma Corporation, Osaka-shi (JP)

( * ) Notice: Subject to any disclaimer, the term of this patent is extended or adjusted under 35 U.S.C. 154(b) by 0 days.

(21) Appl. No.: 13/509,817

(22) PCT Filed: Sep. 24, 2010

(86) PCT No.: PCT/JP2010/066596
§ 371 (c)(1),
(2), (4) Date: May 31, 2012

(87) PCT Pub. No.: WO2011/061996
PCT Pub. Date: May 26, 2011

(65) Prior Publication Data
US 2012/0232283 A1    Sep. 13, 2012

(30) Foreign Application Priority Data

Nov. 17, 2009  (JP) ................................ 2009-262149
Jun. 24, 2010  (JP) ................................ 2010-143845

(51) Int. Cl.
*A61K 31/41*      (2006.01)
*C07D 249/00*    (2006.01)

(52) U.S. Cl.
USPC ......................................... 514/381; 548/250

(58) Field of Classification Search
USPC ......................................... 514/381; 548/250
See application file for complete search history.

(56) References Cited

U.S. PATENT DOCUMENTS

| 5,334,718 A | 8/1994 | Thomas et al. |
| 2007/0043098 A1 | 2/2007 | Sedelmeier |
| 2011/0184187 A1 | 7/2011 | Sedelmeier |

FOREIGN PATENT DOCUMENTS

| JP | 5-286972 | * 11/1993 |
| JP | 05-286972 A | 11/1993 |
| JP | 2009-513555 A | 4/2009 |
| WO | 2004/101534 A1 | 11/2004 |
| WO | 2006/038223 A1 | 4/2006 |

OTHER PUBLICATIONS

Ackermann et al., *Angew. Chem. Int. Ed.*, 48: 9792-9827 (2009).
Bernhart et al., *J. Med. Chem.*, 36: 3371-3380 (1993).
Beutler et al., *Organic Process Research & Development*, 11: 892-898 (2007).
Cousaert et al., *Tetrahedron Letters*, 46: 6529-6532 (2005).
Cousaert et al., *Tetrahedron Letters*, 49: 2743-2747 (2008).
Larsen et al., *J. Org. Chem.*, 59: 6391-6394 (1994).
Oi et al., *Tetrahedron*, 64: 6051-6059 (2008).
Oi et al, *Chemistry Letters*, 37(9): 994-995 (2008).
Japanese Patent Office, International Search Report in International Patent Application No. PCT/JP2010/066596 (Nov. 9, 2010).
International Bureau of WIPO, International Preliminary Report on Patentability in International Patent Application No. PCT/JP2010/066596 (Oct. 26, 2011).
Kavitha et al., *Bioorganic & Medicinal Chemistry*, 15: 7391-7398 (2007).
European Patent Office, Extended European Search Report in European Patent Application No. 10831396.8 (May 24, 2013).

* cited by examiner

*Primary Examiner* — Susannah Chung
(74) *Attorney, Agent, or Firm* — Leydig, Voit & Mayer, Ltd.

(57) ABSTRACT

The invention provides a production method of a biaryltetrazole derivative useful as an intermediate for an angiotensin II receptor antagonist.
The method comprises
reacting an aryltetrazole derivative with a benzene derivative,
deprotecting or reducing the resulting compound
and
halogenating the deprotected or reduced compound.

5 Claims, No Drawings

PROCESS FOR PRODUCTION OF BIPHENYL DERIVATIVE

CROSS-REFERENCE TO RELATED APPLICATIONS

This patent application is the U.S. national phase of International Patent Application PCT/JP2010/066596, filed Sep. 24, 2012, which claims the benefit of Japanese Patent Application Nos. 2010-143845, filed Jun. 24, 2012, and 2009-262149, filed Nov. 17, 2009.

TECHNICAL FIELD

The present invention relates to a production method of biaryltetrazole derivative or a salt thereof, which is useful as an intermediate for an angiotensin II receptor antagonist.

BACKGROUND ART

Losartan potassium, valsartan, olmesartan medoxomil, candesartan cilexetil, telmisartan, irbesartan and the like are useful as an angiotensin II receptor antagonist. As the production methods of these compounds, the production method described in J. Org. Chem., 1994, vol. 59, pages 6391-6394 (non-patent document 1) as a synthetic method of losartan, the production method described in Org. Process Res. Dev., 2007, vol. 11, pages 892-898 (non-patent document 2) as a synthetic method of valsartan, and the production method described in J. Med. Chem., 1993, vol. 36, pages 3371-3380 (non-patent document 3) as a synthetic method of irbesartan have been known.

In addition, as a conventional method for a biphenylation reaction, the method described in Chem. Lett., 2008, vol. 37, No. 9, pages 994-995 (non-patent document 4), the method described in Tetrahedron, 2008, vol. 64, pages 6051-6059 (non-patent document 5), and the method described in Angewandte Chemie International Edition, 2009, vol. 48, pages 9792-9827 (non-patent document 6) have been known.

DOCUMENT LIST

Non-patent Document

Non-patent document 1 J. Org. Chem., 1994, vol. 59, pages 6391-6394
Non-patent document 2 Org. Process Res. Dev., 2007, vol. 11, pages 892-898
Non-patent document 3 J. Med. Chem., 1993, vol. 36, pages 3371-3380
Non-patent document 4 Chem. Lett., 2008, vol. 37, No. 9, pages 994-995
Non-patent document 5 Tetrahedron, 2008, vol. 64, pages 6051-6059
Non-patent document 6 Angewandte Chemie International Edition, 2009, vol. 48, pages 9792-9827

SUMMARY OF THE INVENTION

Problems to be Solved by the Invention

Since the production methods described in the aforementioned documents require an expensive metal compound, the development of a more economical production method has been desired.

An object of the present invention is to provide a novel production method which can produce, under economical conditions suitable for industrial production, a biaryltetrazole derivative useful as an intermediate for an angiotensin II receptor antagonist, and permits use of an economical metal compound.

Means of Solving the Problems

The present inventors have conducted intensive studies in an attempt to solve the aforementioned problems and found that the following production method can produce, under economical conditions suitable for industrial production, a biaryltetrazole derivative useful as an intermediate for an angiotensin II receptor antagonist, and permits use of an economical metal compound, which resulted in the completion of the present invention.

Accordingly, the present invention relates to;

(1) A production method (hereinafter sometimes to be referred to as "Production Method 1") of a biaryltetrazole derivative represented by the formula [I]:

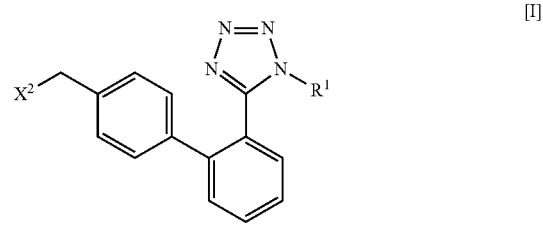

wherein $X^2$ is a halogen atom, and $R^1$ is a tetrazolyl-protecting group (hereinafter sometimes to be referred to as biaryltetrazole derivative [I]) or a salt thereof, which comprises 1) reacting an aryltetrazole derivative represented by the formula [II]:

wherein $R^1$ is as defined above (hereinafter sometimes to be referred to as aryltetrazole derivative [II]) with a benzene derivative represented by the formula [III]:

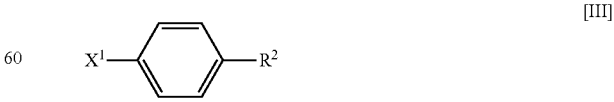

wherein $R^2$ is a methyl group, a methyl group substituted by hydroxyl group(s) protected by a protecting group, or a lower alkoxycarbonyl group, and $X^1$ is a leaving group (hereinafter sometimes to be referred to as benzene derivative [III]);

2) in the obtained compound represented by the formula [IV]:

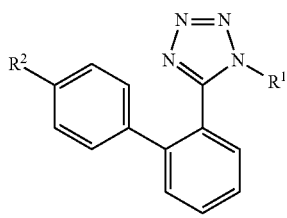
[IV]

wherein the symbols are as defined above (hereinafter sometimes to be referred to as compound [IV]),
(a) deprotecting the compound wherein $R^2$ is a methyl group substituted by hydroxyl group(s) protected by a protecting group, or
(b) reducing the compound wherein $R^2$ is a lower alkoxycarbonyl group,
to give a compound represented by the formula [V]:

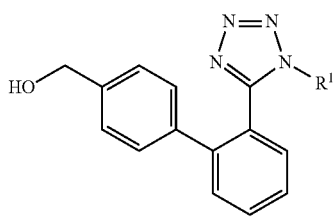
[V]

wherein the symbol is as defined above (hereinafter sometimes to be referred to as compound [V]); and
3) halogenating
the compound represented by the formula [IV] wherein $R^2$ is a methyl group, or
the compound represented by the formula [V] when $R^2$ in the compound represented by the formula [IV] is a methyl group substituted by hydroxyl group(s) protected by a protecting group, or a lower alkoxycarbonyl group;
(2) the production method of the above-mentioned (1), wherein the aryltetrazole derivative represented by the formula [II] is reacted with the benzene derivative represented by the formula [III] in the presence of a metal catalyst;
(3) the production method of the above-mentioned (1), wherein the aryltetrazole derivative represented by the formula [II] is reacted with the benzene derivative represented by the formula [III] in the presence of a base and a metal catalyst;
(4) A production method (hereinafter sometimes to be referred to as "Production Method 2") of a compound represented by the formula [IX]:

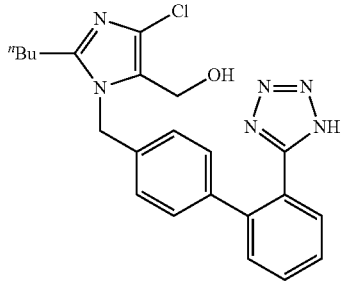
[IX]

(i.e., losartan, hereinafter sometimes to be referred to as compound [IX]) or a salt thereof, which comprises
1) reacting a biaryltetrazole derivative represented by the formula [I]:

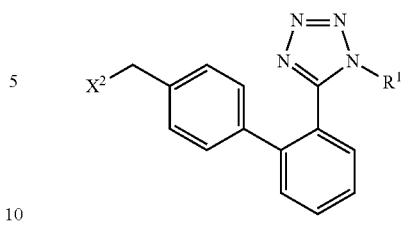
[I]

wherein $X^2$ is a halogen atom, and $R^1$ is a tetrazolyl-protecting group, or a salt thereof, which is obtained by the production method of the above-mentioned (1), with a compound represented by the formula [VI]:

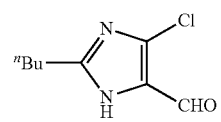
[VI]

(hereinafter sometimes to be referred to as compound [VI]); and
2-A) reducing the obtained compound represented by the formula [VII]:

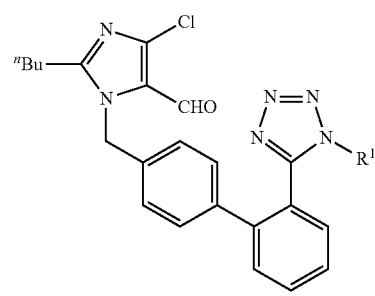
[VII]

wherein the symbol is as defined above (hereinafter sometimes to be referred to as compound [VII]) to give a compound represented by the formula [VIII]:

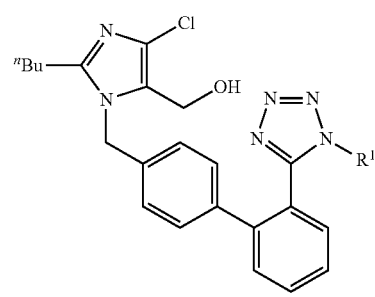
[VIII]

wherein the symbol is as defined above (hereinafter sometimes to be referred to as compound [VIII]), and
removing $R^1$ from the compound represented by the formula [VIII]; or
2-B) removing $R^1$ from the compound represented by the formula [VII] to give a compound represented by the formula [VIII-2]:

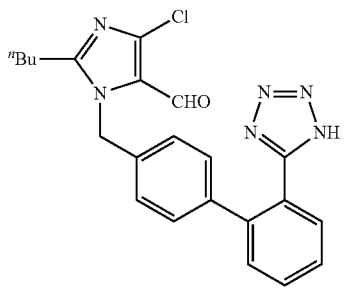

[VIII-2]

(hereinafter sometimes to be referred to as compound [VIII-2]), and
reducing the compound represented by the formula [VIII-2];
(5) A production method (hereinafter sometimes to be referred to as "Production Method 3") of a compound represented by the formula [XV]:

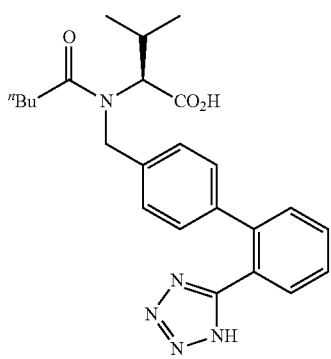

[XV]

(i.e., valsartan, hereinafter sometimes to be referred to as compound [XV]) or a salt thereof, which comprises
1) reacting a biaryltetrazole derivative represented by the formula [I]:

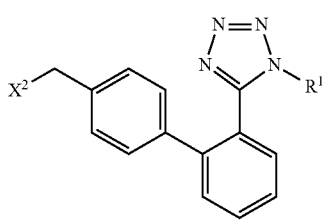

[I]

wherein $X^2$ is a halogen atom, and $R^1$ is a tetrazolyl-protecting group, or a salt thereof, which is obtained by the production method of the above-mentioned (1), with a compound represented by the formula [X]:

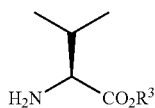

[X]

wherein $R^3$ is a carboxy-protecting group (hereinafter sometimes to be referred to as compound [X]) or a salt thereof;

2-A) removing $R^1$ from the obtained compound represented by the formula [XI]:

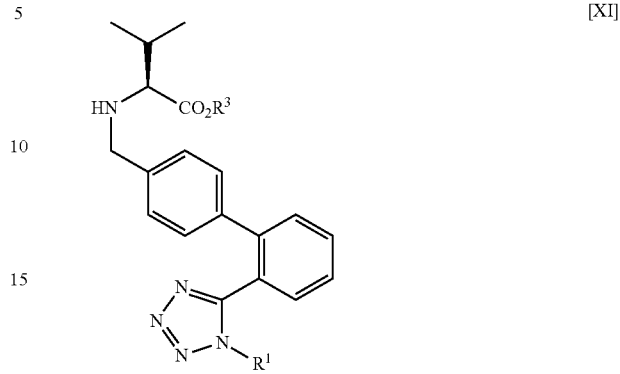

[XI]

wherein the symbols are as defined above (hereinafter sometimes to be referred to as compound [XI]),
reacting the obtained compound represented by the formula [XII]:

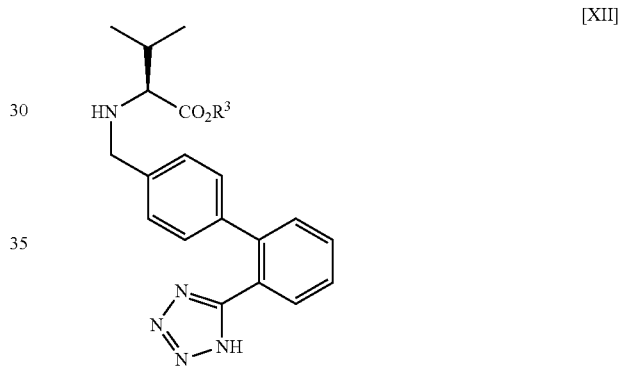

[XII]

wherein the symbol is as defined above (hereinafter sometimes to be referred to as compound [XII]) with a compound represented by the formula [XIII]:

$CH_3CH_2CH_2CH_2CO$—$X^3$ wherein $X^3$ is a leaving group (hereinafter sometimes to be referred to as compound [XIII]), and
removing $R^3$ from the obtained compound represented by the formula [XIV]:

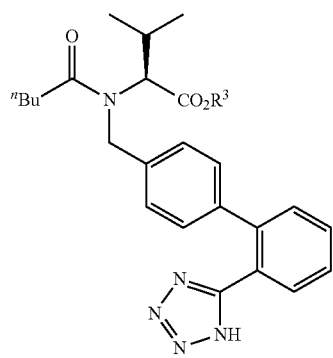

[XIV]

wherein the symbol is as defined above (hereinafter sometimes to be referred to as compound [XIV]); or 2-B) reacting the compound represented by the formula [XI] with the compound represented by the formula [XIII], and removing R¹ and R³ from the obtained compound represented by the formula [XII-2]:

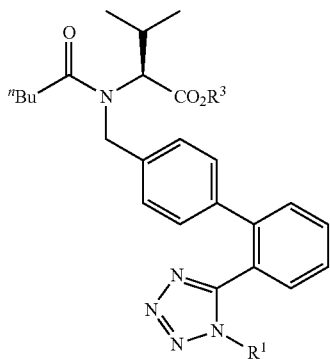

[XII-2]

wherein the symbols are as defined above (hereinafter sometimes to be referred to as compound [XII-2]);

(6) A production method (hereinafter sometimes to be referred to as "Production Method 4") of a compound represented by the formula [XVIII]:

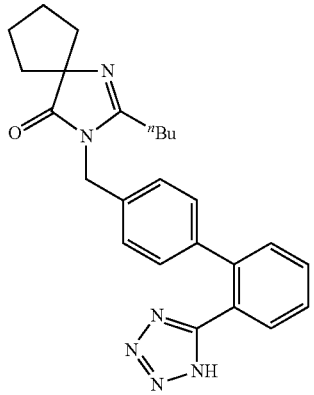

[XVIII]

(i.e., irbesartan, hereinafter sometimes to be referred to as compound [XVIII]) or a salt thereof, which comprises reacting a biaryltetrazole derivative represented by the formula [I]:

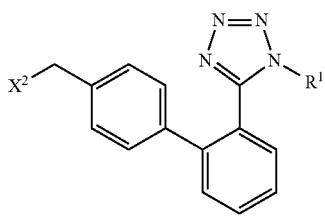

[I]

wherein X² is a halogen atom, and R¹ is a tetrazolyl-protecting group, or a salt thereof, which is obtained by the production method of the above-mentioned (1), with a compound represented by the formula [XVI]:

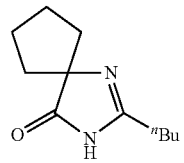

[XVI]

(hereinafter sometimes to be referred to as compound [XVI]) or a salt thereof to give a compound represented by the formula [XVII]:

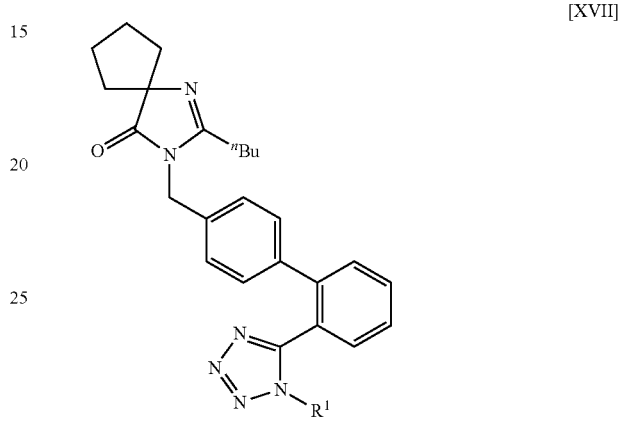

[XVII]

wherein the symbol is as defined above (hereinafter sometimes to be referred to as compound [XVII]), and removing R¹ from the compound represented by the formula [XVII]; and (7) A production method (hereinafter sometimes to be referred to as "Production Method 5") of a compound represented by the formula [XXVII]:

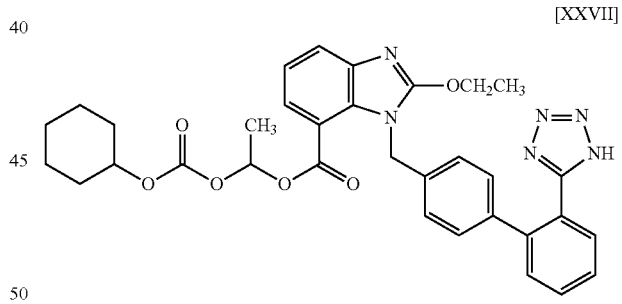

[XXVII]

i.e., candesartan cilexetil, hereinafter sometimes to be referred to as compound [XXVII]) or a salt thereof, which comprises 1) reacting a biaryltetrazole derivative represented by the formula [I]:

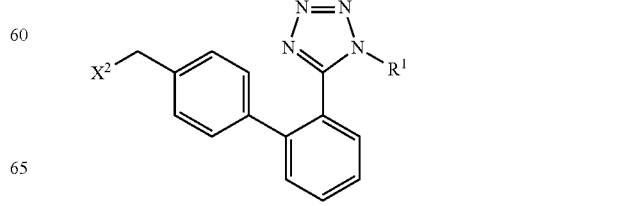

[I]

wherein $X^2$ is a halogen atom, and $R^1$ is a tetrazolyl-protecting group, or a salt thereof, which is obtained by the production method of the above-mentioned (1), with a compound represented by the formula [XIX]:

[XIX]

wherein $R^4$ is a carboxy-protecting group, and $R^5$ is an amino-protecting group (hereinafter sometimes to be referred to as compound [XIX]), 2) removing $R^5$ from the obtained compound represented by the formula [XX]:

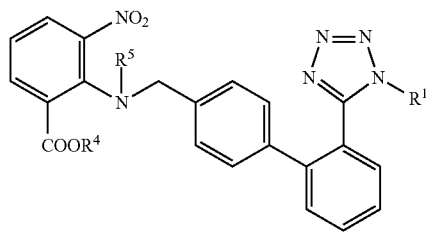
[XX]

wherein the symbols are as defined above (hereinafter sometimes to be referred to as compound [XX]) to give a compound represented by the formula [XXI]:

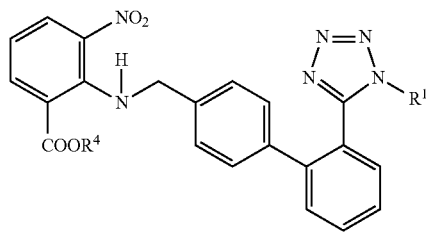
[XXI]

wherein the symbols are as defined above (hereinafter sometimes to be referred to as compound [XXI]), and
reducing the compound represented by the formula [XXI], 3) reacting the obtained compound represented by the formula [XXII]:

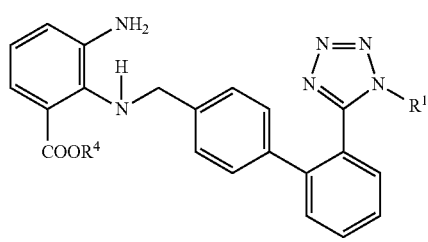
[XXII]

wherein the symbols are as defined above (hereinafter sometimes to be referred to as compound [XXII]) with tetraethoxymethane to give a compound represented by the formula [XXIII]:

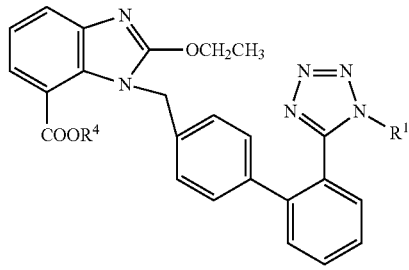
[XXIII]

wherein the symbols are as defined above (hereinafter sometimes to be referred to as compound [XXIII]), and
removing $R^4$ from the compound represented by the formula [XXIII], and 4) reacting the obtained compound represented by the formula [XXIV]:

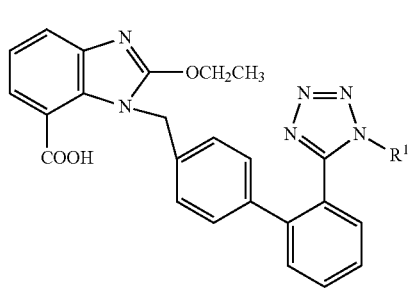
[XXIV]

wherein the symbol is as defined above (hereinafter sometimes to be referred to as compound [XXIV]) with a compound represented by the formula [XXV]:

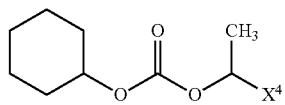
[XXV]

wherein $X^4$ is a leaving group or a hydroxyl group (hereinafter sometimes to be referred to as compound [XXV]) to give a compound represented by the formula [XXVI]:

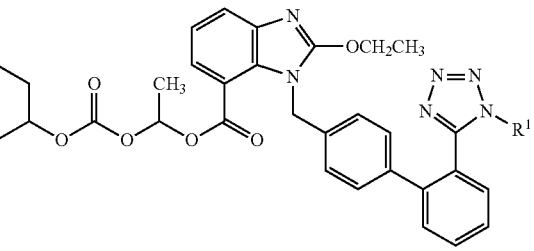
[XXVI]

wherein the symbol is as defined above (hereinafter sometimes to be referred to as compound [XXVI]), and removing $R^1$ from the compound represented by the formula [XXVI].

Effect of the Invention

According to the present invention, an economical metal compound can be used and a biaryltetrazole derivative useful to as an intermediate for an angiotensin II receptor antagonist can be produced under economical conditions suitable for industrial production.

DESCRIPTION OF EMBODIMENTS

The definitions of the symbol and term used in the present invention are explained in detail below.

The "tetrazolyl-protecting group" is not particularly limited as long as it can stably protect a tetrazolyl group during the reaction, and specific examples thereof include those described in Protective Groups in Organic Synthesis $3^{rd}$ Ed., T. W. Greene, P. G. M. Wuts, John Wiley and Sons, Inc., 1999.

Examples of the tetrazolyl-protecting group include a $C_{7-19}$ aralkyl group (e.g., benzyl, diphenylmethyl, trityl etc.); a substituted $C_{7-19}$ aralkyl group such as substituted benzyl, substituted diphenylmethyl and the like (preferably $C_{7-19}$ aralkyl substituted by 1 to 3 substituents selected from the group consisting of $C_{1-6}$ alkyl, nitro, $C_{1-6}$ alkylenedioxy and $C_{1-6}$ alkoxy (when two or more substituents are presented, they may be the same or different, and they may be bonded to each other to form a ring), e.g., p-methylbenzyl, p-nitrobenzyl, 2,4-dimethoxybenzyl, 3,4-dimethoxybenzyl, 3,4-(methylenedioxy)benzyl, p-methoxybenzyl, o-methoxybenzyl, 3,4,5-trimethoxybenzyl etc.);
a substituted $C_{1-6}$ alkyl group (preferably $O_{1-6}$ alkyl substituted by 1 to 3 substituents selected from the group consisting of hydroxy, alkoxy (e.g., $C_{1-6}$ alkoxy), aryloxy (e.g., $C_{6-10}$ aryloxy) and dialkylamino (e.g., di($C_{1-6}$ alkyl)amino), e.g., hydroxymethyl, alkoxymethyl, aryloxymethyl, dialkylaminomethyl etc.);
a trialkylsilyl group (preferably tri($C_{1-6}$ alkyl)silyl); a $C_{1-6}$ alkyl group (e.g., t-butyl etc.)
and the like.

The "protecting group" of the "methyl group substituted by hydroxyl group(s) protected by a protecting group" is not particularly limited as long as it can stably protect a hydroxyl group during the reaction, and specific examples thereof include those described in Protective Groups in Organic Synthesis $3^{rd}$ Ed., T. W. Greene, P. G. M. Wuts, John Wiley and Sons, Inc., 1999.

Examples of the protecting group include an acyl group (preferably $O_{1-6}$ alkyl-carbonyl, $C_{3-8}$ cycloalkyl-carbonyl, $C_{6-10}$ aryl-carbonyl, e.g., acetyl, propionyl, butyryl, isobutyryl, pivaloyl, cyclohexylcarbonyl, benzoyl etc.), a $C_{7-19}$ aralkyl group (e.g., benzyl etc.), a trialkylsilyl group (preferably tri($C_{1-6}$ alkyl)silyl, e.g., trimethylsilyl, triethylsilyl, triisopropylsilyl, t-butyldimethylsilyl etc.),
an alkoxycarbonyl group (preferably $C_{1-6}$ alkoxy-carbonyl) and the like.

The "carboxy-protecting group" is not particularly limited as long as it can stably protect a carboxy group during the reaction, and specific examples thereof include those described in Protective Groups in Organic Synthesis $3^{rd}$ Ed., T. W. Greene, P. G. M. Wuts, John Wiley and Sons, Inc., 1999.

Examples of the carboxy-protecting group include an alkyl group (preferably $C_{1-8}$ alkyl, e.g., methyl, ethyl, propyl, isopropyl, butyl, pentyl, hexyl),
a $C_{3-8}$ cycloalkyl group (e.g., cyclohexyl),
a $C_{7-19}$ aralkyl group (e.g., benzyl, diphenylmethyl, trityl),
a $C_{2-6}$ alkenyl group (e.g., allyl)
and the like.

The "amino-protecting group" is not particularly limited as long as it can stably protect an amino group during the reaction, and specific examples thereof include those described in Protective Groups in Organic Synthesis $3^{rd}$ Ed., T. W. Greene, P. G. M. Wuts, John Wiley and Sons, Inc., 1999.

Examples of the amino-protecting group include an acyl group (preferably $C_{1-6}$ alkyl-carbonyl, $C_{3-8}$ cycloalkyl-carbonyl, $C_{6-10}$ aryl-carbonyl, e.g., acetyl, propionyl, butyryl, isobutyryl, pivaloyl, cyclohexylcarbonyl, benzoyl etc.), a lower alkoxycarbonyl group and the like.

Examples of the "lower alkoxycarbonyl group" include a linear or branched chain $C_{1-12}$ alkoxy-carbonyl group. Among them, methoxycarbonyl, ethoxycarbonyl, butoxycarbonyl (e.g., tert-butoxycarbonyl) and the like are preferable.

Examples of the "leaving group" for X' include
a halogen atom,
a $C_{6-10}$ arylsulfonyloxy group optionally substituted by 1 to 3 $C_{1-6}$ alkyl groups (e.g., toluenesulfonyloxy etc.),
a $C_{1-6}$ alkylsulfonyloxy group optionally substituted by 1 to 3 halogen atoms (e.g., methanesulfonyloxy, trifluoromethanesulfonyloxy etc.)
and the like.

Examples of the "leaving group" for $X^3$ or $X^4$ include
a halogen atom,
a $C_{6-10}$ arylsulfonyloxy group optionally substituted by 1 to 3 $C_{1-6}$ alkyl groups (e.g., toluenesulfonyloxy etc.),
a $C_{1-6}$ alkylsulfonyloxy group optionally substituted by 1 to 3 halogen atoms (e.g., methanesulfonyloxy etc.),
an alkanoyloxy group (preferably $C_{1-6}$ alkyl-carbonyloxy),
an aroyloxy group (preferably $C_{6-10}$ aryl-carbonyloxy),
a dialkoxyphosphoryloxy group (preferably di ($C_{1-6}$ alkoxy) phosphoryloxy),
a diaryloxyphosphoryloxy group (preferably di($C_{6-10}$ aryloxy)phosphoryloxy)
and the like.

Examples of the "halogen atom" include fluorine, chlorine, bromine and iodine.

Next, the production method of the present invention is explained.
[Production Method 1]

Aryltetrazole derivative [II] and benzene derivative [III] may be commercially available products, or aryltetrazole derivative [II] can be produced according to the method described in WO 2009/49305 or a method analogous thereto.

Step 1

Compound [IV] can be produced by reacting aryltetrazole derivative [II] with benzene derivative [III] in the presence of a metal catalyst and a base. This reaction can also be carried out using a solvent.

Examples of the metal catalyst include catalysts such as ruthenium catalysts, iridium catalysts, rhodium catalysts, palladium catalysts, nickel catalysts, copper catalysts, iron catalysts, cobalt catalysts and the like. They can be used alone or in admixture thereof. Examples of the ruthenium catalyst include dichlorotris(triphenylphosphine)ruthenium(II) ($RuCl_2(PPh_3)_3$), dichloro(1,5-cyclooctadiene)ruthenium(II) polymer (sometimes to be referred to as $[RuCl_2(\eta^4\text{-COD})]_n$ or poly[($\eta^2,\eta^2$-cycloocta-1,5-diene)ruthenium-di-μ-chloro]), $[RuCl_2(\eta^6\text{-}C_6H_6)]_2$, dichloro(p-cymene)ruthenium (II) ([Ru(p-cymene)$Cl_2]_2$), dichloro(mesitylene)ruthenium (II) ([Ru(mesitylene)$Cl_2]_2$), Ruthenium(III) chloride (RuCl$_3$), Ruthenium(III) chloride hydrate (RuCl$_3$.xH$_2$O) and ruthenium carbon. The amount of the metal catalyst to be used is generally 0.00001-10 equivalents, preferably 0.001-0.3 equivalents, relative to aryltetrazole derivative [II].

Examples of the base include potassium carbonate (K$_2$CO$_3$), sodium carbonate (Na$_2$CO$_3$), sodium hydrogen carbonate (NaHCO$_3$), potassium hydrogen carbonate (KHCO$_3$), potassium phosphate (K$_3$PO$_4$), cesium carbonate (Cs$_2$CO$_3$), rubidium carbonate (Rb$_2$CO$_3$) and the like. The amount of the base to be used is generally 0.1-10 equivalents, preferably 1-3 equivalents, more preferably 1-2 equivalents, relative to aryltetrazole derivative [II].

For preferable progress of the reaction, a ligand may be added to the reaction system. Examples of the ligand include triphenylphosphine (sometimes to be referred to as triphenylphosphane), tri(t-butyl)phosphine, triethyl phosphite, tricyclohexylphosphine, trio-tolyl)phosphine, tri(p-tolyl)phosphane, tri(p-methoxyphenyl)phosphane, cyclohexyldiphenylphosphane, acetic acid, trifluoroacetic acid, methanesulfonic acid, p-toluenesulfonic acid, benzenesulfonic acid, 2,4,6-trimethylbenzoic acid, 1-adamantylcarboxylic acid and the like. The amount of the ligand to be used is generally 0.00001-10 equivalents, preferably 0.001-1 equivalents, relative to aryltetrazole derivative [II].

The solvent is not particularly limited as long as the reaction proceeds, and preferable examples thereof include polar solvents such as N-methyl-2-pyrrolidone (sometimes to be abbreviated as NMP), N,N-dimethylformamide (sometimes to be abbreviated as DMF), N,N-dimethylacetamide (sometimes to be abbreviated as DMA), dimethyl sulfoxide (sometimes to be abbreviated as DMSO) and the like, non-polar solvents such as toluene, xylene and the like, and a mixture of polar solvent and non-polar solvent. The amount of the solvent to be used is generally 0-100 mL, preferably 0.1-10 mL, per 1 mmol of aryltetrazole derivative [II].

The reaction temperature is generally 20-300° C., preferably 100-200° C.

The reaction time is generally 0.01-200 hr, preferably 0.5-24 hr.

Step 2a

When R$^2$ in compound [IV] is a methyl group substituted by hydroxyl group(s) protected by a protecting group, compound [V] can be produced by deprotecting compound [IV] in the presence of a base. This reaction can also be carried out using a solvent.

Examples of the base include sodium methoxide, sodium ethoxide, dimethylamine, methylamine, ammonia, potassium carbonate, sodium carbonate and the like. The amount of the base to be used is generally 0.001-10 equivalents, preferably 0.01-1 equivalents, relative to compound [IV].

The solvent is not particularly limited as long as the reaction proceeds, and examples thereof include methanol, ethanol, propanol and the like. The amount of the solvent to be used is generally 0.01-100 mL, preferably 0.1-10 mL, per 1 mmol of compound [IV].

The reaction temperature is generally −50-100° C., preferably 0-40° C.

The reaction time is generally 0.001-10 hr, preferably 0.1-5 hr.

Step 2b

When R$^2$ in compound [IV] is a lower alkoxycarbonyl group, compound [V] can be produced by reducing compound [IV] in the presence of a reducing agent. This reaction can also be carried out using a solvent.

Examples of the reducing agent include sodium borohydride (hereinafter sometimes to be referred to as sodium tetrahydroborate), lithium aluminum hydride, diisobutylaluminum hydride and the like. The amount of the reducing agent to be used is generally 1-5 equivalents, preferably 1-2 equivalents, relative to compound [IV].

For preferable progress of the reaction, a metal salt may be added to the reaction system. Examples of the metal salt include calcium chloride, zinc chloride and the like. The amount of the metal salt to be used is generally 0.1-2 equivalents, preferably 0.5-1 equivalents, relative to compound [IV]. When lithium aluminum hydride or diisobutylaluminum hydride is used as a reducing agent, the reaction proceeds in the absence of a metal salt.

The solvent is not particularly limited as long as the reaction proceeds, and examples thereof include ethanol, 2-propanol, methanol and the like. The amount of the solvent to be used is generally 1-50 mL, preferably 1-2 mL, per 1 mmol of compound [IV].

The reaction temperature is generally −50-120° C., preferably 0-80° C.

The reaction time is generally 0.1-24 hr, preferably 3-10 hr.

Step 3

When R$^2$ in compound [IV] is a methyl group, biaryltetrazole derivative [I] or a salt thereof can be produced by reacting compound [IV] with a halogenating reagent in the presence of azobisisobutyronitrile (AIBN).

When R$^2$ in compound [IV] is a methyl group substituted by hydroxyl group(s) protected by a protecting group, or a lower alkoxycarbonyl group, biaryltetrazole derivative [I] or a salt thereof can be produced by reacting compound [V] with a halogenating reagent.

These reactions can also be carried out using a solvent.

The halogenating reagent is not particularly limited, and a halogenating reagent known per se can be applied. Examples thereof include phosphorus tribromide, thionyl bromide, hydrobromic acid, hydrogen chloride, thionyl chloride, carbon tetrachloride/triphenylphosphine, bromotrimethylsilane, N-bromosuccinimide (NBS) and the like. The amount of the halogenating reagent to be used is generally 1-10 equivalents, preferably 1-3 equivalents, relative to compound [V].

The solvent is not particularly limited as long as the reaction proceeds, and examples thereof include tetrahydrofuran (sometimes to be abbreviated as THF), toluene, ethyl acetate, dioxane, methyl t-butyl ether (MTBE), chloroform, methylene chloride, diisopropyl ether, acetonitrile and the like. The amount of the solvent to be used is generally 0.01-100 mL, preferably 0.1-10 mL, per 1 mmol of compound [V].

The reaction temperature is generally −50-150° C., preferably −20-50° C.

The reaction time is generally 0.001-24 hr, preferably 0.1-10 hr.

[Production Method 2]

Step 1

Compound [VII] can be produced by reacting biaryltetrazole derivative [I] obtained in the aforementioned Production Method 1 with compound [VI] in the presence of a base. This reaction can also be carried out using a solvent.

Examples of the base include is not particularly limited, and a base known per se can be applied. Examples thereof include potassium carbonate, cesium carbonate, sodium hydroxide, potassium hydroxide, triethylamine, diisopropylethylamine, 1,8-diazabicyclo[5.4.0]undeca-7-ene(DBU) and the like. The amount of the base to be used is generally 1-10 equivalents, preferably 1-3 equivalents, relative to biaryltetrazole derivative [I].

The solvent is not particularly limited as long as the reaction proceeds, and examples thereof include DMA, DMF, DMSO, NMP, acetonitrile, toluene, THF, dioxane and the like. The amount of the solvent to be used is generally 0.001-100 mL, preferably 0.1-10 mL, per 1 mmol of biaryltetrazole derivative [I].

The reaction temperature is generally −50-150° C., preferably −20-50° C.

The reaction time is generally 0.1-48 hr, preferably 0.5-5 hr.

Step 2-A(1)

Compound [VIII] can be produced by reducing compound [VII] in the presence of a reducing agent. This reaction can also be carried out using a solvent.

Examples of the reducing agent include is not particularly limited, and a reducing agent known per se can be applied. Examples thereof include sodium borohydride, lithium borohydride, boron zinc borohydride, sodium triacetoxyborohydride and the like. The amount of the reducing agent to be used is generally 1-10 equivalents, preferably 1-5 equivalents, relative to compound [VII].

The solvent is not particularly limited as long as the reaction proceeds, and examples thereof include methanol, water, ethanol, isopropyl alcohol, dimethoxyethane and the like. The amount of the solvent to be used is generally 0.01-100 mL, preferably 0.1-10 mL, per 1 mmol of compound [VII].

A base can also be used for this reaction as necessary. Examples of the base include sodium hydroxide and the like. The amount of the base to be used is generally 0-10 equivalents, preferably 1-2 equivalents, relative to compound [VII].

The reaction temperature is generally −50-100° C., preferably −20-50° C.

The reaction time is generally 0.01-48 hr, preferably 0.1-5 hr.

Step 2-A(2)

Compound [IX] can be produced by deprotecting compound [VIII] (removing $R^1$) in the presence of an acid.

The acid is not particularly limited, and an acid known per se can be applied. Examples thereof include trifluoroacetic acid, trichloroacetic acid, trifluoromethanesulfonic acid, methanesulfonic acid, sulfuric acid, hydrochloric acid and the like. The amount of the acid to be used is generally 0.1-1000 equivalents, preferably 1-500 equivalents, relative to compound [VIII].

The deprotection using an acid can be preferably carried out in the presence of a scavenger. The scavenger is not particularly limited as long as the reaction proceeds, and examples thereof include anisole, mesitylene, mercaptans such as 1-octanethiol and the like, and the like. The amount of the scavenger to be used is generally 0.001-10 mL, preferably 0.1-5 mL, per 1 mmol of compound [VIII].

The above-mentioned acid or scavenger may act as a solvent in this step.

The reaction temperature is generally −50-150° C., preferably 10-100° C.

The reaction time is generally 0.1-48 hr, preferably 0.5-20 hr.

Reduction (e.g., catalytic reduction, formic acid reduction etc.) can also be employed for deprotecting compound [VIII]. This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [VIII].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include isopropyl alcohol, n-propyl alcohol, methanol, ethanol, tetrahydrofuran, methylene chloride, ethyl acetate and the like, and a mixed solvent of the above-mentioned solvent and water. The amount of the solvent to be used is generally 0.1-100 mL, preferably 0.5-10 mL, per 1 mmol of compound [VIII].

The reaction temperature is generally 0-150° C., preferably 10-80° C.

The reaction time is generally 0.1-72 hr, preferably 0.5-24 hr.

Step 2-B(1)

Compound [VIII-2] can be produced by deprotecting compound [VII] (removing $R^1$) in the same manner as in the method described in the above-mentioned Step 2-A(2) of Production Method 2 (deprotection of compound [VIII]).

Step 2-B(2)

Compound [IX] can be produced by reducing compound [VIII-2] in the same manner as in the method described in the above-mentioned Step 2-A(1) of Production Method 2 (reduction of compound [VII]).

[Production Method 3]

Step 1

Compound [XI] can be produced by reacting biaryltetrazole derivative [I] obtained in the aforementioned Production Method 1 with compound [α] or a salt thereof (e.g., p-toluenesulfonate, hydrochloride etc.) in the presence of a base. This reaction can also be carried out using a solvent.

Examples of the base include is not particularly limited, and a base known per se can be applied. Examples thereof include ethyldiisopropylamine, triethylamine, pyridine, sodium hydride, potassium t-butoxide and the like. The amount of the base to be used is generally 1-10 equivalents, preferably 1-5 equivalents, relative to biaryltetrazole derivative [I].

The solvent is not particularly limited as long as the reaction proceeds, and examples thereof include acetonitrile, toluene, THF, dioxane, chloroform, methylene chloride and the like. The amount of the solvent to be used is generally 0.1-100 ml, preferably 0.5-5 ml, per 1 mmol of biaryltetrazole derivative [I].

The reaction temperature is generally −50-150° C., preferably 5-100° C.

The reaction time is generally 0.1-48 hr, preferably 0.5-5 hr.

Step 2-A(1)

Compound [XII] can be produced by deprotecting compound [XI] (removing $R^1$) in the presence of an acid.

The acid is not particularly limited, and an acid known per se can be applied. Examples thereof include trifluoroacetic acid, trichloroacetic acid, trifluoromethanesulfonic acid, methanesulfonic acid, sulfuric acid, hydrochloric acid and the like. The amount of the acid to be used is generally 0.1-1000 equivalents, preferably 1-500 equivalents, relative to compound [XI].

The deprotection using an acid can be preferably carried out in the presence of a scavenger. The scavenger is not particularly limited as long as the reaction proceeds, and examples thereof include anisole, mesitylene, mercaptans such as 1-octanethiol and the like, and the like. The amount of the scavenger to be used is generally 0.001-10 mL, preferably 0.1-5 mL, per 1 mmol of compound [XI].

The above-mentioned acid or scavenger may act as a solvent in this step.

The reaction temperature is generally −50-150° C., preferably 10-100° C.

The reaction time is generally 0.1-48 hr, preferably 0.5-5 hr.

Reduction (e.g., catalytic reduction, formic acid reduction etc.) can also be employed for deprotecting compound [XI]. This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [XI].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include isopropyl alcohol, n-propyl alcohol, methanol, ethanol, tetrahydrofuran, methylene chloride, ethyl acetate and the like, and a mixed solvent of the above-mentioned solvent and water. The amount of the solvent to be used is generally 0.1-100 mL, preferably 0.5-10 mL, per 1 mmol of compound [XI].

The reaction temperature is generally 0-150° C., preferably 10-80° C.

The reaction time is generally 0.1-72 hr, preferably 0.5-24 hr.

Step 2-A(2)

Compound [XIV] can be produced by reacting compound [XII] with compound [XIII] in the presence of a base. This reaction can also be carried out using a solvent.

The base is not particularly limited, and examples thereof include triethylamine, ethyldiisopropylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP), lutidine, pyridine and the like. The amount of the base to be used is generally 1-10 equivalents, preferably 1-3 equivalents, relative to compound [XII].

The solvent is not particularly limited as long as the reaction proceeds, and examples thereof include toluene, xylene, methylene chloride, chloroform, acetonitrile, NMP, DMF, DMSO, THF, dimethoxyethane, t-butyl methyl ether (hereinafter sometimes to be referred to as t-BME), 1,4-dioxane and the like. The amount of the solvent to be used is generally 0.001-100 mL, preferably 0.1-10 mL, per 1 mmol of compound [XII].

The reaction temperature is generally −20-150° C., preferably 0-100° C.

The reaction time is generally 0.1-48 hr, preferably 0.5-5 hr.

Step 2-A(3)

Compound [XV] can be produced by deprotecting compound [XIV] (removing $R^3$) in the presence of an acid.

The acid is not particularly limited, and an acid known per se can be applied. Examples thereof include trifluoroacetic acid, trichloroacetic acid, trifluoromethanesulfonic acid, methanesulfonic acid, sulfuric acid, hydrochloric acid and the like. The amount of the acid to be used is generally 0.1-1000 equivalents, preferably 1-500 equivalents, relative to compound [XIV].

The deprotection using an acid can be preferably carried out in the presence of a scavenger. The scavenger is not particularly limited as long as the reaction proceeds, and examples thereof include anisole, mesitylene, mercaptan and the like. The amount of the scavenger to be used is generally 0.001-10 mL, preferably 0.1-5 mL, per 1 mmol of compound [XIV].

The above-mentioned acid or scavenger may act as a solvent in this step.

The reaction temperature is generally −50-150° C., preferably 10-100° C.

The reaction time is generally 0.1-48 hr, preferably 0.5-5 hr.

Alternatively, compound [XV] can also be produced by deprotecting compound [XIV] (removing $R^3$) in the presence of a base. This reaction can also be carried out using a solvent.

Examples of the base include sodium methoxide, sodium ethoxide, dimethylamine, methylamine, ammonia, potassium carbonate, sodium carbonate and the like. The amount of the base to be used is generally 0.001-10 equivalents, preferably 0.01-1 equivalents, relative to compound [XIV].

The solvent is not particularly limited as long as the reaction proceeds, and examples thereof include methanol, ethanol, propanol and the like. The amount of the solvent to be used is generally 0.01-100 mL, preferably 0.1-10 ml, per 1 mmol of compound [XIV].

The reaction temperature is generally −50-100° C., preferably 0-20° C.

The reaction time is generally 0.001-10 hr, preferably 0.1-5 hr.

Alternatively, compound [XV] can also be produced by deprotecting compound [XIV] (removing $R^3$) by reduction (e.g., catalytic reduction, formic acid reduction etc.). This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [XIV].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include n-propyl alcohol, methanol, ethanol, tetrahydrofuran, methylene chloride, ethyl acetate and the like, and a mixed solvent of the above-mentioned solvent and water. The amount of the solvent to be used is generally 0.1-100 mL, preferably 0.5-10 mL, per 1 mmol of compound [XIV].

The reaction temperature is generally 0-150° C., preferably 10-80° C.

The reaction time is generally 0.1-72 hr, preferably 0.5-24 hr.

Step 2-B(1)

Compound [XII-2] can be produced by reacting compound [XI] with compound [XIII] in the same manner as in the method described in the above-mentioned Step 2-A(2) of Production Method 3 (reaction of compound [XII] and compound [XIII]).

Step 2-B(2)

Compound [XV] can be produced by deprotecting compound [XII-2] (removing $R^1$ and $R^3$) in the same manner as in the method described in the above-mentioned Step 2-A(1) and (3) of Production Method 3 (deprotection of compound [XI] and [XIV]).

Alternatively, compound [XV] can also be produced by deprotecting compound [XII-2] (removing $R^1$ and $R^3$) by reduction (e.g., catalytic reduction, formic acid reduction). This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [XII-2].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include n-propyl alcohol, methanol, ethanol, tetrahydrofuran, methylene chloride, ethyl acetate and the like, and a mixed solvent of the above-mentioned solvent and water. The amount of the solvent to be used is, generally 0.1-100 mL, preferably 0.5-10 mL, per 1 mmol of compound [XII-2].

The reaction temperature is generally 0-150° C., preferably 10-80° C.

The reaction time is generally 0.1-72 hr, preferably 0.5-24 hr.

[Production Method 4]

Step 1

Compound [XVII] can be produced by reacting biaryltetrazole derivative [I] obtained in the aforementioned Production Method 1 with compound [XVI] or a salt thereof (e.g., hydrochloride etc.) in the presence of a base or a combination of a base and an additive. This reaction can also be carried out using a solvent.

The base is not particularly limited, and examples thereof include triethylamine, ethyldiisopropylamine, DBU, sodium hydroxide, sodium carbonate, sodium hydrogen carbonate, potassium hydroxide, potassium carbonate, potassium hydrogen carbonate, potassium phosphate, 4-dimethylaminopyridine (DMAP), and lutidine. The amount of the base to be used is generally 1-10 equivalents, preferably 1-3 equivalents, relative to biaryltetrazole derivative [I].

Examples of the additive include tetraalkylammonium halides (e.g., tetrabutylammonium bromide), tetraalkylphosphonium halides and the like. The amount of the additive to be used is generally 0.01-10 equivalents, preferably 0.05-1 equivalents, relative to biaryltetrazole derivative [I].

The solvent is not particularly limited as long as the reaction proceeds, and examples thereof include toluene, xylene, methylene chloride, chloroform, acetonitrile, DMF, DMSO, THF, dimethoxyethane, t-BME, 1,4-dioxane and the like, and a mixed solvent of the above-mentioned solvent and water. The amount of the solvent to be used is generally 0.001-100 mL, preferably 0.1-10 mL, per 1 mmol of biaryltetrazole derivative [I].

The reaction temperature is generally −20-150° C., preferably 0-100° C.

The reaction time is generally 0.1-48 hr, preferably 0.5-10 hr.

Step 2

Compound [XVIII] can be produced by deprotecting compound [XVII] (removing $R^1$). Reduction (e.g., catalytic reduction, formic acid reduction etc.) can be used for the deprotection. This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [XVII].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include isopropyl alcohol, n-propyl alcohol, methanol, ethanol, tetrahydrofuran, methylene chloride, ethyl acetate and the like, and a mixed solvent of the above-mentioned solvent and water. The amount of the solvent to be used is generally 0.1-100 mL, preferably 0.5-10 mL, per 1 mmol of compound [XVII].

The reaction temperature is generally 0-150° C., preferably 10-80° C.

The reaction time is generally 0.1-72 hr, preferably 0.5-24 hr.

[Production Method 5]

Step 1

Compound [XX] can be produced by reacting biaryltetrazole derivative [I] obtained in the aforementioned Production Method 1 with compound [XIX] in the presence or in the absence of a base. This reaction can also be carried out using a solvent.

This reaction is preferably carried out in the presence of a base. Examples of the base include metal hydrides such as sodium hydride and the like; metal alkoxides such as t-butoxy sodium, t-butoxy potassium and the like; carbonates such as potassium carbonate, potassium hydrogen carbonate, sodium carbonate, sodium hydrogen carbonate and the like, and the like. Among them, carbonate, particularly potassium carbonate is preferably used. The amount of the base to be used is generally 1-5 equivalents relative to biaryltetrazole derivative [I].

Examples of the solvent include aprotic polar solvents such as dimethylformamide, dimethyl sulfoxide, dimethylacetamide and the like; ketones such as acetone, ethylmethylketone and the like; ethers such as tetrahydrofuran, dioxane and the like; esters such as ethyl acetate and the like; aromatic hydrocarbons such as benzene, toluene, xylene and the like; halogenated hydrocarbons such as dichloromethane, chloroform, carbon tetrachloride, dichloroethane and the like; acetonitrile and the like. Among them, acetonitrile is preferably used. The amount of the solvent to be used is generally 0.1-10 mL, per 1 mmol of biaryltetrazole derivative [I].

The reaction temperature is generally 70-90° C., and the reaction time is 3-10 hr.

Step 2(1)

Compound [XXI] can be produced by deprotecting compound [XX] (removing $R^5$) in the presence of an acid.

The acid is not particularly limited, and an acid known per se can be applied. Examples thereof include Brønsted acids (e.g., trifluoromethanesulfonic acid, methanesulfonic acid, phosphoric acid, sulfuric acid, hydrochloric acid etc.) and Lewis acids (e.g., aluminum chloride, tin chloride, boranetrifluoride diethyl ether etc.). The amount of the acid to be used is generally 0.1-1000 equivalents, preferably 1-500 equivalents, relative to compound [XX].

The solvent is not particularly limited as long as the reaction proceeds, and examples thereof include water, methanol, ethanol, isopropyl alcohol, tetrahydrofuran, dimethoxyethane, methyl t-butyl ether and the like. The amount of the solvent to be used is generally 0.01-100 mL, preferably 0.1-10 mL, per 1 mmol of compound [XX].

The reaction temperature is generally −50-150° C., preferably 10-100° C.

The reaction time is generally 0.1-48 hr, preferably 0.5-20 hr.

Step 2(2)

Compound [XXII] can be produced by reducing compound [XXI] in the presence of a reducing agent. This reaction can also be carried out using a solvent.

Examples of the reducing agent include is not particularly limited, and a reducing agent known per se can be applied. Examples thereof include tin chloride, sodium borohydride, lithium borohydride, zinc borohydride, sodium triacetoxyborohydride and the like. The amount of the reducing agent to be used is generally 1-10 equivalents, preferably 1-5 equivalents, relative to compound [XXI].

The solvent is not particularly limited as long as the reaction proceeds, and examples thereof include water, methanol, ethanol, isopropyl alcohol, dimethoxyethane, methyl t-butyl ether and the like. The amount of the solvent to be used is generally 0.01-100 mL, preferably 0.1-10 mL, per 1 mmol of compound [XXI].

The reaction temperature is generally −50-100° C., preferably −20-50° C.

The reaction time is generally 0.01-48 hr, preferably 0.1-5 hr.

Step 3(1)

Compound [XXIII] can be produced by reacting compound to [XXII] with tetraethoxymethane in the presence or the absence of a solvent.

The solvent is not particularly limited as long as the reaction proceeds, and examples thereof include ethanol, tetrahydrofuran, toluene, ethyl acetate, acetic acid, dimethoxyethane, methyl t-butyl ether and the like.

The reaction temperature is generally 0-120° C., preferably 50-100° C.

The reaction time is generally 0.01-48 hr, preferably 0.1-5 hr.

Step 3(2)

Compound [XXIV] can be produced by deprotecting compound [XXIII] (removing $R^4$) by hydrolysis in the presence of a base or acid and an aqueous organic solvent.

Examples of the base include is not particularly limited, and a base known per se can be applied. Examples thereof include sodium hydroxide, potassium hydroxide, sodium carbonate, potassium carbonate and sodium hydride. The acid is not particularly limited, and an acid known per se can be applied. Examples thereof include trifluoroacetic acid, trichloroacetic acid, trifluoromethanesulfonic acid, methanesulfonic acid, sulfuric acid, hydrochloric acid and the like.

Examples of the aqueous organic solvent include methanol, ethanol, acetone and the like.

The reaction temperature is generally 0-120° C., preferably 50-100° C.

The reaction time is generally 0.1-48 hr, preferably 0.5-5 hr.

Step 4(1)

Compound [XXVI] can be produced by reacting compound [XXIV] with compound [XXV] in the presence of a base. This reaction can also be carried out using a solvent.

Examples of the base include is not particularly limited, and a base known per se can be applied. Examples thereof include sodium hydroxide, potassium hydroxide, sodium carbonate, potassium carbonate, sodium hydrogen carbonate, potassium hydrogen carbonate, triethylamine, tributylamine, methylamine and dimethylamine.

The solvent is not particularly limited as long as the reaction proceeds, and examples thereof include methanol, ethanol, isopropyl alcohol, dimethylformamide and the like. The amount of the solvent to be used is generally 0.01-100 mL, preferably 0.1-10 mL, per 1 mmol of compound [XXIV].

The reaction temperature is generally −50-150° C., preferably 10-100° C.

The reaction time is generally 0.1-48 hr, preferably 0.5-20 hr.

Step 4(2)

Compound [XXVII] can be produced by deprotecting compound [XXVI] (removing $R^1$). Reduction (e.g., catalytic reduction, formic acid reduction etc.) can be used for the deprotection. This reaction can also be carried out using a solvent.

The reduction can be carried out in the presence of a catalyst. The catalyst is not particularly limited as long as it can be used for catalytic reduction or formic acid reduction, and examples thereof include palladium carbon, palladium black, palladium oxide, palladium chloride, palladium acetate and the like. The amount of the catalyst to be used is generally 0.0001-10 equivalents, preferably 0.01-0.1 equivalents, relative to compound [XXVII].

In the catalytic reduction, the hydrogen pressure is 1-100 pressure, preferably 1-10 pressure.

In the formic acid reduction, formic acid or a formate (ammonium formate etc.) is added to the reaction system as an additive.

The solvent is not particularly limited as long as the reaction proceeds, and examples thereof include isopropyl alcohol, n-propyl alcohol, methanol, ethanol, tetrahydrofuran, methylene chloride, ethyl acetate and the like, and a mixed solvent of the above-mentioned solvent and water. The amount of the solvent to be used is generally 0.1-100 mL, preferably 0.5-10 mL, per 1 mmol of compound [XXVI].

The reaction temperature is generally 0-150° C., preferably 10-80° C.

The reaction time is generally 0.1-72 hr, preferably 0.5-24 hr.

This reaction can be carried out under the condition of basic pH 7-14, or pH 7.

The compound (I) is not particularly limited, and examples thereof include salts with hydrochloric acid, sulfuric acid and the like.

The salt of compound (IX), compound (XVIII) or compound (XXVII) is not particularly limited as long as it is pharmacologically acceptable, and examples thereof include salts with a mineral acid such as hydrochloric acid, sulfuric acid, hydrobromic acid, phosphoric acid and the like; salts with an organic acid such as methanesulfonic acid, p-toluenesulfonic acid, acetic acid, oxalic acid, citric acid, malic acid, fumaric acid and the like; salts with an alkali metal such as sodium, potassium and the like; salts with an alkaline earth metal such as magnesium and the like; and salts with an amine such as ammonia, ethanolamine, 2-amino-2-methyl-1-propanol and the like.

The salt of compound (XV) is not particularly limited as long as it is pharmacologically acceptable, and examples thereof include
salts with an alkali metal such as sodium, potassium and the like;
salts with an alkaline earth metal such as magnesium and the like; and
salts with an amine such as ammonia, ethanolamine, 2-amino-2-methyl-1-propanol and the like.

Compound (I), compound (IX), compound (XV), compound (XVIII) or compound (XXVII) or a salt thereof encompass a solvate. Examples of the solvate include hydrate, alcohol solvate (e.g., methanol solvate, ethanol solvate).

EXAMPLES

The present invention is specifically explained by referring to the following Reference Examples and Examples, which are not to be construed as limitative.

In the following Reference Examples and Examples, the "room temperature" means a temperature of 15-30° C.

In the following Reference Examples and Examples, the "$C_M$" means a main conformer, and the "$C_m$" means a sub conformer.

In the following Reference Examples and Examples, the "%" in the concentration and content means "wt %", unless otherwise specified.

Reference Example 1

Step 1

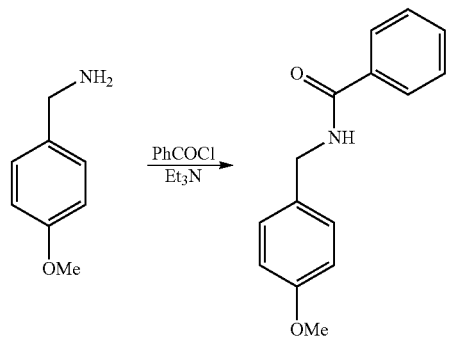 [SMILES: "Et3N" ; "PhCOCl" ; COc1ccc(CN)cc1 ; COc1ccc(CNC(=O)c2ccccc2)cc1]

To a mixture of p-methoxybenzylamine (181 g, 1.32 mol), triethylamine (185 mL, 134 g, 1.32 mol) and THF (772 mL) was added dropwise benzoyl chloride (185 g, 1.32 mol) at 16° C. or lower. The mixture was stirred at 7° C. or lower for 3 hr, water (400 mL) was added dropwise thereto at 14° C. or lower. The mixture was extracted with ethyl acetate (140 ml), and the aqueous layer was extracted with ethyl acetate (360 ml). The combined organic layers were washed successively with 20% brine (0.15 kg×2) and 20% brine (0.22 kg, once), and dried over magnesium sulfate (50 g). Silica gel (22 g) was added to the solution, and the mixture was filtered (silica gel precoat). The filtrate was concentrated to 0.67 kg under reduced pressure at 60° C. or lower, and the residue was cooled to 5° C. The resulting crystals were collected by filtration, washed with cold ethyl acetate (140 mL), and dried under reduced pressure at 50° C. to give N-(p-methoxybenzyl)benzamide (257 g, yield 80.7%) as white crystals.

melting point: 98-99° C.

IR (KBr): 3245 (NH), 1632 (C=O)cm$^{-1}$ $^1$H-NMR (CDCl$_3$): δ=7.78 (d, J=8.2 Hz, 2H, Bz), 7.49 (t, J=8.2 Hz, 1H, Bz), 7.42 (t, J=8.2 Hz, 2H, Bz), 7.29 (t, J=8.7 Hz, 2H, Ph), 6.88 (d, J=8.7 Hz, 2H, Ph), 6.36 (br s, 1H, NH), 4.58 (d, J=5.6 Hz, 2H, CH$_2$N), 3.80 (s, 3H, MeO).

Step 2

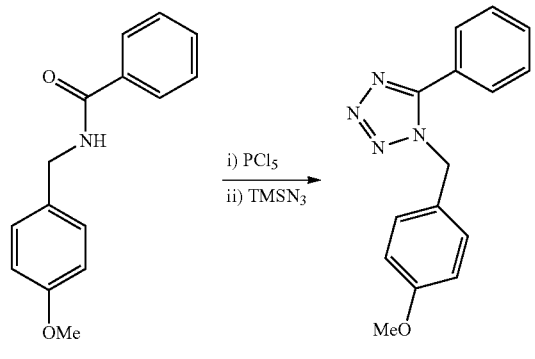

To a mixture of N-(p-methoxybenzyl)benzamide (193 g, 0.798 mol) and dichloromethane (1.55 L) was added phosphorus pentachloride (183 g, 0.880 mol) at −11-−5° C. This mixture was warmed to 19° C., and concentrated to 0.29 L under reduced pressure at 15° C. or lower. To the mixture was added dichloromethane (1.25 L), and then added dropwise azidotrimethylsilane (135 g, 1.17 mol) over 2 hr at −6° C. or lower. The reaction mixture was stirred at room temperature for 5 hr, and saturated aqueous sodium hydrogen carbonate solution (1.0 L) was added dropwise thereto at 13° C. or lower. Saturated aqueous sodium hydrogen carbonate solution (4.6 L) was added again thereto. The organic layer was separated, and the aqueous layer was extracted with dichloromethane (1.25 L). The combined organic layers were washed with 20% brine (0.85 k g), dried over magnesium sulfate (43 g), and concentrated under reduced pressure at 50° C. or lower to give compound 1a as a crude product (258 g). The content of compound 1a in the crude product was 81.2% measured by HPLC, and the net yield was 209 g (89.2%).

$^1$H-NMR (CDCl$_3$): δ=7.60-7.52 (m, 5H, Ph), 7.10 (d, J=8.8 Hz, 2H, Ph), 6.86 (d, J=8.8 Hz, 2H, Ph), 5.55 (s, 2H, CH$_2$), 3.79 (s, 2H, CH$_3$O).

MS: calcd for C$_{15}$H$_{15}$N$_4$O [M+H]$^+$ 267. found 267

Reference Example 2

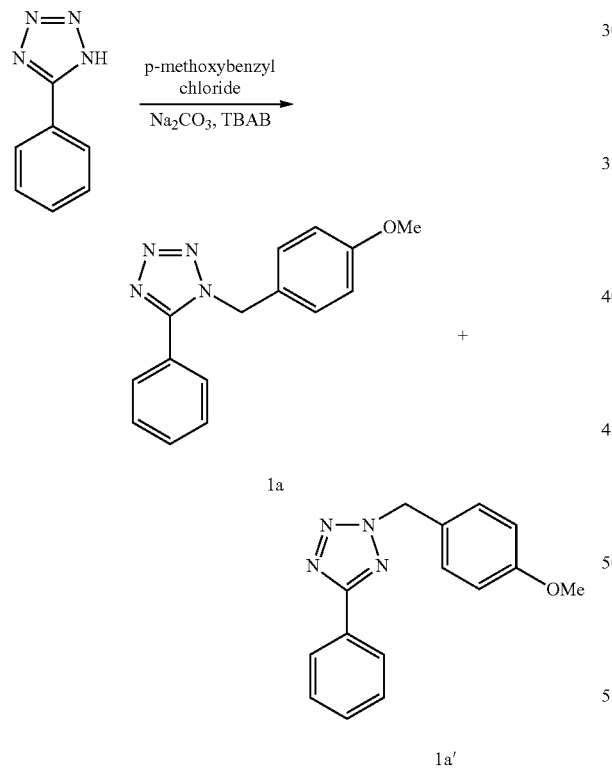

Into a 500 mL four-neck flask were charged 5-phenyl-1H-tetrazole (14.64 g, 100 mmol), sodium carbonate (15.91 g, 150 mmol), tetrabutylammonium bromide (sometimes to be abbreviated as TBAB, 0.71 g, 2.2 mmol) and water (120 ml). A solution of p-methoxybenzyl chloride (15.40 g, 98 mmol) in chloroform (160 mL) was added dropwise thereto over 1 hr under ice-cooling, and the mixture was stirred at 55° C. for 1 hr. After completion of the reaction, the organic layer was separated, and the aqueous layer was extracted again with chloroform (120 mL). The combined organic layers were dried over magnesium sulfate, and concentrated to give a white solution (27.81 g, yield 107%).

The composition ratio (molar ratio) of the crude product was 1-methoxybenzyl form (compound 1a):2-methoxybenzyl form (compound 1a'):p-methoxybenzyl alcohol=43:16:41 determined by $^1$H-NMR.

To the obtained crude product (27.81 g, p-methoxybenzyl alcohol content: 7.5 g, 54 mmol) were added THF (100 mL), acetic anhydride (6.02 g, 59 mmol), triethylamine (1.82 g, 18 mmol) and N,N-dimethyl-4-aminopyridine (sometimes to be abbreviated as DMAP) (0.66 g, 5.4 mmol), and the mixture was stirred for 1 hr. Methanol (20 mL) was added thereto, and the solvent was evaporated. The residue was dissolved in ethyl acetate (100 mL), and the solution was washed with water (20 mL×2). The organic layer was concentrated and vacuum-dried to give a pale white solution (22.02 g).

The above-mentioned acetylated solution (20.02 g) was purified by silica gel column chromatography (ethyl acetate/hexane=1/3-1/2) to give compound 1a (9.62 g, yield 37%) as a white solid.

$^1$H-NMR (400 MHz, CDCl$_3$) δ=3.79 (3H, s), 5.55 (2H, s), 6.84-6.88 (2H, m), 7.08-7.13 (2H, m), 7.48-7.62 (5H, m).

$^{13}$C-NMR (400 MHz, CDCl$_3$) δ=123.77, 125.72, 154.28, 159.61 (4s), 114.37, 128.63, 128.78, 129.01, 131.12 (5d), 51.03 (1t), 55.37 (1q).

IR (KBr) ν(cm$^{-1}$):1611
EIMS (m/z):266 (M$^+$)
melting point: 37.7-38.3° C.

Reference Example 3

Step 1

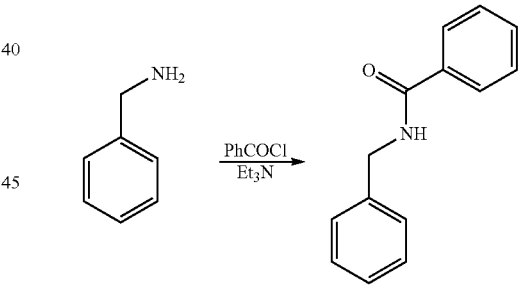

To a mixture of benzylamine (75.0 g, 0.700 mol), THF (300 mL) and triethylamine (70.8 g, 134 g, 0.700 mol) was added dropwise benzoyl chloride (98.4 g, 0.700 mol) at 2° C. or lower, and the mixture was allowed to warm, and stirred at 12-35° C. for 3 hr. The progress of the reaction was confirmed by TLC (eluent: toluene/ethyl acetate (4:1)). To the reaction mixture was added water (165 mL) at 16° C. or lower, the mixture was extracted with ethyl acetate (60 mL), and the aqueous layer was extracted with ethyl acetate (150 mL). The combined organic layers were washed successively with 5% aqueous citric acid solution (50 mL×2) and 20% brine (75 mL×3), and dried over magnesium sulfate (20 g). The silica gel (12 g) was added to the solution, and the mixture was filtered through silica gel. The filtrate was concentrated under reduced pressure at 40° C. until the beginning of the precipitation. To the concentrate (263 g) was added ethyl acetate (41.5 g), and the resulting solid was dissolved at 60° C. The solution was cooled over 2 hr to 20° C., and ethyl acetate (40 mL) was added thereto. Then, the mixture was cooled to 5° C., and the resulting crystals were collected by filtration, and washed with cold ethyl acetate (75 mL). The obtained crystals were dried under reduced pressure at 40° C. to give N-benzylbenzamide (116 g, yield 78.5%) as white crystals.

melting point: 104-105° C.

IR (KBr): 3244 (NH), 1633 (C=O) cm$^{-1}$ $^1$H-NMR (CDCl$_3$): δ=7.79 (d, J=8.0 Hz, 2H, Bz), 7.50 (t, J=8.0 Hz, 1H, Bz), 43 (t, J=8.0, 2H, Bz), 7.37-7.35 (m, 4H, Ph), 7.32 (m, 1H, Ph), 6.41 (br s, 1H, NH), 4.65 (d, J=5.6 Hz, 2H, CH$_2$).

Step 2

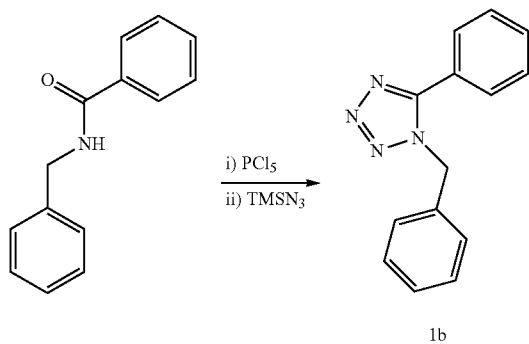 [SMILES: O=C(NCc1ccccc1)c1ccccc1 ; c1ccc(Cn2nnnc2-c2ccccc2)cc1]

1b

To a mixture of N-benzylbenzamide (62.5 g, 0.296 mol) and dichloromethane (570 mL) was added phosphorus pentachloride (67.9 g, 0.326 mol) by five portions at −15--8° C. The mixture was warmed to 21° C. over 3 hr, and concentrated to 0.17 L under reduced pressure at 21° C. or lower. To the mixture was added dichloromethane (450 mL), and then added dropwise azidotrimethylsilane (50.3 g, 0.436 mol) thereto over 0.5 hr at −8° C. or lower, and the dropping funnel was washed with dichloromethane (5 mL). The reaction mixture was allowed to warm to room temperature, and stirred for 4 hr. The disappearance of N-benzylbenzamide was confirmed by TLC (eluent: toluene/ethyl acetate (4:1)). To the reaction mixture was added saturated aqueous sodium hydrogen carbonate solution (2300 mL) at 17° C. or lower, and the organic layer was separated. The aqueous layer was extracted with dichloromethane (450 mL). The combined organic layers were washed with 20% brine (300 mL), dried over magnesium sulfate (20 g), and concentrated under reduced pressure at 40° C. or lower to give a crude product (69.8 g, 99.8% of the theoretical yield) as a yellow cloudy oil.

The obtained crude product (69.0 g) was dissolved in isopropyl alcohol (75.9 ml) with heating, the solution was filtrated hot, and the insoluble material was washed with isopropyl alcohol (4.7 ml). The filtrate was cooled to −1° C. over 7 hr. During cooling, seed crystals were added thereinto at 38° C. The precipitated crystals were collected by filtration, washed with cold isopropyl alcohol (20 mL), and dried under reduced pressure to give compound 1b (65.4 g, yield 94.7%).

melting point: 66.0-67.5° C.

IR (KBr):1606 cm$^{-1}$ $^1$H-NMR (CDCl$_3$): δ=7.58 (d, J=7.9 Hz, 2H, 5-Ph), 7.57 (t, J=7.9 Hz, 1H, 5-Ph), 7.50 (t, J=7.9 Hz, 2H, 5-Ph), 7.37-7.34 (m, 3H, Ph), 7.17-7.15 (m, 2H, Ph), 5.62 (s, CH$_2$).

MS:237 (MH$^+$)

Reference Example 4

Step 1

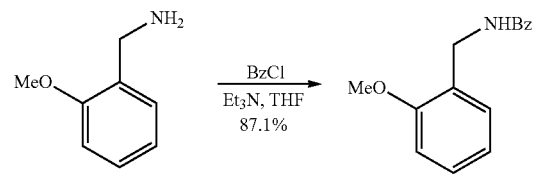

To a mixture of o-methoxybenzylamine (20.0 g, 0.146 mol), tetrahydrofuran (124 mL) and triethylamine (15.6 g, 0.154 mol) was added dropwise benzoyl chloride (20.5 g, 0.146 mol) at −9-0° C., and the dropping funnel was washed with THF (10 mL). Under a nitrogen atmosphere, the reaction mixture was gradually warmed to about 16° C. During warming, THF (total 51 ml) was appropriately added to stir the content. The reaction was confirmed by TLC (eluent: hexane/ethyl acetate (1:1)). The reaction mixture was stirred at about 16° C. for 10 hr, and cooled to 5° C. Water (44 ml) was added thereto, and the mixture was extracted three times with ethyl acetate (120 mL, 40 mL, 40 mL). The combined organic layers were washed successively with 10% hydrochloric acid (40 mL), saturated aqueous sodium hydrogen carbonate solution (40 mL), water (40 mL) and saturated brine (44 mL), and dried over magnesium sulfate (20 g), and the solvent was evaporated under reduced pressure at 40° C. or lower. Ethyl acetate was added to the residue (content 74 g), and the solid was dissolved with heating to 60° C. The solution was gradually cooled to 6° C., the precipitated crystals were collected by filtration, washed with cold ethyl acetate (10 mL), and dried under reduced pressure at 40° C. or lower to give N-benzoyl-2-methoxybenzylamine (30.7 g, 87.1%) as white crystals.

melting point: 102-104° C.

IR (KBr): 3308, 1647, 1636 cm$^{-1}$ $^1$H-NMR (DMSO-d$_6$): δ=8.86 (br t, J=6.0 Hz, 1H), 7.91 (dd, J=8.4, 1.6 Hz, 2H), 7.54 (t, J=6.9, 1.6 Hz, 1H), 7.48 (dd, J=8.9, 6.9 Hz, 2H), 7.24 (td, J=7.8, 1.4 Hz, 1H), 7.17 (dd, J=7.8, 1.4 Hz, 1H), 6.99 (d, J=7.8 Hz, 1H), 6.90 (td, J=7.8, 1.4 Hz, 1H), 4.45 (d, J=6.0 Hz, 2H), 3.83 (s, 3H).

MS: m/z=242 (MH$^+$)

Step 2

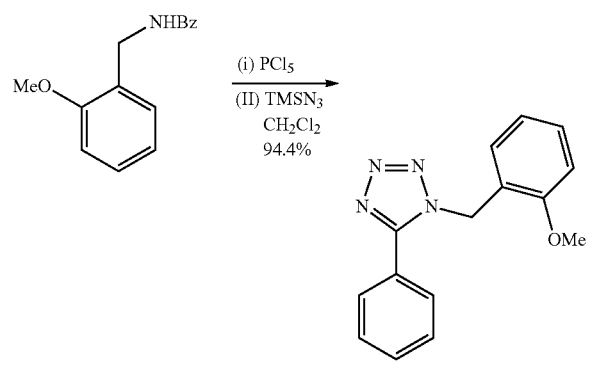

1c

To a mixture of N-benzoyl-2-methoxybenzylamine (16.0 g, 66.3 mmol) and dichloromethane (128 mL) was added phosphorus pentachloride (15.2 g, 73.1 mmol) over 11 min by five portions at −15−−11° C., and the mixture was warmed to 21° C. over 2 hr. During warming, the inner wall surface of the reaction container was washed with dichloromethane (11 mL). The reaction mixture was concentrated under reduced pressure at room temperature or lower, and dichloromethane (101 mL) was added to the residue. Azidotrimethylsilane (11.2 g, 97.5 mmol) was added dropwise thereto at −13−−10° C., and the dropping funnel was washed with dichloromethane (10 mL). The reaction mixture was allowed to warm to room temperature, and stirred for 4 hr. The reaction was monitored by TLC (eluent: toluene/ethyl acetate (4:1, 2:1)). To the reaction mixture was added dropwise saturated aqueous sodium hydrogen carbonate solution (200 mL) at 3-11° C., and then added saturated aqueous sodium hydrogen carbonate solution (80 mL). The organic layer was separated, and the aqueous layer was extracted with dichloromethane (100 mL). The combined organic layers were washed with 20% brine (50 mL), and dried over magnesium sulfate (10 g), and the solvent was evaporated under reduced pressure at 35° C. or lower. To the obtained solid (18 g) was added ethyl acetate (25 mL), and the solid was dissolved with heating in a bath at 80° C., and the solution was cooled to −3° C. over 4 hr. During cooling, seed crystals were added thereinto at 55° C. The solid was collected by filtration, washed with cold ethyl acetate (33 g), and dried under reduced pressure at 50° C. or lower to give compound 1c (primary crystal; 14.6 g, 82.5%; HPLC 99.2 area %) as white crystals. The filtrate was concentrated under reduced pressure at 40° C. or lower (content 5.6 g), and the ethyl acetate (2.7 mL) was added to the residue, and the solid was almost dissolved with heating in a bath at 70° C. The mixture was cooled to −3° C., and during cooling, seed crystals were added thereinto. The solid was collected by filtration, washed with cold ethyl acetate (2 mL), and dried under reduced pressure at 50° C. or lower to give the secondary crystals (2.11 g, 11.9%; HPLC 97.2 area %) of compound 1c as white crystals. The content of the secondary crystals was measured by HPLC using the primary crystal as a standard, and it was 96.7%.

HPLC measurement condition:

column Inertsil ODS—3.2 μm, 3.0×50 mm mobile phase A MeCN/30 mM $KH_2PO_4$ (11:9)

mobile phase B 0.1 w/v % phosphoric acid total flow 0.5 mL/min gradient cycle: 0 min (SOLUTION A/SOLUTION B=70/30), 5 min (SOLUTION A/SOLUTION B=100/0), 35 min (SOLUTION A/SOLUTION B=100/0), 38 min (SOLUTION A/SOLUTION B=70/30)

detector UV 225 nm temperature 40° C.

melting point: 100-102° C.

IR (KBr):1603 $cm^{-1}$ $^1$H-NMR (DMSO-$d_6$): δ=7.76 (dd, J=7.9, 2.2 Hz, 2H), 7.65-7.60 (m, 3H), 7.32 (td, J=8.0, 1.5 Hz, 1H), 7.09 (dd, J=8.0, 1.5 Hz, 1H), 6.97 (d, J=8.0 Hz, 1H), 6.92 (t, J=8.0 Hz, 1H), 5.64 (s, 2H), 3.58 (s, 3H).

$^{13}$C-NMR (DMSO-$d_6$): δ=157, 154, 131, 130, 130, 129, 129, 124, 122, 120, 111, 55, 46.

MS: m/z=267 ($MH^+$)

Reference Example 5

Step 1

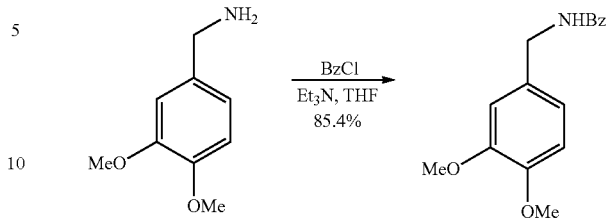

To a mixture of 3,4-dimethoxybenzylamine (24.0 g, 0.144 mol), tetrahydrofuran (192 mL) and triethylamine (15.5 g, 0.153 mol) was added dropwise benzoyl chloride (20.7 g, 0.147 mol) at −7-0° C. During addition dropwise, tetrahydrofuran (24 mL) was added thereto to stir the mixture. After adding dropwise, the dropping funnel was washed with tetrahydrofuran (12 mL), and tetrahydrofuran (24 mL) was added again thereto. The reaction mixture was gradually warmed to about 15° C. The reaction was monitored by TLC (eluent: hexane/ethyl acetate (1:1)). To the reaction mixture was added water (48 mL) at 5-8° C., and then added ethyl acetate (144 mL). The organic layer was separated, and the aqueous layer was extracted with ethyl acetate (48 mL×2). The combined organic layers were washed successively with 10% hydrochloric acid (48 mL), saturated aqueous sodium hydrogen carbonate solution (48 mL), water (48 mL) and saturated brine (48 mL), and dried over magnesium sulfate (12 g), and the solvent was evaporated under reduced pressure at 40° C. or lower. To the concentrate (40 g) was added ethyl acetate (89 g), and the mixture was homogenized with warming at 50° C., and cooled to 11° C. The solid was collected by filtration, washed with cold ethyl acetate (15 mL), and dried under reduced pressure at 40° C. or lower to give N-benzoyl-3,4-dimethoxybenzylamine (33.3 g, 85.4%) as white crystals.

melting point: 101-102° C.

IR (KBr): 3334, 1637 $cm^{-1}$

Step 2

To a mixture of N-benzoyl-3,4-dimethoxybenzylamine (31.0 g, 0.114 mol) and dichloromethane (248 mL) was added phosphorus pentachloride (26.2 g, 0.126 mol) by six portions over 12 min at −12−−10° C., and the inner of the container was washed with dichloromethane (9 mL). The reaction mixture was warmed to 22° C. over 2 hr, and the solvent was evaporated under reduced pressure. To the concentrate was added dichloromethane (220% mL), and added dropwise azidotrimethylsilane (19.3 g, 0.168 mol) over 38 min at −14--−13° C., and the dropping funnel was washed with dichloromethane (9 ml). The reaction mixture was warmed to room temperature over 4 hr, and stirred for 1 hr. Saturated aqueous sodium hydrogen carbonate solution (200 mL) is was added dropwise thereto at 3-6° C., and then saturated aqueous sodium hydrogen carbonate solution (400 mL) was added thereto. The aqueous layer was extracted with dichloromethane (186 mL), and the combined organic layers were washed with 20% brine (100 ml), dried over magnesium sulfate (15 g), and concentrated under reduced pressure in a bath at 40° C. (the concentrate solidified, content 49 g). To the obtained solid was added ethyl acetate (60 mL), and the solid was dissolved with heating at 40° C. The solution was concentrated again to 40 g under reduced pressure (the concentrate did not solidify), and ethyl acetate (25 g) was added to the residue.

A part of the obtained mixture was taken out, the solvent was replaced with chloroform, and the solvent was evaporated. Dichloromethane was added to the residue, and then added hexane to make the mixture cloudy, and the mixture was triturated. The resulting precipitated crystals were used as seed crystals.

The solvent of the rest of the mixture was replaced with chloroform, and the solvent was evaporated. Dichloromethane (35 mL) was added thereto, and then added dropwise hexane (12 mL). The seed crystals obtained in the above-mentioned operation was added thereinto to precipitate crystals. The mixture was cooled to 13° C., and the resulting solid was collected by filtration, washed with a mixed solvent of dichloromethane/hexane (7:3; 48 mL), and dried over under reduced pressure at 30° C. or lower. Since the melting of the solid was observed during dry, the solid was vacuum-dried without hot bath to give compound 1d (28.1 g, 82.8%) as a pale brown solid.

melting point: 59-61° C.

IR (KBr): 1607 cm$^{-1}$ $^1$H-NMR (DMSO-d$_6$): δ=7.76 (dd, J=7.9, 1.6 Hz, 2H), 7.65-7.59 (m, 3H), 6.87 (d, J=8.4 Hz, 1H), 6.72 (d, J=1.8 Hz, 1H), 6.59 (dd, J=8.4, 1.8 Hz, 1H), 5.70 (s, 2H), 3.70 (s, 3H), 3.62 (s, 3H).

$^{13}$C-NMR (DMSO-d$_6$): δ=153, 149, 149, 131, 129, 129, 127, 124, 120, 112, 111, 55, 55, 51.

MS: m/z=297 (MH$^+$)

Reference Example 6

Step 1

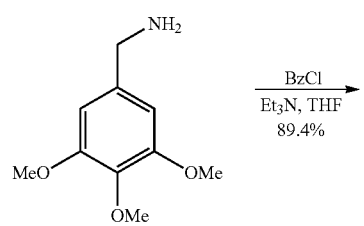

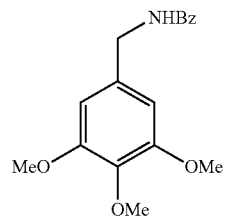

To a mixture of 3,4,5-trimethoxybenzylamine (20.0 g, 0.101 mol), THF (88.0 mL) and triethylamine (14.9 g, 0.147 mol) was added dropwise benzoyl chloride (14.3 g, 0.101 mol) at −6--−3° C., and the dropping funnel was washed with THF (10 mL). The reaction mixture was stirred under a nitrogen atmosphere at −6-2° C. for 1 hr. The consumption of the starting material was confirmed by TLC (hexane/ethyl acetate (1:1)). To the reaction mixture was added water (44 mL) at 2-10° C., and the mixture was extracted three times with ethyl acetate (17, 40, 18 mL). The combined organic layers were washed twice with 18% brine (20 mL), and dried over magnesium sulfate (7.4 g). Silica gel (5.1 g) was added thereto, and the mixture was stirred for 11 min, and filtered through silica gel (19 g). The filtrate was concentrated to 35 g under reduced pressure in a bath at 35° C. To the concentrate was added ethyl acetate, and the solid was dissolved with heating. The solvent was evaporated under reduced pressure (content 52 g) in a bath at 40-30° C. until the content ceased to flow. During evaporation, seed crystals were added thereinto. Ethyl acetate in an amount necessary for filtration was added thereto, and the crystals were collected by filtration, washed with ethyl acetate, and dried under reduced pressure at 50° C. or lower to give N-benzoyl-3,4,5-trimethoxybenzylamine (27.3 g, 89.3%) as white crystals.

melting point: 113-115° C.

IR (KBr): 3374, 1654 cm$^{-1}$

Step 2

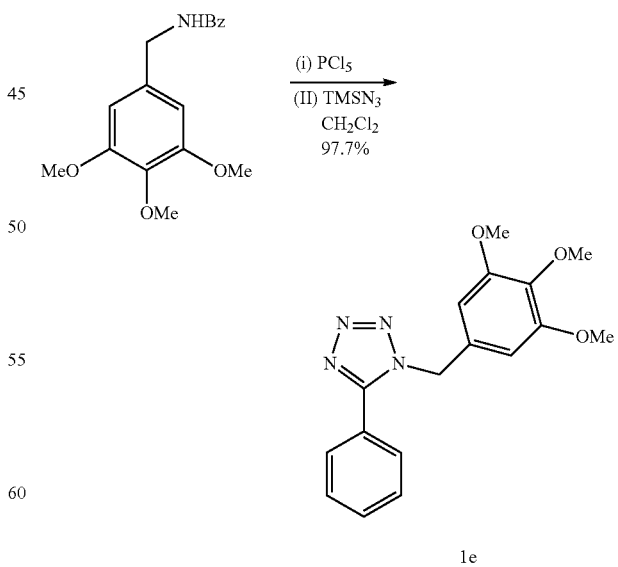

To a solution of N-benzoyl-3,4,5-trimethoxybenzylamine (15.0 g, 49.8 mmol) in dichloromethane (120 mL) was added phosphorus pentachloride (11.4 g, 54.7 mmol) over 12 min at −17-−13° C. The reaction mixture was warmed to 20° C. over 4 hr, and concentrated under reduced pressure (the bath temperature was 35° C. or lower). To the concentrate was added dichloromethane (97 mL) thereto, and added dropwise azidotrimethylsilane (8.41 g, 73.0 mmol) over 19 min at −13-−14° C., and the dropping funnel was washed with dichloromethane (5 mL). The reaction mixture was warmed to room temperature over 3 hr, and stirred for 6 hr. The reaction was monitored by TLC (eluent: toluene/ethyl acetate (7:3)). The reaction mixture was cooled, and saturated aqueous sodium hydrogen carbonate solution (250 mL) was added thereto at 3-10° C. The organic layer was separated, and the aqueous layer was extracted with dichloromethane (90 ml). The combined organic layers were washed with 20% brine (50 mL), dried over magnesium sulfate, and concentrated under reduced pressure at 40° C. or lower. To the concentrated solution was added dichloromethane (30 mL), and the mixture was concentrated again. To the concentrated solution was added dichloromethane (17 mL), and added hexane to make the mixture cloudy. The small amount of the mixture was taken out, and concentrated under reduced pressure, diisopropyl ether was added to the residue, and the mixture was triturated for crystallization. The crystals were added to the above-mentioned mixture as seed crystals for precipitation of crystals. The mixture was partially concentrated under reduced pressure, and the crystals were collected by filtration, washed with a mixed solution of hexane (40 ml) and dichloromethane (2 mL), and dried under reduced pressure at 45° C. or lower to give crude product (15.9 g, 97.7%) of compound 1e as pale brownish yellow crystals.

melting point: 105-113° C.
IR (KBr): 1595 cm$^{-1}$
$^1$H-NMR (CDCl$_3$): δ=7.61-7.52 (m, 5H), 6.34 (s, 2H), 5.54 (s, 2H), 3.82 (s, 3H), 3.76 (s, 6H).
$^{13}$(C-NMR (CDCl$_3$): δ=155, 154, 138, 131, 129, 129, 124, 105, 61, 56, 52.
MS: 327 (MH$^+$).

Reference Example 7

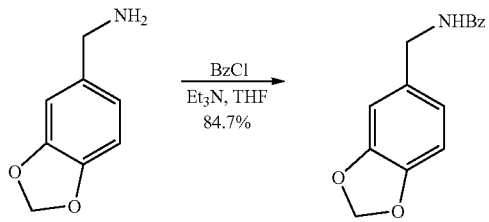

To a mixture of piperonylamine (20.0 g, 0.133 mol), tetrahydrofuran (87.5 mL) and triethylamine (13.9 g, 0.137 mol) was added dropwise benzoyl chloride (18.6 g, 0.133 mol), at −10-+6° C., and during dropwise addition, tetrahydrofuran (total 123 mL) was appropriately added thereto to stir the content. After adding dropwise, the dropping funnel was washed with tetrahydrofuran (10 mL). The reaction mixture was stirred at 2-11° C. for 15 hr under a nitrogen atmosphere. The consumption of the starting material was confirmed by TLC (eluent: hexane/ethyl acetate 1:1)). To the reaction mixture was added water (50 mL) at 11° C., and then added ethyl acetate (128 mL). The organic layer was separated, and the aqueous layer was extracted twice with ethyl acetate (44 mL). The combined organic layers were washed successively with 10% hydrochloric acid (40 mL), saturated aqueous sodium hydrogen carbonate solution (40 mL), water (40 mL) and saturated brine (44 mL), and dried over magnesium sulfate (18 g). The large part of the solvent was evaporated under reduced pressure at 35° C. or lower (content 61 g), and ethyl acetate (61 mL) was added to the residue. The crystals were collected by filtration, washed with ethyl acetate (46 mL), and dried under reduced pressure at 50° C. or lower to give N-benzoylpiperonylamine (28.6 g, 84.7%) as white crystals.

melting point: 115-116° C.
IR (KBr): 3308, 1629 cm$^{-1}$

Reference Example 8

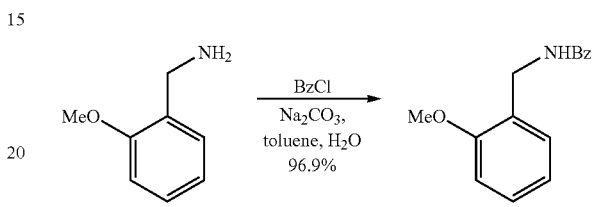

To a solution of sodium carbonate (232 g, 2.19 mol) in water (750 mL) were added toluene (750 mL) and water (750 mL), the mixture was cooled to 9° C., and o-methoxybenzylamine (300 g, 2.19 mol) was added thereto. To the mixture was added dropwise benzoyl chloride (307 g, 2.19 mol) with stirring at 3-8° C. During addition dropwise, toluene (750 mL) was added thereto to stir the mixture. The reaction mixture was allowed to warm to room temperature, and stirred for 20 min. The reaction was monitored by TLC (eluent: hexane/ethyl acetate (1:1)). The reaction mixture was cooled to 3° C., and filtered. To the solid was added city water (800 mL), and the mixture was stirred for 7.5 hr, and filtered. The organic layer of the mother liquor was concentrated to dryness. The solid collected by filtration was suspended in toluene (600 mL), the suspension was filtered, and the filtrate was concentrated to dryness. The solid collected by filtration, the residue obtained by concentration to dryness of the organic layer of the above-mentioned mother liquor, the residue obtained by concentration to dryness of the filtrate of the toluene suspension, dichloromethane (1500 mL) and water (1500 mL) were mixed, and the organic layer was separated. The organic layer was washed successively with 1 mol/L hydrochloric acid (600 mL), water (600 mL) and 20% brine (600 mL), and dried over magnesium sulfate (60 g). The magnesium sulfate was filtered off, and the filtrate was concentrated under reduced pressure in a bath at 50° C. or lower (about 830 g), and the bath temperature was decreased to 18° C. The solid was collected by filtration, washed with cold dichloromethane (85 mL), and dried under reduced pressure at 50° C. or lower to give N-benzoyl-2-methoxybenzylamine (the primary crystals 481 g, 91.2%) as white crystals. As a result of HPLC analysis, the area percentage was 99.3%, and the content was 97.8%.

The filtrate was concentrated under reduced pressure at 30° C. or lower (53.5 g), ethyl acetate (41.1 g) was added to the residue, and the residue was dissolved in a bath at 60° C. The solution was cooled to 1° C. over 4 hr, and the resulting solid was collected by filtration, washed with cold ethyl acetate (20 ml), and dried under reduced pressure at 50° C. or lower to give the secondary crystal (29.9 g, 5.7%) of N-benzoyl-2-methoxybenzylamine. As a result of HPLC analysis, the area percentage was 98.7%, and the content was 97.0%.

HPLC measurement condition:
column Inertsil ODS—3.2 μm, 3.0×50 mm
mobile phase A MeCN/30 mM $KH_2PO_4$(11:9)
mobile phase B 0.1 w/v % phosphoric acid
total flow 0.5 mL/min
gradient cycle: 0 min (SOLUTION A/SOLUTION B=70/30), 5 min (SOLUTION A/SOLUTION B=100/0), 35 min (SOLUTION A/SOLUTION B=100/0), 38 min (SOLUTION A/SOLUTION B=70/30) detector UV 225 nm
temperature 40° C.

Reference Example 9

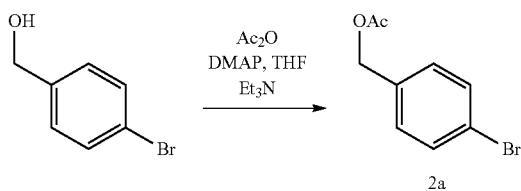 [SMILES: OCc1ccc(Br)cc1 ; CC(=O)OCc1ccc(Br)cc1]

Into 100 mL pear shape flask were charged 4-bromobenzyl alcohol (5.00 g, 26.7 mmol), THF (19 g), acetic anhydride (3.28 g, 32.1 mmol) and triethylamine (0.89 g, 8.80 mmol), and then DMAP (0.33 g, 2.70 mmol) was added thereto at 15° C. The temperature of the mixture increased to 30° C. The mixture was stirred for 1 hr, and methanol (10 g) was added thereto. The solvent was evaporated, the residue was dissolved in ethyl acetate (40 mL), and the solution was washed with water (20% mL). The organic layer was concentrated, and vacuum-dried to give compound 2a (5.52 g, yield 90.0%) as a pale yellow transparent liquid.

$^1$H-NMR (400 MHz, $CDCl_3$) δ=2.09 (3H, s), 5.04 (2H, s), 7.22 (2H, d, J=8.0), 7.47 (2H, d, J=8.4).

$^{13}$C-NMR (400 MHz, $CDCl_3$) δ=122.00, 134.69, 170.32 (3s), 129.65, 131.41 (2d), 65.35 (1t), 20.97 (1q).

IR (KBr) ν($cm^{-1}$):1738
EIMS (m/z):228 ($M^+$-1)

Reference Example 10

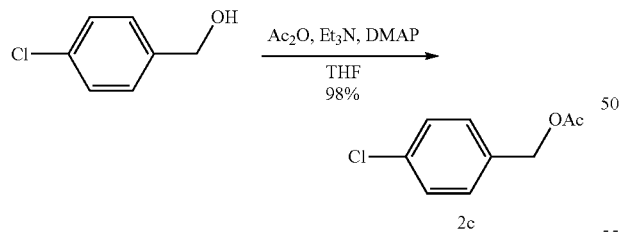

To a solution of p-chlorobenzyl alcohol (11.0 g, 77.1 mmol) in tetrahydrofuran (44.0 ml) was added dropwise acetic anhydride (8.80 g, 86.2 mmol) with stirring at −20--−18° C. under a nitrogen atmosphere, and the dropping funnel was washed with tetrahydrofuran (8.0 mL). To the solution was added dropwise triethylamine (9.50 g, 93.9 mmol) at −19--−17° C., and the dropping funnel was washed with tetrahydrofuran (6.4 mL). To the solution was added 4-dimethylaminopyridine (201 mg, 1.64 mmol) at −20° C., and the inner of the container was washed with tetrahydrofuran (1.4 mL) (the inside temperature increased to −1° C.). The cooling bath was taken off, and the inside temperature was increased to 19° C. The reaction was confirmed by TLC (eluent: hexane/ethyl acetate (2:1)). Methanol (27.0 mL) was added dropwise to the mixture at 2-19° C. under appropriate cooling, and the mixture was concentrated under reduced pressure at 45° C. or lower. The concentrate was diluted with ethyl acetate (88 mL), and the mixture was washed successively with 1 mol/L hydrochloric acid (44 mL), saturated aqueous sodium hydrogen carbonate solution (22 mL, 12 mL×2) and 20% brine (33 mL), dried over magnesium sulfate (5.0 g), and concentrated under reduced pressure at 35° C. or lower. To the concentrated solution was added chloroform (20 mL), and the mixture was concentrated under reduced pressure at 45° C. or lower. The operations were is repeated four times. The residue was dried under reduced pressure at 45° C. or lower to give compound 2c (14.0 g, 98.0%) as a slight yellow oil.

IR (neat): 1739, 1227 $cm^{-1}$

Example 1

Step 1

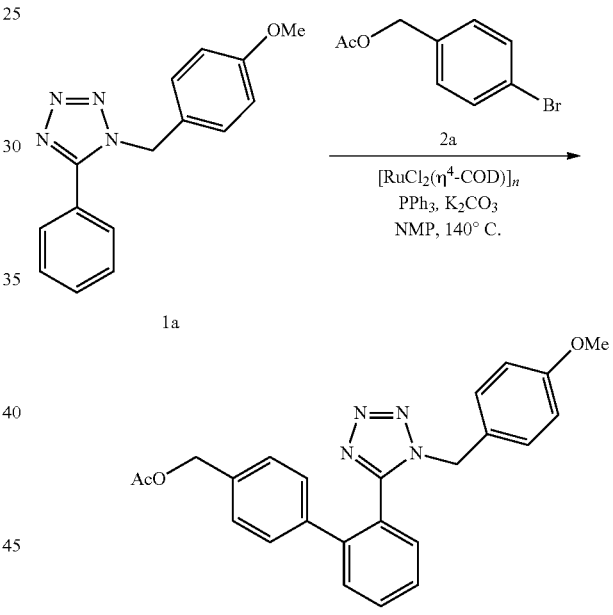

Under an argon atmosphere, into a 50 mL three-neck flask were charged 1-(4-methoxybenzyl)-5-phenyltetrazole (compound 1a, 160 mg, 0.60 mmol), p-bromobenzyl acetate (compound 2a, 345 mg, 1.5 mmol), dichloro(1,5-cyclooctadiene) ruthenium(II) polymer (16.9 mg, 0.06 mmol (monomer conversion)), triphenylphosphine (31.8 mg, 0.12 mmol), potassium carbonate (333 mg, 2.4 mmol) and dry N-methyl-2-pyrrolidone (1.2 ml), and the mixture was reacted at 140° C. for 2 hr. The completion of the reaction was confirmed by TLC (eluent: ethyl acetate/hexane=1/1). To the reaction mixture was added ethyl acetate (18 mL), and the mixture was filtered. The insoluble material was washed with ethyl acetate (9 mL), and the filtrate and the washing were combined. The solution was dried over magnesium sulfate, and concentrated to give a crude product (504 mg, yield 202%) as a dark green liquid. The yield of compound 3a in the crude product was quantified by HPLC, and it was (154 mg, yield 62%). Then, the crude product (419 mg) was purified by silica gel column chromatography (ethyl acetate/hexane=1/4) to give compound 3a (131 mg, yield 63%) as a yellow oil.

$^1$H-NMR (400 MHz, CDCl$_3$) δ=2.13 (3H, s), 3.73 (3H, s), 4.75 (2H, s), 5.08 (2H, s), 6.64-6.72 (4H, m), 7.10-7.15 (2H, m), 7.24-7.29 (2H, m), 7.35 (1H, dd, J=7.6, 1.2), 7.43-7.48 (1H, m), 7.57 (1H, dd, J=8.0, 0.8), 7.62-7.68 (1H, m).

$^{13}$C-NMR (400 MHz, CDCl$_3$) δ=122.45, 124.75, 135.57, 138.35, 140.85, 153.92, 159.29, 170.31 (8s), 113.78, 127.65, 128.18, 128.52, 129.07, 130.00, 130.90, 131.27 (8d), 50.37, 65.40 (2t), 20.94, 55.10 (2q).

IR(KBr) ν(cm$^{-1}$):1612, 1740

EIMS (m/z):414 (M$^+$)

Step 2

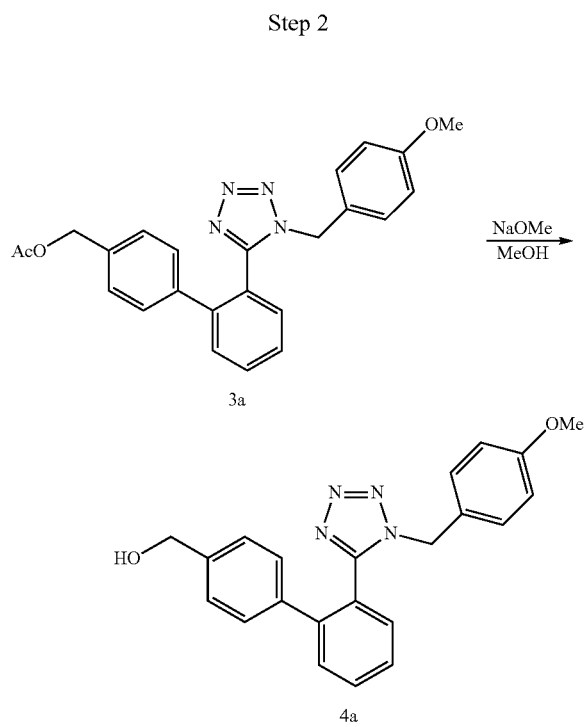

Into a 50 mL pear shape flask were charged compound 3a (0.268 g, 0.65 mmol), methanol (15 mL) and 28% sodium methoxide methanol solution (0.125 g, 0.65 mmol), and the mixture was reacted for 1.5 hr at room temperature. The disappearance of the starting material was confirmed by TLC (eluent: ethyl acetate/hexane=1/1). After completion of the reaction, the solvent was evaporated to give a crude product (0.271 g) as an orange oil. The obtained crude product was purified by silica gel column chromatography (ethyl acetate/hexane=1/2) to give compound 4a (0.151 g, yield 63%) as a yellow oil.

$^1$H-NMR (400 MHz, CDCl$_3$) δ=3.72 (3H, s), 4.68 (2H, s), 4.74 (2H, s), 6.63-6.72 (4H, m), 7.08-7.12 (2H, m), 7.24-7.29 (2H, m), 7.33 (1H, dd, J=7.6, 1.2), 7.41-7.46 (1H, m), 7.57 (1H, dd, J=8.0, 1.2), 7.61-7.67 (1H, m).

$^{13}$C-NMR (400 MHz, CDCl$_3$) δ=122.48, 124.92, 137.68, 140.79, 141.21, 154.16, 159.36 (7s), 113.88, 127.13, 127.61, 128.51, 129.19, 130.09, 131.01, 131.37 (8d), 50.17, 64.44 (2t), 55.24 (1q).

IR(KBr) ν(cm$^{-1}$):1612

EIMS (m/z):372 (M$^+$)

Step 3

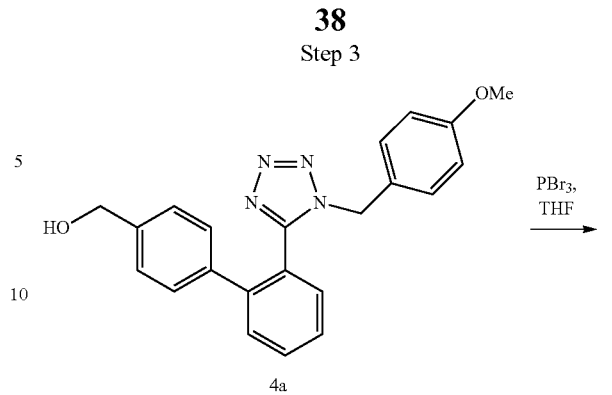

Into a 100 mL pear shape flask were charged compound 4a (0.891 g, 2.39 mmol) and THF (81.7 ml), phosphorus tribromide (1.30 g, 4.80 mmol) was added dropwise thereto at 0° C. over 1.5 hr, and the mixture was stirred at room temperature for 4 hr. The completion of the reaction was confirmed by TLC (eluent: ethyl acetate/hexane=1/1). The reaction mixture was poured into water (817 mL), and the mixture was extracted with ethyl acetate (653 mL). The organic layer was washed with water (490 mL×3), dried over sodium sulfate, and concentrated to give a crude product (2.47 g) as a yellow oil. The obtained crude product was purified by silica gel column chromatography (ethyl acetate/hexane=1/2) to give compound 5a (1.09 g, yield 105%) as a yellow oil.

$^1$H-NMR (400 MHz, CDCl$_3$) δ=3.73 (3H, s), 4.46 (2H, s), 4.75 (2H, s), 6.64-6.73 (4H, m), 7.07-7.13 (2H, m), 7.28-7.33 (2H, m), 7.34-7.38 (1H, m), 7.44-7.49 (1H, m), 7.55-7.59 (1H, m), 7.62-7.68 (1H, m).

$^{13}$C-NMR (400 MHz, CDCl$_3$) δ=122.69, 124.87, 137.54, 138.72, 140.83, 154.02, 159.50 (7s), 113.99, 127.92, 128.92, 129.26, 129.41, 130.11, 131.14, 131.45 (8d), 32.72, 50.57 (2t), 55.31 (1q).

IR(KBr) ν(cm$^{-1}$):1611

EIMS (m/z):434 (M$^+$)

Example 2

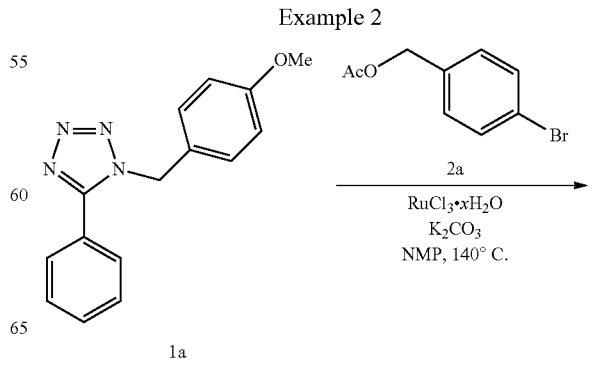

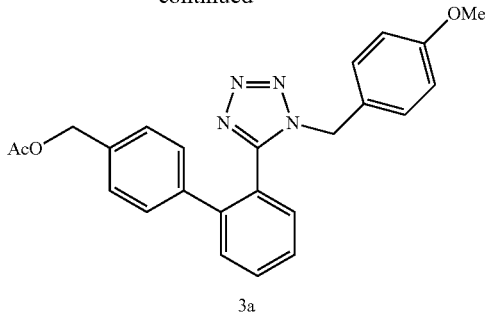

3a

A mixture of 1-(p-methoxybenzyl)-5-phenyl-1H-tetrazole (compound 1a, 151 mg, 0.567 mmol), potassium carbonate (157 mg, 1.13 mmol), ruthenium(III) chloride hydrate (14.4 mg, 11.8 mg (RuCl₃ conversion), 57.0 μmol), p-bromobenzyl acetate (compound 2a, 156 mg, 0.681 mmol) and N-methyl-2-pyrrolidone (1.1 mL) was heated at 120° C. for 16 hr under a nitrogen atmosphere. The reaction was monitored by HPLC. The reaction mixture was cooled, ethyl acetate (4 mL) was added thereto, and the mixture was filtrated to give the filtrate containing compound 3a. The content of compound 3a in the filtrate was quantified by HPLC, and it was 30.0 mg (12.8%).

Example 3

Step 1

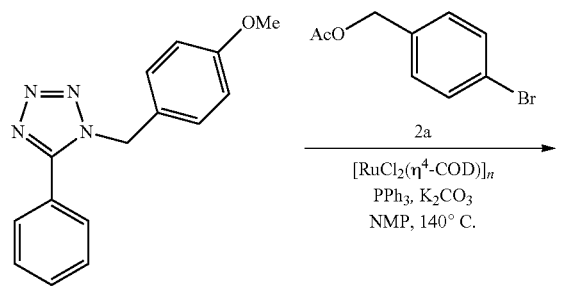

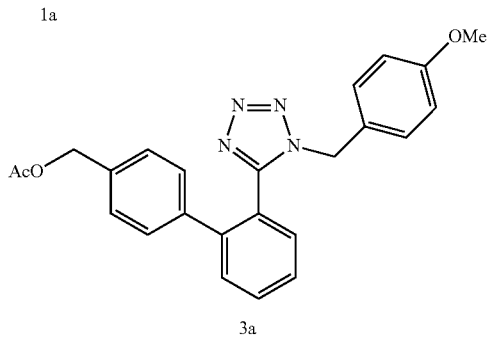

3a

Under an argon atmosphere, into a 100 mL four-neck flask were charged 1-(4-methoxybenzyl)-5-phenyltetrazole (compound 1a, 8.522 g, 32.0 mmol), p-bromobenzyl acetate (compound 2a, 9.496 g, 41.5 mmol), [RuCl₂(η⁴-COD)]ₙ (0.897 g, 3.20 mmol (10 mol %)), triphenylphosphine (1.679 g, 6.40 mmol), potassium carbonate (8.845 g, 64.0 mmol) and dry NMP (64 mL), and the mixture was stirred at 140° C. for 4 hr. Ethyl acetate (200 mL) was added thereto, and the mixture was filtered. The organic layer was washed twice with 10% brine (50 mL), dried over magnesium sulfate, and concentrated to give a brown solution (19.96 g, crude yield 150.5%). The crude product containing compound 3a was used for the next step without purification.

Step 2

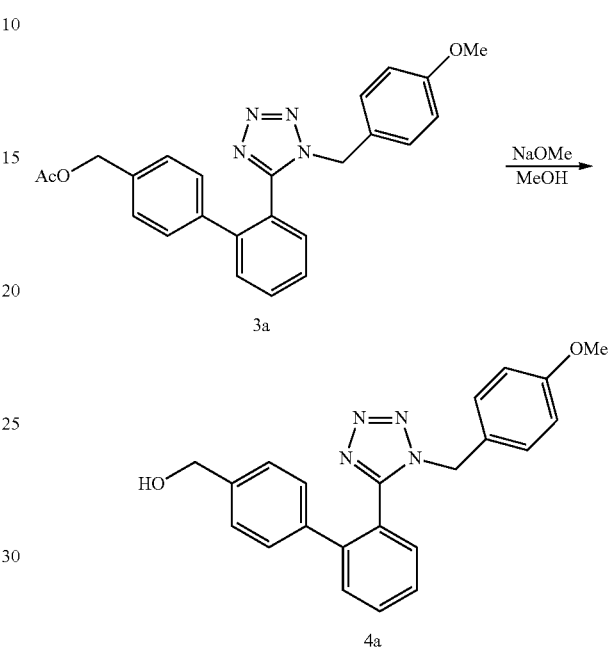

Into a 200 mL flask were charged compound 3a (19.92 g (crude product)), methanol (160 mL) and 28% sodium methoxide methanol solution (3.086 g, 0.8643 g (amount of sodium methoxide), 16.0 mmol), and the mixture was stirred at room temperature for 45 min. The completion of the reaction was confirmed by TLC (eluent: ethyl acetate/hexane=1/1). After completion of the reaction, the solvent was evaporated, and chloroform (160 mL) was added to the residue. The mixture was washed with 10% brine (40 mL×2), and the aqueous layer was extracted with chloroform (40 mL). The organic layers were combined, and dried over magnesium sulfate, and the solvent was evaporated to give a brown liquid (25.63 g, crude yield 143%). The crude product containing compound 4a was used for the next step without purification.

Step 3

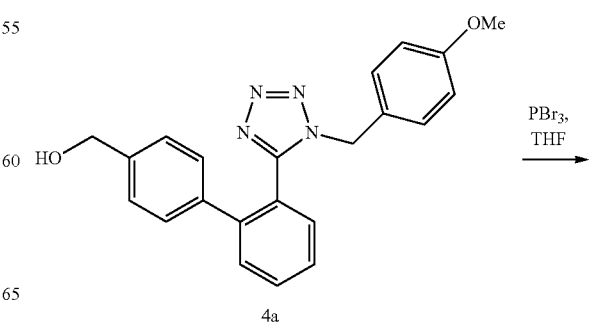

-continued

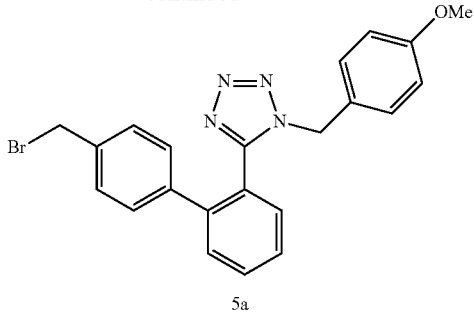

5a

Into a 200 mL four-neck flask were charged compound 4a (25.63 g (crude product)) and THF (160 mL), and phosphorus tribromide (17.45 g, 64.5 mmol) was added dropwise thereto at 0° C. for 1 hr. The mixture was stirred at room temperature for 2 hr. The completion of the reaction was confirmed by TLC (eluent: ethyl acetate/hexane=1/1). After completion of the reaction, the solution was poured into water (80 mL), and the mixture was extracted with ethyl acetate (80 mL×2). The organic layer was washed with 10% brine (40 mL×2), and dried over magnesium sulfate, and the solvent was evaporated to give a yellow oil (19.62 g, crude yield 141%). The oil was purified by silica gel column chromatography (ethyl acetate/hexane=1/3-1/2) to give compound 5a (5.89 g, yield 42% from compound 1a) as a yellow oil.

$^1$H-NMR (400 MHz, CDCl$_3$) δ=3.73 (3H, s), 4.46 (2H, s), 4.75 (2H, s), 6.64-6.73 (4H, m), 7.07-7.13 (2H, m), 7.28-7.33 (2H, m), 7.34-7.38 (1H, m), 7.44-7.49 (1H, m), 7.55-7.59 (1H, m), 7.62-7.68 (1H, m).

$^{13}$C-NMR (400 MHz, CDCl$_3$) δ=122.69, 124.87, 137.54, 138.72, 140.83, 154.02, 159.50 (7s), 113.99, 127.92, 128.92, 129.26, 129.41, 130.11, 131.14, 131.45 (8d), 32.72, 50.57 (2t), 55.31 (1q).

IR(KBr) ν(cm$^{-1}$):1611
EIMS (m/z):434 (M$^+$)

Example 4

Step 1

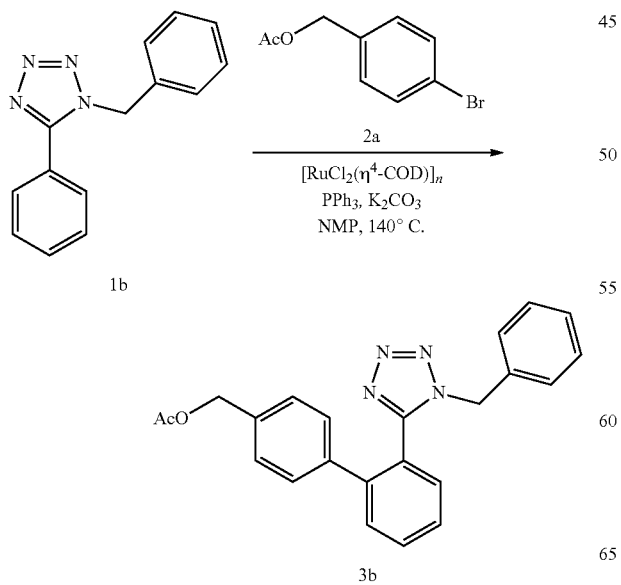

A mixture of triphenylphosphine (4.81 g, 18.3 mmol), 1-benzyl-5-phenyl-1H-tetrazole (compound 1b, 43.3 g, 183 mmol), potassium carbonate (50.7 g, 367 mmol), dichloro(1,5-cyclooctadiene)ruthenium(II) polymer (2.57 g, 9.17 mmol (monomer conversion)), p-bromobenzyl acetate (compound 2a, 62.9 g, 274 mmol) and N-methyl-2-pyrrolidone (366 mL) was stirred at 140° C. for 5 hr under a nitrogen atmosphere. The reaction was monitored by HPLC. The reaction mixture was cooled, mixed with ethyl acetate (1000 mL), and filtered, and the insoluble material was washed with ethyl acetate (about 80 mL). The filtrate was poured into 10% brine (254 mL), and the organic layer was separated. The organic layer was washed with 10% brine (254 mL), dried over magnesium sulfate (50 g), and at concentrated under reduced pressure at 40° C. or lower to give the crude product (161 g, 229% of the theoretical yield) of compound 3b as a dark brown oil. This was used for the next step without purification.

IR (neat): 1741 (0=O), 1603 cm$^{-1}$.
$^1$H-NMR (CDCl$_3$): δ=7.63 (td, J=7.6, 1.4 Hz, 1H, biphenyl), 7.57 (dd, J=7.6, 1.4 Hz, 1H, biphenyl), 7.44 (td, J=7.6, 1.4 Hz, 1H, biphenyl), 7.34 (dd, J=7.6, 1.4 Hz, 1H, biphenyl), 7.27 (d, J=8.6 Hz, 2H, o-Ph of Bn), 7.22 (t, J=8.6 Hz, 1H, p-Ph of Bn), 7.16 (t, J=8.6 Hz, 2H, m-Ph of Bn), 7.13 (d, J=7.2 Hz, 2H, biphenyl), 6.76 (d, J=7.2 Hz, 2H, biphenyl), 5.09 (s, 2H, CH$_2$O), 4.82 (s, 2H, CH$_2$N), 2.11 (s, 3H, Me).
$^{13}$C-NMR (CDCl$_3$): δ=171 (C=O), 155 (tetrazole), 141, 139, 136, 133 (quaternary Ar), 132, 131, 130, 129, 129, 128, 128 (CH), 122 (quaternary Ar), 66 (CH$_2$O), 51 (CH$_2$ of Bn), 21 (CH$_3$).
MS:385 (MH$^+$)

Step 2

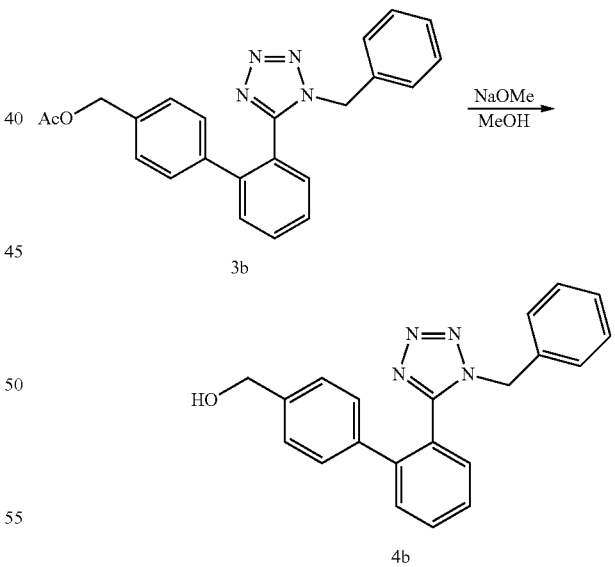

To a solution of crude [2'-(1-benzyl-1H-tetrazol-5-yl)biphenyl-4-yl]methyl acetate (150 g (crude product), 65.4 g (the content of compound 3b in the crude product), 0.170 mol) in methanol (748 mL) was added dropwise 28% sodium methoxide methanol solution (16.4 g, 85 mmol) at 18-19° C., and the dropping funnel was washed with methanol (2.9 g). The reaction was confirmed by TLC (eluent: toluene/ethyl acetate (4:1)) and HPLC. The reaction mixture was stirred at about 20° C. for 1 hr, and concentrated under reduced pressure at 40° C. or lower. The concentrate was mixed with chloroform (791 mL) and 24% brine (186 g). The organic layer was separated, washed with 24% brine (186 g), dried over magnesium sulfate (36 g), and filtered through activated clay (GALLEON EARTH NV, 50 g), and the clay was washed with chloroform (about 50 mL). The filtrate was concentrated under reduced pressure to give a crude product of compound 4b (130 g, 222% of the theoretical yield) as a dark brown oil. The crude product was used for the next step without purification.

IR (neat): 3397 (OH), 1603 $cm^{-1}$.

$^1$H-NMR (CDCl$_3$): δ=7.64 (td, J=7.6, 1.6 Hz, 1H, biphenyl), 7.57 (dd, J=7.6, 1.6 Hz, 1H, biphenyl), 7.43 (td, J=7.6, 1.6 Hz, 1H, biphenyl), 7.34 (dd, J=7.6, 1.6 Hz, 1H, biphenyl), 7.29 (d, J=8.4 Hz, 2H, Ph of Bn), 7.21 (t, J=8.4 Hz, 1H, Ph of Bn), 7.16 (t, J=8.4 Hz, 2H, Ph of Bn), 7.12 (d, J=7.5 Hz, 2H, biphenyl), 6.78 (d, J=7.5 Hz, 2H, biphenyl), 4.82 (s, 2H, CH$_2$N), 4.70 (d, J=5.7 Hz, 2H, CH$_2$O), 1.81 (t, J=5.7 Hz, 1H, OH).

$^{13}$C-NMR (CDCl$_3$): δ=155 (tetrazole), 141, 141, 138, 133 (quaternary Ar), 132, 131, 130, 129, 129, 128, 127 (CH), 122 (quaternary Ar), 64 (CH$_2$O), 51 (CH$_2$ of Bn).

MS: 343 (MH$^+$)

Step 3

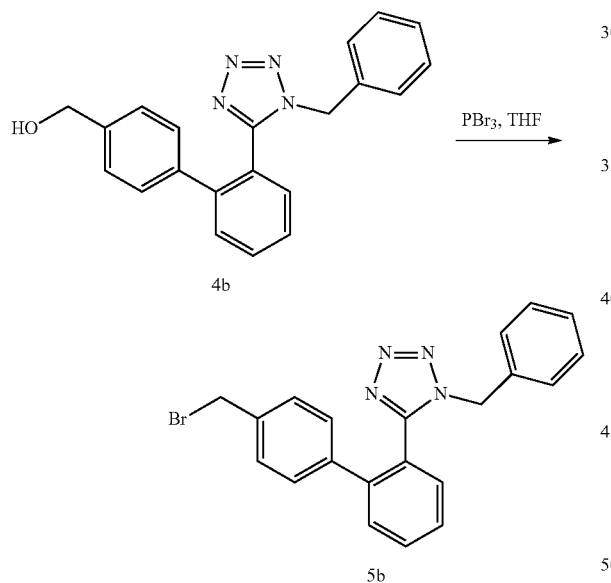

To a mixture of crude [2'-(1-benzyl-1H-tetrazol-5-yl)biphenyl-4-yl]methanol (118 g (crude product), 52.9 g (the content of compound 4b in the crude product), 0.154 mol) and THF (710 mL) was added dropwise phosphorus tribromide (62.7 g, 0.232 mol) over 1 hr at −9−−4° C. under a nitrogen atmosphere, and the dropping funnel was washed with THF (7 mL). The reaction was confirmed by TLC (eluent: toluene/ethyl acetate (4:1) and ethyl acetate/hexane (1:1)). The reaction mixture was warmed to 12° C., poured into water (360 mL) at 26° C. or lower, and extracted with ethyl acetate (360 mL). The aqueous layer was extracted with ethyl acetate (360 mL), and the combined organic layers were washed twice with 10% brine (190 g), dried over magnesium sulfate (34 g), and concentrated under reduced pressure at 40° C. or lower to give a crude product (96.5 g, 154% of the theoretical yield).

The crude product was purified by silica gel column chromatography (eluent: toluene/ethyl acetate (100:0-1:1)) to give the following three dark brown oils.

(A): 0.17 g, 0.3% of the theoretical yield; extremely small amount of less polar spot, besides compound 5b (B): 16.6 g, 26.5% of the theoretical yield; almost compound 5b alone (C): 9.99 g, 9.6% of the theoretical yield; small amount of highly-polar 2 spots, besides compound 5b The oil of the above-mentioned (B) (compound 5b) was subjected to NMR measurement.

IR (neat): 1603 $cm^{-1}$ $^1$H-NMR (CDCl$_3$): δ=7.65 (td, J=7.5, 1.5 Hz, 1H, biphenyl), 7.57 (dd, J=7.5, 1.5 Hz, 1H, biphenyl), 7.45 (td, J=7.9, 1.4 Hz, 1H, biphenyl), 7.35 (dd, J=7.9, 1.4 Hz, 1H, biphenyl), 7.31 (d, J=8.2 Hz, 2H, o-Ph), 7.22 (t, J=8.2 Hz, 1H, p-Ph), 7.17 (t, J=8.2 Hz, 2H, m-Ph), 7.10 (2H, J=8.2 Hz, 2H, biphenyl), 6.77 (2H, J=8.2 Hz, 2H, biphenyl), 4.82 (s, 2H, CH$_2$N), 4.46 (s, 2H, CH$_2$Br).

$^{13}$C-NMR (CDCl$_3$): δ=154 (tetrazole), 141 (quaternary Ar), 139 (quaternary Ar), 138 (quaternary Ar), 133 (quaternary Ar), 132 (CH of Ar), 131 (CH of Ar), 130 (CH of Ar), 129 (CH of Ar), 129 (CH of Ar), 129 (CH of Ar), 128 (CH of Ar), 128 (CH of Ar), 122 (quaternary Ar), 51 (CH$_2$N), 32 (CH$_2$Br).

MS: 405 (MH$^+$)

Example 5

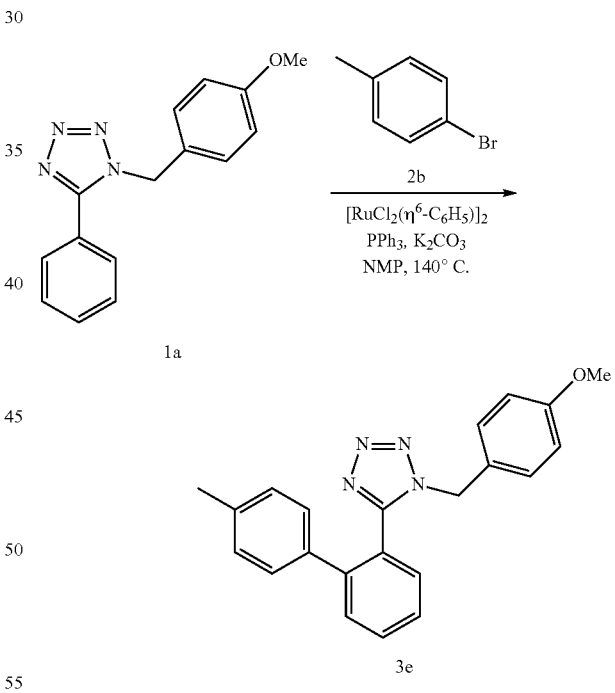

Under an argon atmosphere, into a 50 mL three-neck flask were charged 1-(4-methoxybenzyl)-5-phenyltetrazole (compound 1a, 799.0 mg, 3 mmol), 4-bromotoluene (compound 2b, 1.2803 g, 7.5 mmol), [RuCl$_2$(η$^6$-C$_6$H$_6$)]$_2$ (75.3 mg, 0.15 mmol (5 mol %)), triphenylphosphine (157.0 mg, 0.6 mmol), potassium carbonate (1.6601 g, 12 mmol) and dry NMP (6.0 ml), and the mixture was reacted at 140° C. for 2 hr. After completion of the reaction, the mixture was diluted with ethyl acetate (90 ml), the insoluble material was filtered off, and washed with ethyl acetate (45 mL). The filtrate and washing were combined, washed with brine, and dried over magnesium sulfate, and the solvent was evaporated to give a crude product (1.53 g, yield 143%) as a dark green liquid. The crude product was purified by silica gel column chromatography (hexane/ethyl acetate=4/1) to give 1-(4-methoxybenzyl)-5-(4'-methylbiphenyl-2-yl)tetrazole (compound 3e, 640 mg, yield 60%) as a yellowish white solid.

$^1$H-NMR (400 MHz, CDCl$_3$) δ=2.34 (3H, s), 3.72 (3H, s), 4.70 (2H, s), 6.61-6.73 (4H, m), 7.00-7.12 (4H, m), 7.30-7.45 (2H, m), 7.53-7.65 (2H, m).

$^{13}$C-NMR (400 MHz, CDCl$_2$) δ=122.61, 125.08, 135.76, 137.82, 141.42, 154.31, 159.40 (7s), 113.87, 127.40, 128.32, 129.25, 129.52, 129.99, 131.11, 131.30 (8d), 50.44 (1t), 21.23, 55.25 (3q).

IR(KBr) ν(cm$^{-1}$):1612
EIMS (m/z):356 detector UV 225 nm
temperature 40° C.
melting point: 117-118° C.
IR (KBr): 1735, 1603 cm$^{-1}$ $^1$H-NMR (DMSO-d$_6$): δ=7.74 (td, J=7.7, 1.4 Hz, 1H), 7.61-7.58% (m, 3H), 7.28 (d, J=8.2 Hz, 2H), 7.27 (td, J=7.4, 1.4 Hz, 1H), 7.00 (d, 2H, J=8.2 Hz, 2H), 6.91 (dd, J=7.4, 1.4 Hz, 1H), 6.90 (d, J=7.4 Hz, 1H), 6.81 (t, J=7.4 Hz, 1H), 5.06 (s, 2H), 4.98 (s, 2H), 3.51 (s, 3H), 2.08 (s, 3H).

$^{13}$C-NMR (DMSO-d$_6$): δ=170, 156, 154, 141, 138, 136, 131, 131, 130, 130, 128, 128, 128, 122, 121, 120, 111, 65, 55, 46, 21.

MS: m/z=415 (MH$^+$)

Example 6

Example 7

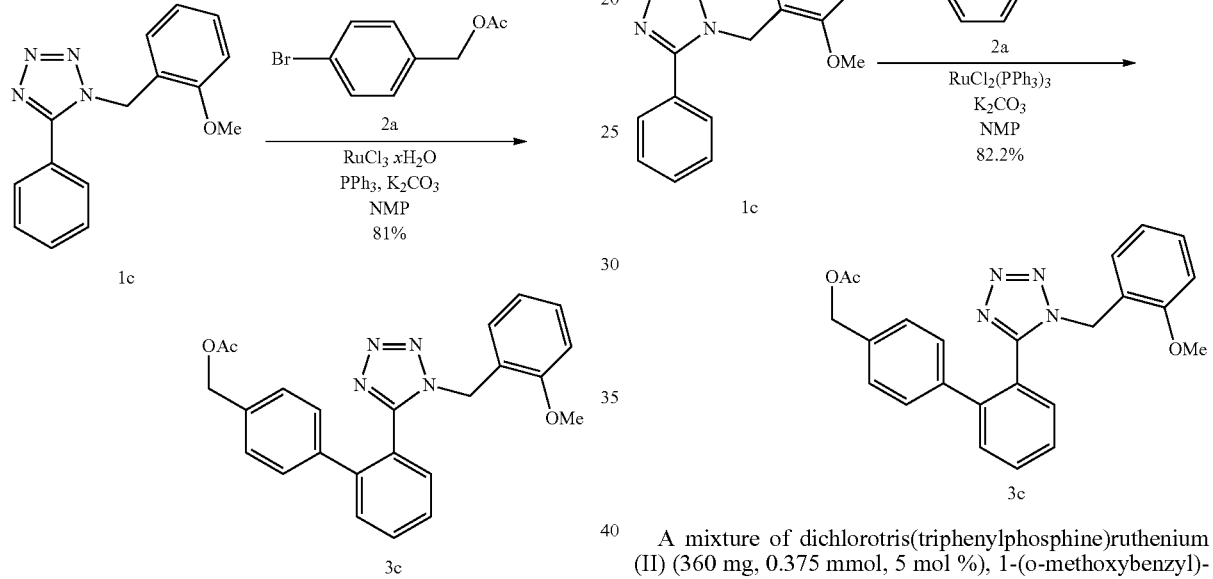

A mixture of ruthenium(III) chloride hydrate (Ru 40.01%; 5.8 mg, 4.8 mg (RuCl$_3$), 23 μmol, 1.3 mol %), triphenylphosphane (10.4 mg, 39.7 μmol), 1-(o-methoxybenzyl)-5-phenyl-1H-tetrazole (compound 1c, 481 mg, 1.81 mmol), potassium carbonate (499 mg, 3.61 mmol), p-bromobenzyl acetate (compound 2a, 455 mg, 1.99 mmol) and N-methyl-2-pyrrolidone (1.9 mL) was heated with stirring for 10 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 mL). The resultant product (compound 3c) in the obtained filtrate (19.6 g) was quantified by HPLC. The net weight of compound 3c was 607 mg (81%).

HPLC measurement condition:
column Inertsil ODS—3.2 μm, 3.0×50 mm
mobile phase A MeCN/30 mM KH$_2$PO$_4$(11:9)
mobile phase B 0.1 w/v % phosphoric acid
total flow 0.5 mL/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)

A mixture of dichlorotris(triphenylphosphine)ruthenium (II) (360 mg, 0.375 mmol, 5 mol %), 1-(o-methoxybenzyl)-5-phenyl-1H-tetrazole (compound 1c, 2.00 g, 7.51 mmol), potassium carbonate (2.09 g, 15.1 mmol), p-bromobenzyl acetate (compound 2a, 2.54 g, 11.1 mmol) and N-methyl-2-pyrrolidone (15.0 mL) was heated with stirring under a nitrogen atmosphere. The inside temperature was maintained at about 140° C. for 5 hr, and the mixture was allowed to cool to room temperature. The reaction was monitored by HPLC. To the reaction mixture was added ethyl acetate (45 mL), and the mixture was filtered. The insoluble material was washed successively with ethyl acetate (10 mL) and the filtrate was washed with 20% brine (40 ml), and dried over magnesium sulfate (1.1 g). The magnesium sulfate was filtered off, and washed with ethyl acetate (about 10 mL). The resultant product (compound 3c) in the obtained filtrate (58.6 g) was quantified by HPLC, and the net weight of compound 3c was 2.56 g (82.2%).

HPLC measurement condition:
column Inertsil ODS—3.2 μm, 3.0×50 mm
mobile phase A MeCN/30 mM KH$_2$PO$_4$ (11:9)
mobile phase B 0.1 w/v % phosphoric acid
total flow 0.5 mL/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)

detector UV 225 nm
temperature 40° C.

Example 8

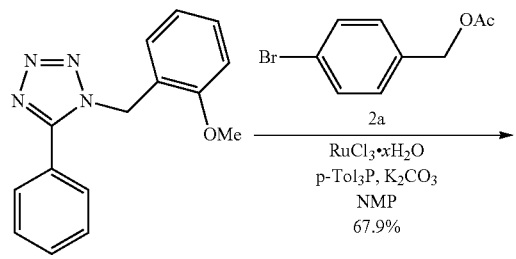

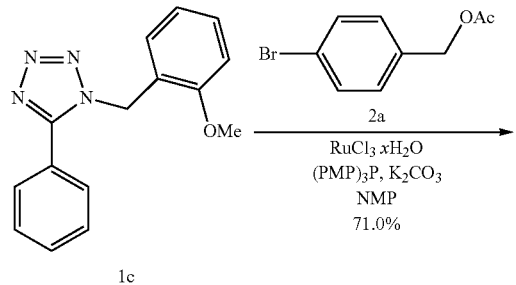

A mixture of ruthenium(III) chloride hydrate (Ru 40.01%; 5.2 mg, 4.3 mg (RuCl₃), 21 µmol, 1.3 mol %), tri(p-tolyl)phosphane (11.0 mg, 36.1 mmol), 1-(o-methoxybenzyl)-5-phenyl-1H-tetrazole (compound 1c, 439 mg, 1.65 mmol), potassium carbonate (455 mg, 3.29 mmol), p-bromobenzyl acetate (compound 2a, 415 mg, 1.81 mmol) and N-methyl-2-pyrrolidone (1.8 mL) was stirred with heating for 11 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 mL). The resultant product (compound 3c) in the obtained filtrate (19.4 g) was quantified by HPLC, and the net weight of compound 3c was 464 mg (67.9%).

HPLC measurement condition:
column Inertsil ODS—3.2 µm, 3.0×50 mm
mobile phase A MeCN/30 mM KH₂PO₄ (11:9)
mobile phase B 0.1 w/v % phosphoric acid
total flow 0.5 ml/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)
detector UV 225 nm
temperature 40° C.

Example 9

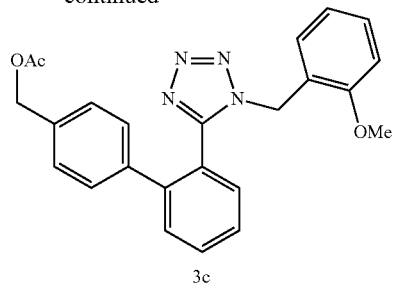

A mixture of ruthenium(III) chloride hydrate (Ru 40.01%; 5.1 mg, 4.2 mg (RuCl₃), 20 µmol, 1.3 mol %), tri(p-methoxyphenyl)phosphane (12.5 mg, 35.5 µmol), 1-(o-methoxybenzyl)-5-phenyl-1H-tetrazole (compound 1c, 430 mg, 1.61 mmol), potassium carbonate (446 mg, 3.23 mmol), p-bromobenzyl acetate (compound 2a, 407 mg, 1.78 mmol) and N-methyl-2-pyrrolidone (1.7 mL) was heated with stirring for 12 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 mL). The resultant product (compound 3c) in the obtained filtrate (19.3 g) was quantified by HPLC, and the net weight of compound 3c was 475 mg (71.0%).

HPLC measurement condition:
column Inertsil ODS—3.2 µm, 3.0×50 mm
mobile phase A MeCN/30 mM KH₂PO₄ (11:9)
mobile phase B 0.1 w/v % phosphoric acid
total flow 0.5 mL/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)
detector UV 225 nm
temperature 40° C.

Example 10

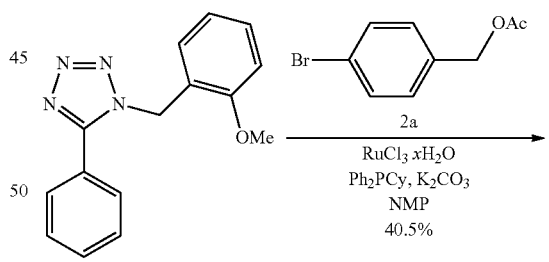

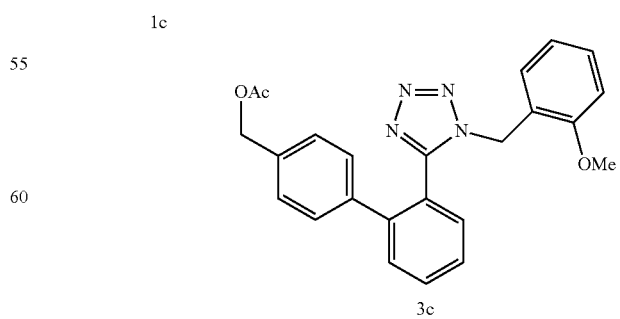

A mixture of ruthenium(III) chloride hydrate (Ru 40.01%; 5.5 mg, 4.5 mg (RuCl₃), 22 µmol, 1.2 mol %), cyclohexyldiphenylphosphane (10.2 mg, 38.0 μmol), 1-(o-methoxybenzyl)-5-phenyl-1H-tetrazole (compound 1c, 464 mg, 1.74 mmol), potassium carbonate (482 mg, 3.48 mmol), p-bromobenzyl acetate (compound 2a, 439 mg, 1.92 mmol) and N-methyl-2-pyrrolidone (1.9 mL) was heated with stirring for 12 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 mL). The resultant product (compound 3c) in the obtained filtrate (19.5 g) was quantified by HPLC, and the net weight of compound 3c was 292 mg (40.5%).

HPLC measurement condition:
column Inertsil ODS—3.2 μm, 3.0×50 mm
mobile phase A MeCN/30 mM $KH_2PO_4$ (11:9)
mobile phase B 0.1 w/v % phosphoric acid
total flow 0.5 mL/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)
detector UV 225 nm
temperature 40° C.

Example 11

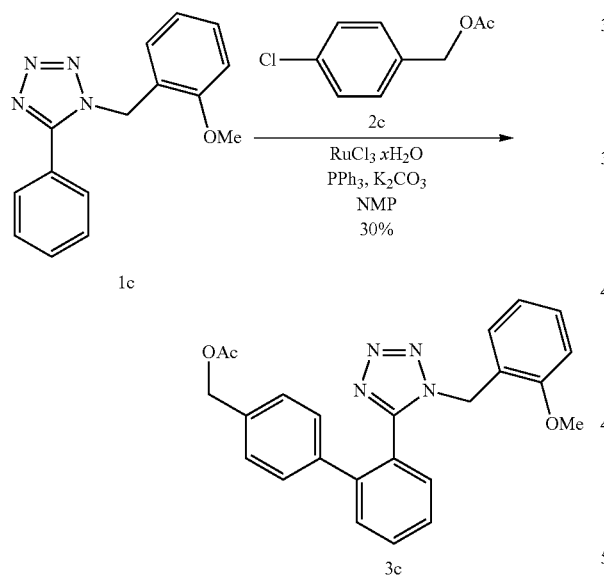

A mixture of ruthenium(III) chloride hydrate (Ru 40.01%; 5.4 mg, 4.4 mg ($RuCl_3$), 21 μmol, 1.3 mol %), triphenylphosphane (11.2 mg, 42.7 μmol), 1-(o-methoxybenzyl)-5-phenyl-1H-tetrazole (compound 1c, 455 mg, 1.71 mmol), potassium carbonate (472 mg, 3.42 mmol), p-chlorobenzyl acetate (compound 2c, 347 mg, 1.88 mmol) and N-methyl-2-pyrrolidone (1.8 mL) was heated with stirring for 13 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 ml). The resultant product (compound 3c) in the filtrate (19.8 g) was quantified by HPLC, and the net weight of compound 3c was 213 mg (30.0%).

HPLC measurement condition:
column Inertsil ODS—3.2 μm, 3.0×50 mm
mobile phase A MeCN/30 mM $KH_2PO_4$ (11:9)
mobile phase B 0.1 w/v % phosphoric acid
total flow 0.5 mL/min
gradient cycle: 0 min (SOLUTION A/SOLUTION B=80/20), 5 min (SOLUTION A/SOLUTION B=100/0), 40 min (SOLUTION A/SOLUTION B=100/0), 43 min (SOLUTION A/SOLUTION B=80/20)
detector UV 225 nm
temperature 40° C.

Example 12

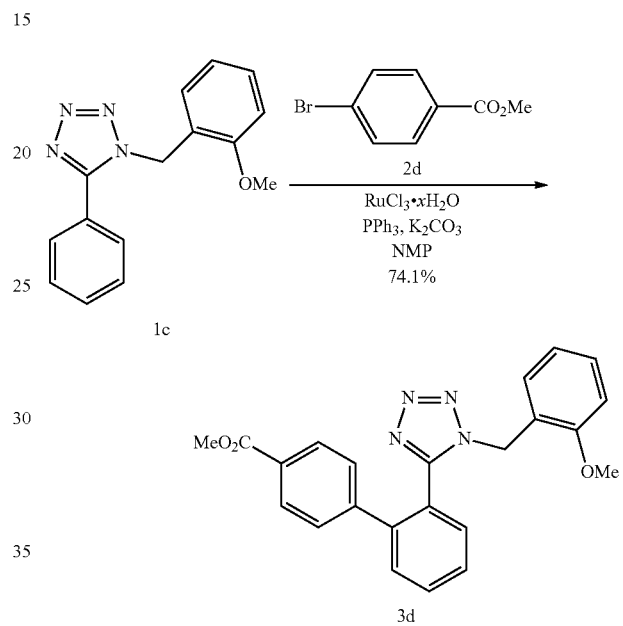

A mixture of ruthenium(III) chloride hydrate (Ru 40.01%; 6.8 mg, 5.6 mg ($RuCl_3$), 27 μmol, 1.3 mol %), triphenylphosphane (14.0 mg, 53.4 μmol), 1-(o-methoxybenzyl)-5-phenyl-1H-tetrazole (compound 1c, 567 mg, 2.13 mmol), methyl p-bromobenzoate (compound 2d, 503 mg, 2.34 mmol), potassium carbonate (324 mg, 2.34 mmol) and N-methyl-2-pyrrolidone (2.0 mL) was heated with stirring for 12 hr in a bath at 140° C. under a nitrogen atmosphere. The reaction was monitored by HPLC. The reaction mixture was allowed to cool to room temperature, and ethyl acetate (10 mL) was added thereto. The mixture was filtered, and the insoluble material was washed with ethyl acetate (10 mL). The resultant product (compound 3d) in the obtained filtrate (20.3 g) was quantified by HPLC, and the net weight of compound 3d was 632 mg (74.1%).

HPLC measurement condition:
column Inertsil ODS—3.2 μm, 3.0×50 mm
mobile phase A MeCN/30 mM $KH_2PO_4$ (11:9)
mobile phase B 0.1 w/v % phosphoric acid
total flow 0.5 mL/min
gradient cycle: 0 min (SOLUTION A/SOLUTION B=70/30), 5 min (SOLUTION A/SOLUTION B=100/0), 35 min (SOLUTION A/SOLUTION B=100/0), 38 min (SOLUTION A/SOLUTION B=70/30)
detector UV 225 nm
temperature 40° C.
melting point: 72-75° C.
IR(KBr): 1735, 1719, 1610 $cm^{-1}$ ¹H-NMR (DMSO-d₆): δ=7.84 (d, J=8.4 Hz, 2H), 7.77 (m, 1H), 7.67-7.65 (m, 3H), 7.27 (td, J=8.4, 1.4 Hz, 1H), 7.11 (d, J=8.4 Hz, 2H), 6.97 (dd, J=8.4, 1.4 Hz, 1H), 6.90 (d, J=8.4 Hz, 1H), 6.81 (t, J=8.4 Hz, 1H), 5.03 (s, 2H), 3.85 (s, 3H), 3.50 (s, 3H).

MS: m/z=401 (MH⁺)

Example 13

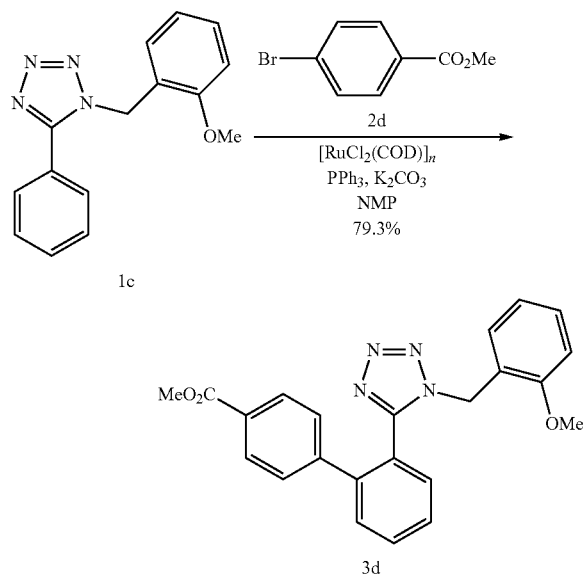

A mixture of poly[(η²,η²-cycloocta-1,5-diene)ruthenium-di-β-chloro] (10.2 mg, 36.4 μmol (monomer conversion), 5 mol %), triphenylphosphane (19.3 mg, 73.6 μmol), 1-(o-methoxybenzyl)-5-phenyl-1H-tetrazole (compound 1c, 194 mg, 0.729 mmol), methyl p-bromobenzoate (compound 2d, 236 mg, 1.10 mmol), potassium carbonate (203 mg, 1.47 mmol) and N-methyl-2-pyrrolidone (1.5 mL) was heated with stirring for 9 hr in a bath at 140° C. under a nitrogen atmosphere. The reaction was monitored by HPLC, and ethyl acetate (5.0 mL) was added thereto. The mixture was filtered, and the insoluble material was washed successively with ethyl acetate (7.0 mL), and 20% brine (4.0 mL), and the aqueous layer was extracted with ethyl acetate (10.0 mL). The combined organic layers were dried over magnesium sulfate (1.0 g), and activated carbon (Yuki A (dry) (trade name), manufactured by SERACHEM Co. Ltd.; 0.10 g) was added thereto. The mixture was stirred for 30 min, and filtered, and the activated carbon was washed with ethyl acetate (10 mL). The filtrate was concentrated under reduced pressure in a bath at 40° C. to give crude product (10.6 g). Compound 3d in the crude product was quantified by HPLC, and the net weight was 232 mg (79.3%).

HPLC measurement condition:
column Inertsil ODS—3.2 μm, 3.0×50 mm
mobile phase A MeCN/30 mM KH₂PO₄ (11:9)
mobile phase B 0.1 w/v % phosphoric acid total flow 0.5 mL/min
gradient cycle: 0 min (SOLUTION A/SOLUTION B=70/30), 5 min (SOLUTION A/SOLUTION B=100/0), 35 min (SOLUTION A/SOLUTION B=100/0), 38 min (SOLUTION A/SOLUTION B=70/30)
detector UV 225 nm
temperature 40° C.

Example 14

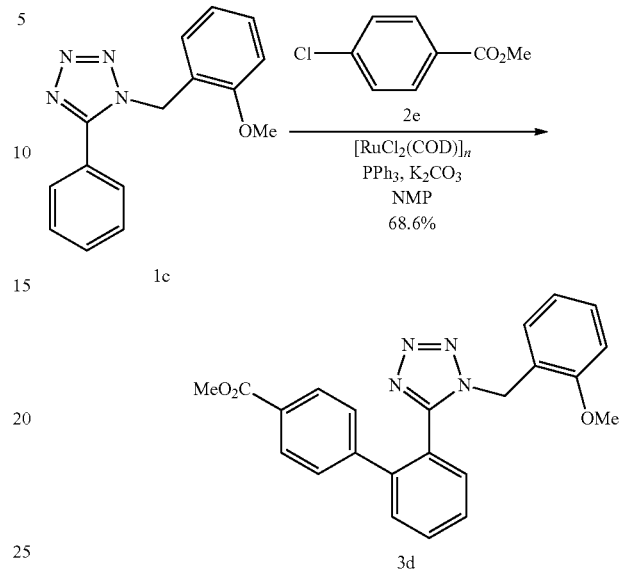

A mixture of poly [(η²,η²-cycloocta-1,5-diene)ruthenium-di-μ-chloro] (11.2 mg, 40.0 μmol (monomer conversion), 5 mol %), triphenylphosphane (21.1 mg, 80.4 μmol), 1-(o-methoxybenzyl)-5-phenyl-1H-tetrazole (compound 1c, 214 mg, 0.802 mmol), methyl p-chlorobenzoate (compound 2e, 205 mg, 1.20 mmol), potassium carbonate (222 mg, 1.61 mmol) and N-methyl-2-pyrrolidone (1.6 mL) was heated with stirring for 9 hr in a bath at 140° C. under a nitrogen atmosphere. The reaction was monitored by HPLC. The reaction mixture was allowed to cool to room temperature, and ethyl acetate (5.0 mL) was added thereto. The mixture was filtered, and the insoluble material was washed with ethyl acetate (6.4 mL). 10% brine (4.0 ml) was added thereto, and the organic layer was separated. The main resultant product was detected in the aqueous layer when the aqueous layer was monitored by TLC (eluent: hexane/ethyl acetate (1:1) and toluene/ethyl acetate (7:3)), and then the aqueous layer was extracted with ethyl acetate (5.0 mL). To the combined organic layers was added 20% brine, and the organic layer was separated. The main resultant product was detected in the aqueous layer when the aqueous layer was monitored by TLC (eluent: hexane/ethyl acetate (1:1)), and then the aqueous layer was extracted with ethyl acetate (5.0 mL). The combined organic layers were washed with saturated brine (5.0 mL), saturated brine (8.0 mL) was added thereto, and the organic layer was separated. The main resultant product was detected in the aqueous layer when the aqueous layer was monitored by TLC. The combined aqueous layers were extracted with ethyl acetate (10 mL). The combined organic layers were dried over magnesium sulfate (3.4 g), activated carbon (Yuki A (dry) (trade name), manufactured by SERACHEM Co. Ltd.; 0.10 g) was added thereto. The mixture was stirred for min, and filtered, and the activated carbon was washed with ethyl acetate (10 mL). The filtrate was concentrated under reduced pressure in a bath at 40° C. to give a crude product (9.54 g). The content of compound 3d obtained in the crude product was quantified by HPLC, and it was 73.9% (crude product 321 mg, compound 3d, 237 mg). The total amount (9.54 g) of the obtained crude product was purified by silica gel column chromatography (eluent: hexane/ethyl acetate (100:0-2:1)). The solvent was evaporated, and the solid was heated with ethyl acetate (2 mL) to dissolve a large part of the solid. Diisopropyl ether (8 mL) was added gradually thereto, and seed crystals were appropriately added thereinto. The mixture was cooled to −2° C., and the resulting solid was collected by filtration, washed with diisopropyl ether (8.5 mL), and dried at 40° C. or lower to give compound 3d (466 mg, 76.0% of the theoretical yield) as white crystals. The net weight of the obtained compound 3d was quantified by $^1$H-NMR spectrum (compound 3d/diisopropyl ether/ethyl acetate=90.3:5.8:3.9 (mass ratio)), and it was 421 mg (68.6%).

HPLC measurement condition:
column Inertsil ODS—3.2 μm, 3.0×50 mm
mobile phase A MeCN/30 mM $KH_2PO_4$ (11:9)
mobile phase B 0.1 w/v % phosphoric acid
total flow 0.5 mL/min
gradient cycle: 0 min (SOLUTION A/SOLUTION B=70/30), 5 min (SOLUTION A/SOLUTION B=100/0), 35 min (SOLUTION A/SOLUTION B=100/0), 38 min (SOLUTION A/SOLUTION B=70/30)
detector UV 225 nm
temperature 40° C.

Example 15

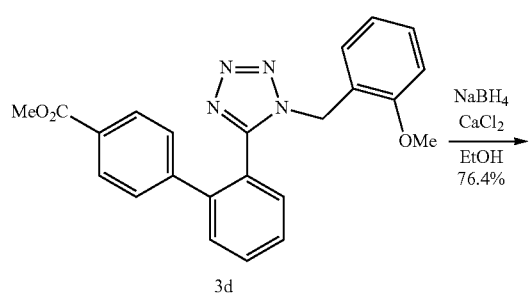

To calcium chloride (0.910 g) was added ethanol (99.5%; 7.85 g), and the mixture was heated to about 60° C. to dissolve the calcium chloride, and allowed to cool to room temperature to give a calcium chloride ethanol solution (10.4%; density 0.850 g/mL).

A mixture of methyl 2'-[1-(o-methoxybenzyl)-1H-tetrazol-5-yl]biphenyl-4-carboxylate (compound 3d, content 90.3%; 97.7 mg, net weight 88.3 mg, 0.220 mmol), the above-mentioned calcium chloride ethanol solution (10.4%; 0.166 mL, 141 mg, calcium chloride content 14.6 mg, 0.132 mmol) and ethanol (99.5%; 0.29 mL) was cooled in a bath at 5° C., sodium tetrahydroborate (10.0 mg, 0.264 mmol) was added thereto, and the mixture was stirred at room temperature for 1 hr under a nitrogen atmosphere. The reaction was monitored by TLC (eluent: toluene/ethyl acetate (2:1)). The reaction mixture was heated with stirring for 2.5 hr in a bath at 60° C., and allowed to cool to room temperature. To the reaction mixture was added calcium chloride ethanol solution (10.4%; 50 μL, 42 mg, calcium chloride content 4.4 mg, 40 mol), and the mixture was cooled in a bath at 8° C. Sodium tetrahydroborate (3.1 mg, 82 μmol) was added thereto, and the cold bath was taken off. The reaction mixture was heated in a bath at 60° C. for 2 hr, and cooled in a bath at 8° C. 10% Hydrochloric acid (0.15 mL, 159 mg) was added thereto, and the mixture was allowed to warm to room temperature. Water (1.0 mL) was added thereto, and the mixture was extracted three times with ethyl acetate (5.0 mL). The combined organic layers were washed successively with saturated aqueous sodium hydrogen carbonate solution (3.0 mL) and 20% brine (3.0 mL), dried over magnesium sulfate (0.5 g), and concentrated under reduced pressure at 30° C. or lower. To the obtained oil was added diisopropyl ether (1.0 mL), and the mixture was triturated to crystallize. Diisopropyl ether (2.0 mL) was added thereto, and the mixture was stirred for 30 min. The resulting solid was collected by filtration, washed with diisopropyl ether (1.0 mL), and dried under reduced pressure at 40° C. or lower to give compound 4c (62.7 mg, 76.4%).

melting point: 139-141° C.
IR(KBr): 3398, 1605 $cm^{-1}$
$^1$H-NMR (DMSO-$d_6$): δ=7.73 (td, J=7.8, 2.3 Hz, 1H), 7.60 (d, J=7.8 Hz, 1H), 7.59-7.55 (m, 2H), 7.26 (td, J=7.9, 1.6 Hz, 1H), 7.23 (d, J=8.2 Hz, 2H), 6.96 (d, J=8.2 Hz, 2H), 6.91 (dd, J=7.9, 1.6 Hz, 1H), 6.89 (d, J=7.9 Hz, 1H), 6.81 (t, J=7.9 Hz, 1H), 5.22 (t, J=5.9 Hz, 1H), 4.93 (s, 2H), 4.49 (d, J=5.9 Hz, 2H), 3.50 (s, 3H).
$^{13}$C-NMR (DMSO-$d_6$): δ=157, 154, 142, 141, 137, 131, 131, 130, 128, 128, 127, 122, 121, 120, 111, 62, 55, 46.
MS: m/z=373 ($MH^+$)

Example 16

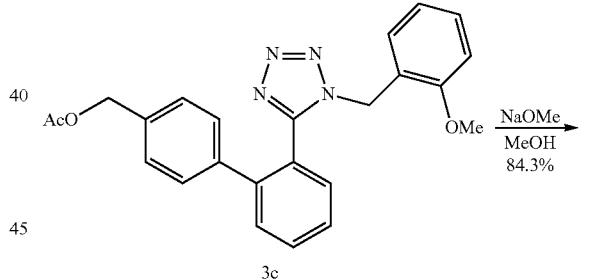

To a mixture of {2'-[1-(o-methoxybenzyl)-1H-tetrazol-5-yl]biphenyl-4-yl}methyl acetate (compound 3c, 1.01 g, 2.44 mmol) and methanol (5.0 mL) was added 28% sodium methoxide methanol solution (24 μL, 23 mg, 0.12 mmol), and the mixture was stirred for 9 hr under a nitrogen atmosphere. The reaction was monitored by TLC (eluent: toluene/ethyl acetate (2:1)). The reaction mixture was concentrated under reduced pressure in a bath at 40° C., and the residue was dissolved in chloroform (6 mL). The solution was washed twice with 20% brine (2 mL), dried over magnesium sulfate (0.3 g), and concentrated under reduced pressure at 40° C. or lower to give crystals. To the crystals was added chloroform, and the content was adjusted to 3.4 g. Hexane (5.5 mL) was added with stirring, and the temperature of the cold bath was decreased from 20° C. to 1° C. to cool the mixture. The solid was collected by filtration, washed with hexane (4 mL), in a bath at 40° C., and dried under reduced pressure to give compound 4c (765 mg, 84.3%) as white crystals.

Example 17

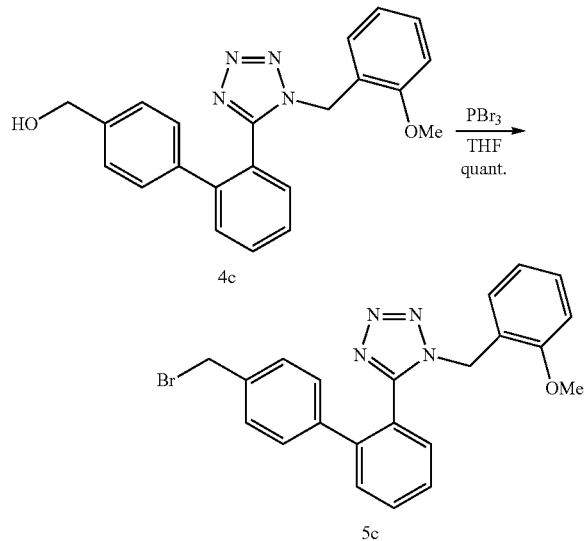

To a mixture of {2'-[1-(o-methoxybenzyl)-1H-tetrazol-5-yl]biphenyl-4-yl}methanol (compound 4c, 47.2 mg, 0.127 mmol) and tetrahydrofuran (0.35 mL) was added a solution (14.2%; 0.272 mL, 265 mg, phosphorus tribromide content 37.7 mg, 0.139 mmol) of phosphorus tribromide in tetrahydrofuran in a bath at −15° C. under cooling, and the mixture was stirred at −14--4° C. for 1.5 hr under nitrogen stream. The reaction was monitored by TLC (eluent: toluene/ethyl acetate (3:2)). To the reaction mixture were added cold water (0.33 ml), ethyl acetate (10 mL) and 20% brine (1.0 mL), and the organic layer was separated. The organic layer was washed with 20% brine (1.0 mL), dried over magnesium sulfate (1.2 g), and concentrated under reduced pressure at 40° C. or lower. To the concentrate was added chloroform (5 ml), and the mixture was concentrated under reduced pressure. The operations were repeated three times. The residue was dried under reduced pressure to give a crude product of compound 5c (63.1 mg, 114% of the theoretical yield).

Example 18

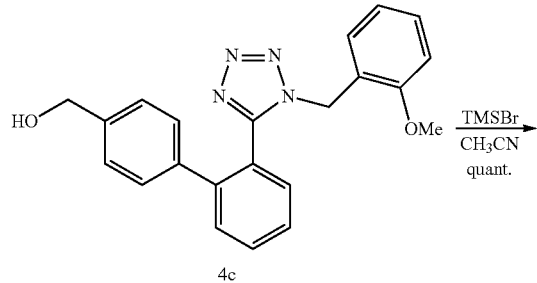

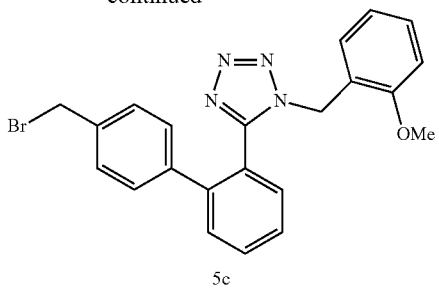

To a mixture of {2'-[1-(o-methoxybenzyl)-1H-tetrazol-5-yl]biphenyl-4-yl}methanol (compound 4c, 200 mg, 0.537 mmol) and acetonitrile (1.0 mL) was added bromotrimethylsilane (142 μL, 165 mg, 1.08 mmol), and the mixture was stirred for 6 hr in a bath at 50° C. under a nitrogen atmosphere. The reaction was monitored by HPLC. The bath was removed, and the reaction mixture was cooled in a bath at 0° C. The mixture was diluted with cold ethyl acetate (3.8 mL), and washed with cold water (1.8 ml). The aqueous layer was extracted with cold ethyl acetate (3.8 mL). The combined organic layers were washed successively with 10% brine (1.7 mL), saturated brine (1.0 ml) and saturated brine (2.0 mL), dried over magnesium sulfate (1.2 g), and concentrated under reduced pressure at 35° C. or lower. The solvent was replaced with chloroform, and the mixture was purified by silica gel (Merck; silica gel 60N (trade name)) column chromatography (eluent: toluene/ethyl acetate (100:0-50:1)). The mixed fractions of the main resultant product and the less polar resultant product were collected, and concentrated under reduced pressure. To the residue was added chloroform (5 mL or more), and the mixture was concentrated under reduced pressure. The operations were repeated three times. The residue was vacuum-dried at 40° C. to give a crude product of compound 5c (240 mg, 103% of the theoretical yield).

HPLC measurement condition:
column Cadenza CD-C18, 3 μm, 4.6×150 mm
mobile phase MeCN/30 mM $KH_2PO_4$ (3:2)
flow 1.0 mL/min
detector UV 225 nm
temperature 40° C.
$^1$H-NMR ($CDCl_3$): δ=7.64 (td, J=7.2, 2.0 Hz, 1H), 7.57 (dd, J=7.2, 1.4 Hz, 1H), 7.48 (td, J=7.2, 1.4 Hz, 1H), 7.45 (dd, J=7.2, 2.0 Hz, 1H), 7.31 (d, J=8.3 Hz, 2H), 7.21 (ddd, J=8.4, 7.2, 2.0 Hz, 1H), 7.10 (d, J=8.3 Hz, 2H), 6.81 (dd, J=7.2 Hz, 2.0 Hz, 1H), 6.78 (t, J=7.2 Hz, 1H), 6.69 (d, J=8.4 Hz, 1H), 4.75 (s, 2H), 4.47 (s, 2H), 3.51 (s, 3H).
MS: m/z=435 (MH$^+$)

Example 19

Step 1

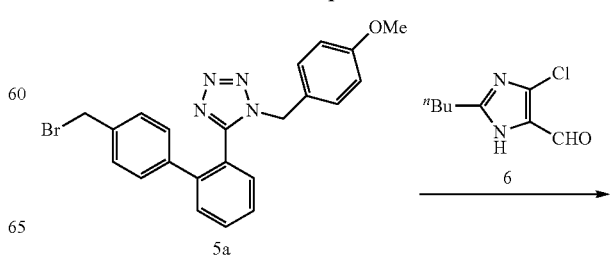

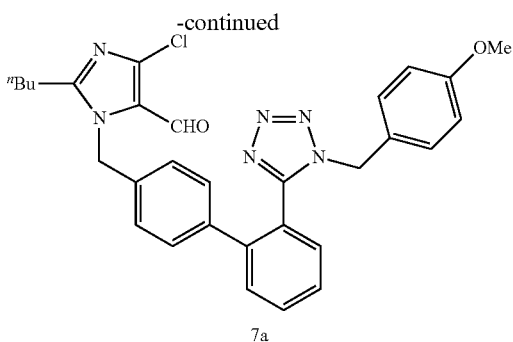

7a

Under a nitrogen atmosphere, into a 50 mL pear-shaped flask were charged compound 5a (93.0 mg, 0.213 mmol), compound 6 (40.5 mg, 0.217 mmol), DMA (1.00 g) and potassium carbonate (30.3 mg, 0.219 mmol), and the mixture was reacted at −10° C. for 4 hr, and stirred at room temperature for 4 hr. Then, ethyl acetate (10 mL) was added thereto, the mixture was filtered, and the solid was washed with ethyl acetate (5 mL). The filtrate and washing were combined, concentrated, and vacuum-dried at room temperature to give a pale-yellow liquid (0.11 g, yield 95%). The obtained crude product was purified by silica gel column chromatography (ethyl acetate/hexane-1/2) to give compound 7a (0.106 mg, yield 92%) as a colorless solid.

$^1$H-NMR (400 MHz, CDCl$_3$) δ=0.90 (3H, t, J=7.2), 1.30-1.42 (2H, m), 1.61-1.73 (2H, m), 2.61 (2H, t, J=7.6), 3.72 (3H, s), 4.74 (2H, s), 5.52 (2H, s), 6.66-6.73 (4H, m), 6.97 (2H, d, J=8.0), 7.09 (2H, d, J=8.0), 7.34 (1H, d, J=7.6), 7.46 (1H, t, J=7.2), 7.53 (1H, d, J=7.6), 7.65 (1H, t, J=7.6), 9.75 (1H, s).

$^{13}$C-NMR (400 MHz, CDCl$_3$) δ=122.64, 124.11, 124.87, 135.35, 138.45, 140.74, 143.03, 153.92, 154.30, 159.52 (10s), 113.98, 126.73, 127.90, 129.07, 129.26, 130.10, 131.07, 131.43, 177.64 (9d), 22.49, 26.60, 29.32, 47.88, 50.54 (5t), 13.83, 55.30 (2q).

IR(KBr) ν(cm$^{-1}$):1664
EIMS (m/z):540(M$^+$-1)
melting point: 47.1-48.6° C.

Step 2

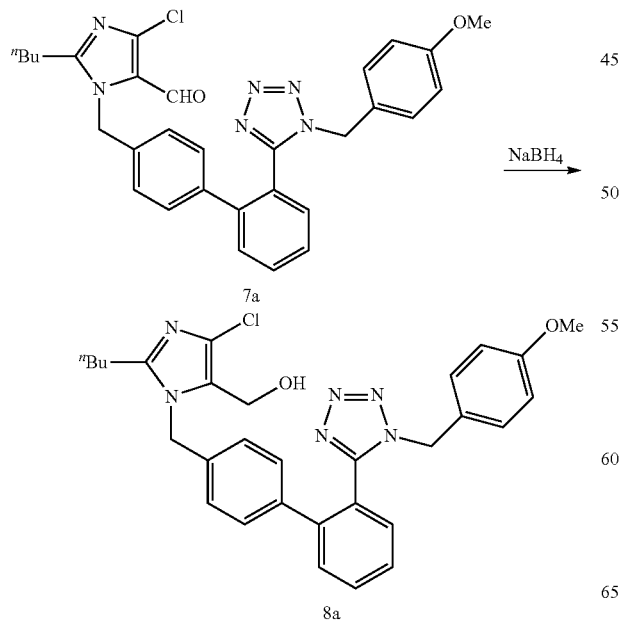

8a

Under an argon atmosphere, into a 50 ml flask were charged compound 7a (433 mg, 0.8 mmol) and methanol (0.50 ml), and NaBH$_4$ (90.8 mg, 2.4 mmol) was added thereto at −10° C. The mixture was allowed to warm to room temperature, and stirred for 0.5 hr. Then, methanol (0.50 mL) was added thereto, and the mixture was stirred at room temperature for 1.5 hr. Then, NaBH$_4$ (30.3 mg, 0.8 mmol) was added thereto, and the mixture was stirred at room temperature for 1 hr. The disappearance of the starting material was confirmed by TLC (ethyl acetate/hexane=1/1). 50% Aqueous acetic acid solution (0.029 mL) was added thereto, and the mixture was stirred at 20-25° C. for 30 min. Then, water (1.6 mL) was added dropwise thereto, and the mixture was stirred at room temperature for 2 hr, and then at 5-10° C. for 30 min. The resulting crystals were collected by filtration, and dried to give compound 8a (373 mg, yield 86%).

$^1$H-NMR (400 MHz, CDCl$_3$) δ=0.88 (3H, t, J=7.6), 1.28-1.41 (2H, m), 1.60-1.70 (2H, m), 2.54 (2H, dd, J=7.6), 3.73 (3H, s), 4.49 (2H, d, J=6.4), 4.78 (2H, s), 5.18 (2H, s), 6.64-6.75 (4H, m), 6.91 (2H, d, J=8.0), 7.07 (2H, d, J=8.4), 7.30-7.35 (1H, m), 7.42-7.50 (1H, m), 7.51-7.55 (1H, m), 7.62-7.68 (1H, m).

$^{13}$C-NMR (400 MHz, CDCl$_3$) δ=122.63, 124.55, 124.88, 127.46, 135.90, 138.37, 140.88, 148.37, 153.92, 159.54 (10s), 114.00, 126.25, 127.90, 129.13, 129.26, 130.12, 130.99, 131.44 (8d), 22.53, 26.88, 29.80, 47.16, 50.57, 53.24 (6t), 13.90, 55.33 (2q).

IR(KBr) ν(cm$^{-1}$): 1612, 1583
EIMS (m/z):542(M$^+$-1)
melting point: 119.5-120.8° C.

Step 3

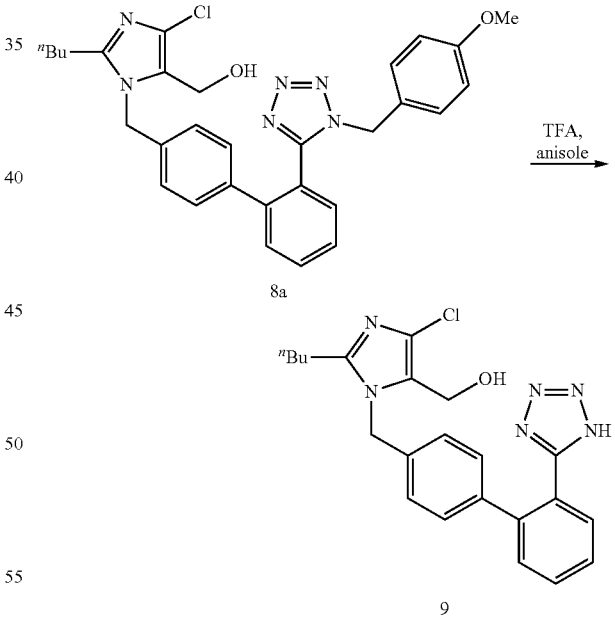

Into a 50 mL flask were charged compound 8a (73.0 mg, 0.13 mmol), trifluoroacetic acid (1 mL) and anisole (0.05 mL (about 50 mg)), and the mixture was stirred at 60° C. for 1.5 hr. The completion of the reaction was confirmed by TLC (ethyl acetate/hexane=1/1). The reaction mixture was dissolved in 3% aqueous potassium hydroxide solution (20 mL), and the solution was washed with hexane (10 mL). The aqueous layer was acidified to pH 2.65 with 1N hydrochloric acid to precipitate a solid. The mixture was extracted with ethyl acetate (10 mL×3). The organic layers were combined, washed with 10% brine (20 ml), dried over magnesium sulfate, and concentrated to give losartan (compound 9, 27.9 mg, yield 49%).

$^1$H-NMR (400 mHz, DMSO-$d_6$) δ=0.79 (3H, t, 1.18-1.30 (2H, m), 1.37-1.48 (2H, m), 2.47 (2H, t, J=8.0), 4.32 (2H, s), 5.24 (2H, s), 6.98-7.08 (4H, m), 7.48-7.72 (4H, m).

IR(KBr) ν(cm$^{-1}$):1741

EIMS (m/z):422(M$^+$)

Example 20

Step 1

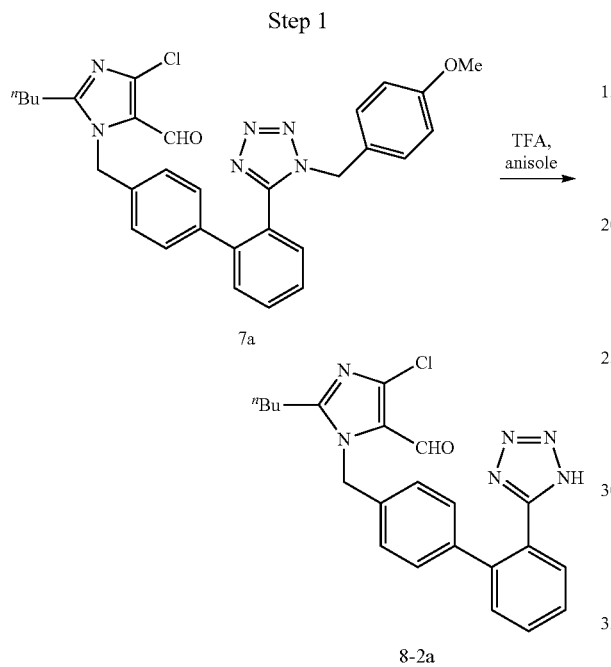

A mixture of compound 7a (93.0 mg, 0.172 mmol) obtained in Step 1 of Example 19, anisole (64 μL, 63 mg, 0.59 mmol) and trifluoroacetic acid (1.3 mL) was stirred at room temperature for 3 hr under a nitrogen atmosphere, and heated successively to 45° C. for 1 hr, 65° C. for 4 hr and 80° C. for 5 hr. The reaction was monitored by HPLC and TLC (eluent: dichloromethane/methanol (20:1)). The reaction mixture was concentrated under reduced pressure at 40° C., and mixed with 1 mol/L aqueous potassium hydroxide solution (5 mL). Water (20 mL) and toluene (20 mL) were added thereto. The aqueous layer was separated, washed with toluene (20 mL), acidified to pH 1.8 with 1 mol/L hydrochloric acid, and extracted three times with ethyl acetate (20 mL). The combined organic layers were washed with 10% brine (30 mL), dried over magnesium sulfate (1.5 g), and concentrated under reduced pressure at 40° C. to give a crude product (89.4 mg; 124% of the theoretical yield).

A part of the crude product was roughly purified by preparative TLC (eluent: dichloromethane/methanol (20:1)), and then purified by preparative TLC (eluent: dichloromethane/methanol (10:1), three times) to give compound 8-2a (32.9 mg, 45.5% relative to charged starting material) as a whitish brown solid.

The remaining crude product without the above-mentioned purification was dried under reduced pressure (40° C.) to give compound 8-2a (9.1 mg, 13% of the theoretical yield, which is calculated from the charged starting material).

Accordingly, the total yield of compound 8-2a was assumed to be 50.6%.

IR(KBr):1667(C=O), 1604 cm$^{-1}$.

$^1$H-NMR (CDCl$_3$): δ=9.69 (s, 1H, CHO), 8.04 (dd, J=7.7, 1.5 Hz, 1H, biphenyl), 7.60 (td, J=7.7, 1.5 Hz, 1H, biphenyl), 7.54 (td, J=7.7, 1.5 Hz, 1H, biphenyl), 7.42 (dd, J=7.7, 1.5 Hz, 1H, biphenyl), 7.18 (d, J=8.2 Hz, 2H, biphenyl), 7.04 (d, J=8.2 Hz, 2H, biphenyl), 5.54 (s, 2H, CH$_2$), 2.64 (t, J=7.7 Hz, 2H, 1-CH$_2$ in Bu), 1.68 (quint, J=7.7 Hz, 2H, 2-CH$_2$ of Bu), 1.36 (sext, J=7.7 Hz, 2H, CH$_2$Me), 0.89 (t, J=7.7 Hz, 3H, CH$_3$ of Bu).

MS:421 (MH$^+$)

Step 2

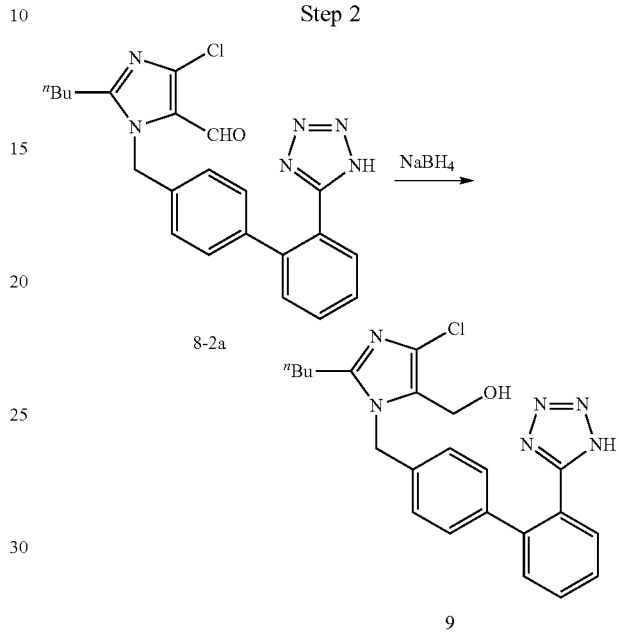

A mixture of 2-butyl-4-chloro-1-{[2'-(1H-tetrazol-5-yl)biphenyl-4-yl]methyl}imidazole-5-carbaldehyde (compound 8-2a) (or 2-butyl-4-chloro-1-{[2'-(2H-tetrazol-5-yl)biphenyl-4-yl]methyl}imidazole-5-carbaldehyde) (101 mg, 0.240 mmol), 1 mol/L aqueous sodium hydroxide solution (0.24 mL) and water (0.24 mL) was cooled to 5° C., and NaBH$_4$ (18.4 mg, 0.486 mmol) was added thereto. The reaction mixture was stirred at 5° C. for 25 min, and then at room temperature for 3 hr. NaBH$_4$ (8.6 mg, 0.23 mmol) was added thereto, and the mixture was stirred for 1 hr. The reaction was monitored by TLC (eluent: chloroform/methanol (10:1)) and HPLC. To the reaction mixture was added water (0.5 mL), and the mixture was washed with diisopropyl ether (0.5 mL). The aqueous layer was acidified to pH 2 with 1% HCl, and extracted three times with ethyl acetate (5 mL). The obtained organic layer was washed with 10% brine (5 ml), dried over magnesium sulfate (0.35 g), and concentrated to dryness to give a white solid (66.1 mg, 65.2% of the theoretical yield). The obtained concentrate was dissolved in water/acetonitrile (4:3, 1.4 mL), and the solution was suspended with water (0.49 mL). Seed crystals were appropriately added thereto, and the suspension was cooled to 5° C. The precipitated solid was filtered, washed with cold water/acetonitrile (4:1, a few mL), and dried under reduced pressure at 40-55° C. to give losartan (compound 9, 29.6 mg, yield 29.2%).

melting point: 161-164° C.

IR(KBr): 3374(OH), 1604, 1579, 1469 cm$^{-1}$ $^1$H-NMR (DMSO-$d_6$): δ=7.68 (t, J=7.4 Hz, 1H, biphenyl), 7.66 (d, J=7.4 Hz, 1H, biphenyl), 7.58 (t, J=7.4 Hz, 1H, biphenyl), 7.55 (d, J=7.4 Hz, 1H, biphenyl), 7.08 (d, J=8.2 Hz, 2H, biphenyl), 7.02 (d, J=8.2 Hz, 2H, biphenyl), 5.23 (s, 1H, CH$_2$N), 4.32 (s, 1H, CH$_2$O), 2.45 (t, J=7.5 Hz, 2H, 1-CH$_2$ of Bu), 1.44 (quint, J=7.5 Hz, 2H, 2-CH$_2$ of Bu), 1.23 (sext, J=7.5 Hz, 2H, CH$_2$Me), 0.80 (t, J=7.7 Hz, 3H, CH$_3$ of Bu).

MS:m/z=423 (MH$^+$)

Example 21

Step 1

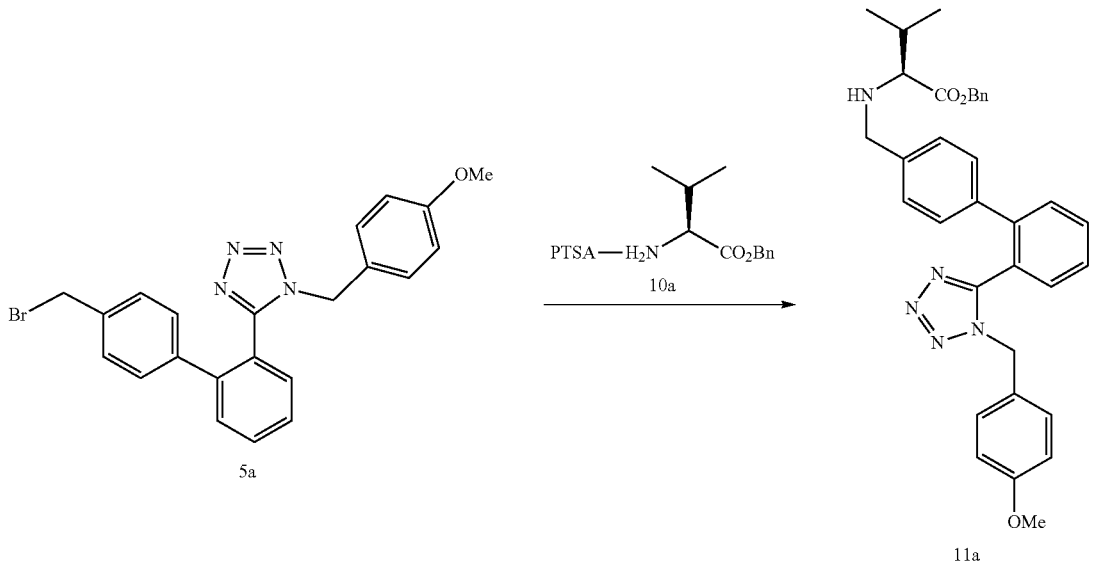

Into a 50 mL flask were charged acetonitrile (20 mL), compound 5a (1.95 g, 4.50 mmol), benzyl valinate p-toluenesulfonic acid (PTSA) salt (compound 10a, 2.56 g, 6.75 mmol) and ethyldiisopropylamine (2.19 g, 16.9 mmol), and the mixture was refluxed at 85° C. for 2 hr. The completion of the reaction was confirmed by TLC (eluent: methanol/chloroform=1/19). After completion of the reaction, the mixture was diluted with ethyl acetate (20 mL), and washed with water (5 mL). The aqueous layer was extracted with ethyl acetate (10 mL). The organic layers were combined, and dried over magnesium sulfate, and the solvent was evaporated to give a yellow oil.

The obtained crude product was purified by silica gel column chromatography (ethyl acetate/toluene=1/9), and dried under reduced pressure to give benzyl N-({2'-[1-(p-methoxybenzyl)-1H-tetrazol-5-yl]biphenyl-4-yl}methyl)-L-valinate (compound 11a, 1.99 g, yield 79%) as a white oil.

$^1$H-NMR (400 MHz, CDCl$_3$) δ=0.94 (6H, q, J=3.6), 1.78 (1H, s), 1.90-2.10 (1H, m), 3.03 (1H, d, J=6.4), 3.55 (1H, d, J=13.2), 3.72 (3H, s), 3.80 (1H, d, J=13.2), 4.69 (2H, s), 5.15-5.21 (m, 2H), 5.55 (s, 1H), 6.68 (4H, q, J=8.8), 6.85 (1H, d, J=8.8), 7.09 (2H, t, J=10.4), 7.19-7.29 (2H, m), 7.31-7.40 (5H, m), 7.49-7.66 (3H, m).

$^{13}$C-NMR (400 MHz, CDCl$_3$) δ=122.61, 125.03, 135.61, 137.31, 139.96, 141.28, 154.21, 159.41, 174.72 (9s), 31.78, 66.68, 113.89, 127.54, 128.27, 128.37, 128.54, 128.74, 128.99, 129.26, 130.05, 131.12, 131.33 (13d), 50.46, 51.01, 66.36 (3t), 18.67, 19.53, 55.25 (3q).

IR(KBr) ν(cm$^{-1}$): 1729, 1611

EIMS (m/z):561(M$^+$)

Step 2

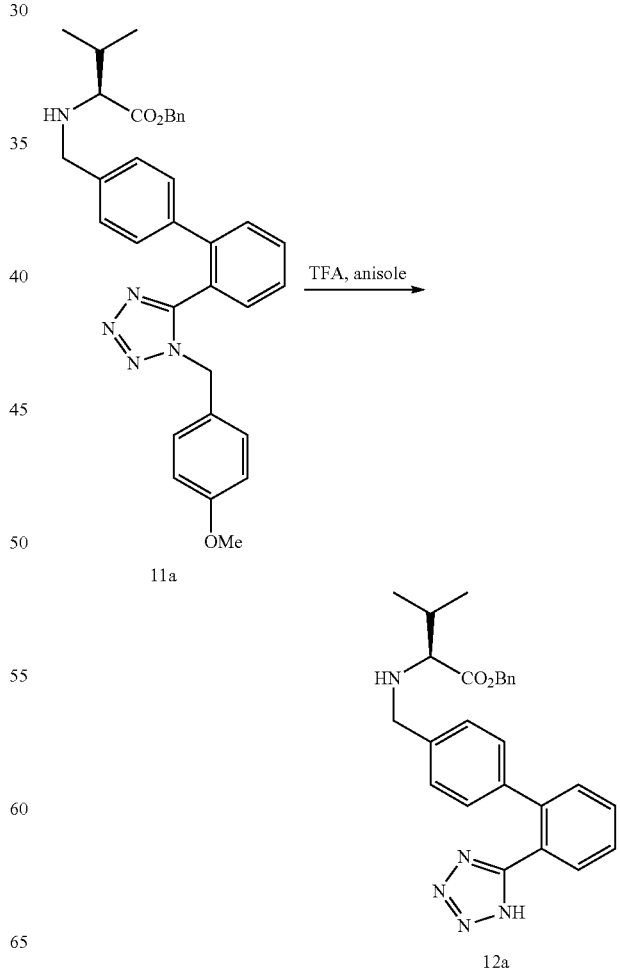

Under an argon atmosphere, into a 50 ml flask were charged compound 11a (393 mg, 0.7 mmol), trifluoroacetic acid (5.6 mL) and anisole (0.28 mL), and the mixture was stirred at 60° C. for 2.5 hr. The disappearance of the starting material was confirmed TLC (eluent: methanol/chloroform=1/19).

After completion of the reaction, the reaction mixture was concentrated, the residue was dissolved in 5% aqueous sodium bicarbonate (50 mL), and the solution was washed with hexane (20 mL×2). The aqueous layer was adjusted to pH 4.3 with 1N hydrochloric acid, and the precipitated white viscous solid was extracted with ethyl acetate (20 mL×3). The organic layers were combined, washed with 10% brine (20 mL), dried over magnesium sulfate, and concentrated to compound 12a (261 mg, yield 84%) as a white solid.

$^1$H-NMR (400 MHz, CDCl$_3$) δ=0.90 (3H, d, J=6.4), 0.95 (3H, d, J=6.8), 2.13-2.28 (1H, m), 3.49 (1H, d, J=4.4), 3.77-3.90 (2H, m), 5.19 (2H, dd, J=12.0, 29.2), 6.75-7.10 (4H, m), 7.27-7.56 (9H, m).

IR(KBr) ν(cm$^{-1}$):1742, 1668, 1604

EIMS (m/z):441(M$^+$)

melting point: 53.5-57.2° C.

Example 22

Step 1

To a solution of compound 11a (253 mg, 0.451 mmol) obtained in Step 1 of Example 21 in toluene (1.3 mL) were added pyridine (55 μL, 54 mg, 0.68 mmol) and pentanoyl chloride (compound 13a, 75 μL, 76 mg, 0.63 mmol), and the mixture was stirred at room temperature for 7 hr under a nitrogen atmosphere. Then, pyridine (18.2 mg, 0.230 mmol) and pentanoyl chloride (compound 13a, 28.0 mg, 0.232 mmol) were added thereto, and the mixture was stirred for 6 hr. Pyridine (18.6 mg, 0.235 mmol) and pentanoyl chloride (compound 13a, 30.0 mg, 0.249 mmol) were added thereto, and the mixture was stirred for 22 hr. The reaction was monitored by HPLC. To the reaction mixture was added 1 mol/L hydrochloric acid (3 mL), and the mixture was extracted twice with ethyl acetate (10 mL). The combined organic layers were washed successively with saturated aqueous sodium hydrogen carbonate solution (5 mL, twice) and 20% brine (5 mL, twice), dried over magnesium sulfate (2.4 g), and concentrated. The residue was dissolved in methanol (10.3268 g of solution). A part (5.6199 g) of the solution was concentrated under reduced pressure at 45° C. or lower to give a crude product of compound 12-2a (153 mg, 52.5% relative to the charged amount) as a yellowish brown oil. The crude product was use in the next step (deprotection). The remaining crude product was concentrated to give a crude product of compound 12-2a (119 mg, 40.7% relative to the charged amount) as a yellowish brown oil.

Step 2

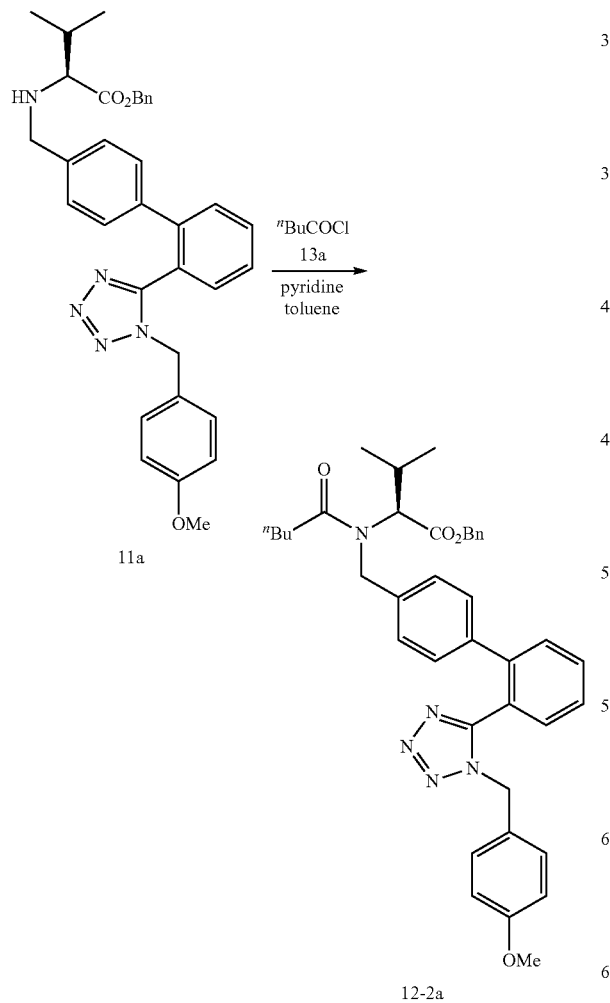

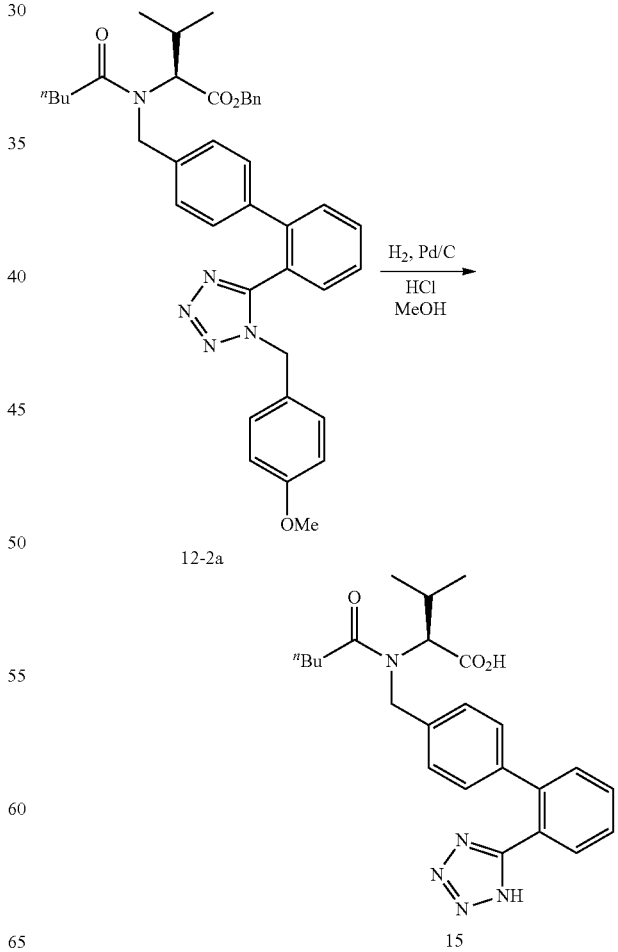

A mixture of the crude product of compound 12-2a (153 mg), methanol (21 mL) and palladium carbon (200 mg, 4.12 mg (Pd conversion)) was pressurized with hydrogen at about 0.46 MPa (4.5 gas pressure) under a hydrogen atmosphere, and stirred at room temperature for 2 hr. The pressure was discharged, and the gas in the system was replaced with nitrogen. The same catalyst (206 mg, 4.24 mg (Pd conversion)) was added thereto, and the reaction mixture was pressurized with hydrogen at 0.65 MPa under a hydrogen atmosphere, and stirred at room temperature for 3 hr. The pressure was discharged, and the gas in the system was replaced with nitrogen. The same catalyst (215 mg, 4.43 mg (Pd conversion)), and 0.2 mol/L hydrochloric acid (50 µL) was added thereto. The reaction system was purges with hydrogen, pressurized with hydrogen at 0.58-0.65 MPa, and stirred for 5 days. The reaction was monitored by HPLC. The reaction mixture was purges with nitrogen, and to the reaction mixture was added MeOH (42 ml). The mixture was filtered, and the cake was washed with MeOH (43 ml). The filtrate was concentrated under reduced pressure, and the concentrate was dissolved in 0.5 mol/L aqueous sodium hydroxide solution (1.5 mL) and water (4.2 mL). The solution was washed with MTBE (5.5 mL). The aqueous layer was washed with a mixture of water (4.2 mL) and MTBE (10 mL). The aqueous layer was acidified to pH 2 with 4 mol/L hydrochloric acid (0.17 mL) and 0.2 mol/L hydrochloric acid (0.10 mL) and 5% hydrochloric acid (0.13 mL), and extracted twice with ethyl acetate (34 mL, 10 mL). The aqueous layer was acidified to pH 1 with 5% hydrochloric acid (70 µL), and extracted with ethyl acetate (30 mL). The combined organic layers were washed twice with 10% brine (20 ml), dried over magnesium sulfate (2.0 g), and concentrated to dryness under reduced pressure at 40° C. The concentrate was dissolved in ethyl acetate (0.29 ml), cyclohexane (0.30 mL) was added thereto, and seed crystals were added thereto. To the mixture was added cyclohexane (0.30 mL), and the mixture was cooled to 9° C. The precipitated solid was collected by filtration, washed with cyclohexane (0.30 mL), and dried under reduced pressure at 40° C. to give valsartan (compound 15, 25.9 mg, yield 25.1%) as a white solid.

melting point: about 70-95° C.

IR(KBr):1732($CO_2H$), 1607(CON) $cm^{-1}$ $^1$H-NMR (DMSO-$d_6$): δ=16.3 (br s, 1H, $CO_2H$), 12.6 (br s, 1H, $CO_2H$ or $CO_2H$), 7.70-7.63 (m, 2H, biphenyl; $C_M$, $C_m$), 7.58-7.53 (m, 2H, biphenyl; $C_M$, $C_m$), 7.20 (d, J=8.2 Hz, 1H, biphenyl; $C_m$), 7.08 (d, J=8.2 Hz, 1H, biphenyl; $C_m$), 7.07 (d, J=8.2 Hz, 1H, biphenyl; $C_M$), 6.97 (d, J=8.2 Hz, 1H, biphenyl; $C_m$), 4.67 (s, 2H, $CH_2$-Val; $C_m$), 4.48 (d, J=15.2 Hz, 1H, $CH_2$-Val; $C_m$), 4.36 (d, J=10.3 Hz, 1H, CHPr$^i$; $C_m$), 4.08 (d, J=10.5 Hz, 1H, CHPr$^i$; $C_M$), 2.22-2.12 (m, 1H, $CHMe_2$; $C_M$, $C_m$), 2.21 (dt, J=15.8, 7.9 Hz, $^1$H, 1-$CH_2$ of Bu; $C_M$), 2.03 (dt, J=15.8, 7.9 Hz, 1H, 1-$CH_2$ of Bu; $C_M$), 1.54 (quint, J=6.9 Hz, 2H, 2-$CH_2$ of Bu; $C_m$), 1.41 (dquint, J=14.1, 7.9 Hz, 1H, 2-$CH_2$ of Bu; $C_M$), 1.37 (dquint, J=14.1, 7.9 Hz, 1H, 2-$CH_2$ of Bu; $C_M$), 1.31 (sext, J=6.9 Hz, 2H, $CH_2$Me; $C_m$), 1.15 (sext, J=7.9 Hz, 2H, $CH_2$Me; $C_M$), 0.93 (d, J=6.9 Hz, 3H, $CH_3$ of i-Pr; $C_m$), 0.93 (d, J=7.9 Hz, 3H, $CH_3$ of i-Pr; $C_M$), 0.88 (t, 3H, J=6.9 Hz, 4-$CH_3$ of Bu; $C_m$), 0.76 (t, 3H, J=7.9 Hz, 4-$CH_3$ of Bu; $C_M$), 0.75 (d, 3H, J=7.9 Hz, $CH_3$ of i-Pr; $C_M$), 0.70 (d, J=6.9 Hz, 3H, $CH_3$ of i-Pr; $C_m$).

Example 23

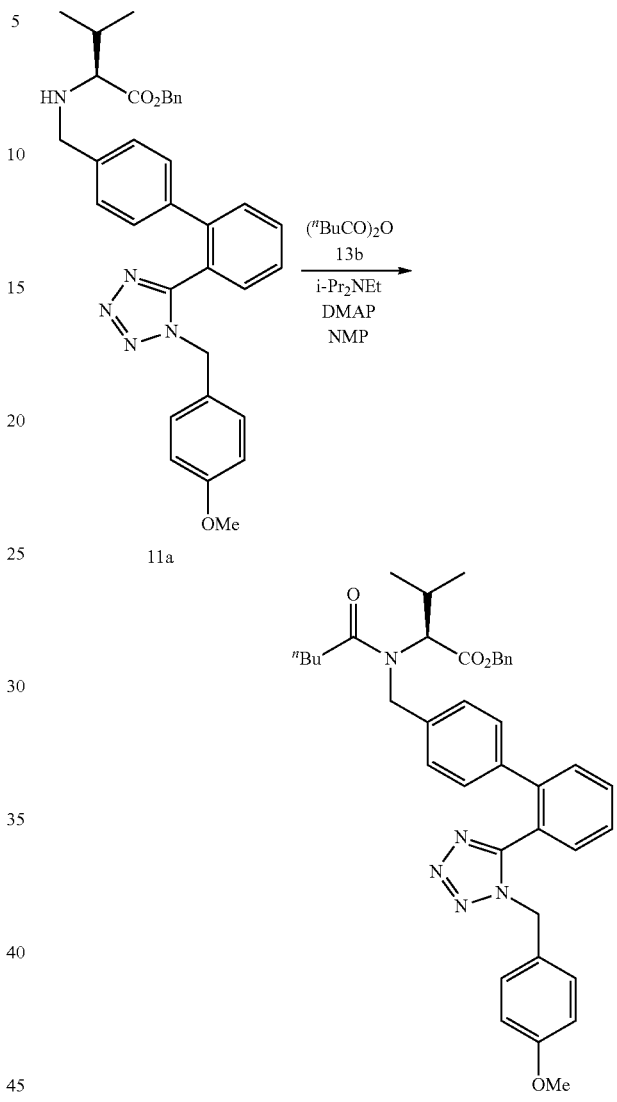

To a solution of compound 11a (0.18 g, 0.32 mmol) obtained in Step 1 of Example 21 in N-methyl-2-pyrrolidone (0.9 mL) were added ethyldiisopropylamine (0.10 mL, 74 mg, 0.57 mmol) and pentanoic acid anhydride (compound 13b, 95 µL, 90 mg, 0.48 mmol), and the mixture was stirred at room temperature for 1 hr under a nitrogen atmosphere. To the reaction mixture was added 4-(dimethylamino)pyridine (14.7 mg, 0.120 mmol), and the mixture was heated at 45° C. for 2 hr. Ethyldiisopropylamine (0.10 mL, 74 mg, 0.57 mmol) and pentanoic acid anhydride (compound 13b, 95 µL, 90 mg, 0.48 mmol) were added thereto, and the mixture was warmed to 70° C., and then to 90° C. after 12 hr, and stirred for 5 hr. Ethyldiisopropylamine (40 µL, 30 mg, 0.23 mmol) and pentanoic acid anhydride (compound 13b, 50 µL, 47 mg, 0.25 mmol) were added thereto, and the mixture was stirred at 100° C. for 13 hr. The reaction was monitored by HPLC. The reaction mixture was allowed to cool to room temperature, and 1% hydrochloric acid (3 mL) and ethyl acetate (10 mL) were added thereto. The organic layer was separated, and the aqueous layer was extracted with ethyl acetate (10 mL). The combined organic layers were washed successively with saturated aqueous sodium hydrogen carbonate solution (5 mL, twice) and 10% brine (5 mL, twice), and dried over magnesium sulfate to give a crude product (236 mg, 114% of the theoretical yield). The crude product was purified by TLC (eluent: hexane/ethyl acetate (10:9)) to give compound 12-2a (227 mg, 109% of the theoretical yield) as a pale-yellow oil.

IR(neat):1735(COO), 1654(CON), 1613 cm$^{-1}$.

$^1$H-NMR (CDCl$_3$): δ=7.65 (t, J=6.8 Hz, 1H, biphenyl; C$_M$), 7.65 (t, J=6.8 Hz, 1H, biphenyl; C$_m$), 7.53 (d, J=6.8 Hz, 1H, biphenyl; C$_M$), 7.50 (d, J=6.8 Hz, 1H, biphenyl; C$_m$), 7.45 (t, J=6.8 Hz, 1H, biphenyl; C$_M$), 7.42 (t, J=6.8 Hz, 1H, biphenyl; C$_m$), 7.36-7.23 (m, 6H, biphenyl, Ph of Bn; C$_M$, C$_m$), 7.13 (d, J=8.4 Hz, 1H, biphenyl; C$_m$), 7.07 (d, J=8.4 Hz, 1H, biphenyl; C$_M$), 7.03 (d, J=8.4 Hz, 1H, biphenyl; C$_m$), 7.01 (d, J=8.4 Hz, 1H, biphenyl; C$_M$), 6.72 (d, J=8.7 Hz, 1H, Ar of PMB; C$_M$), 6.69 (d, J=8.7 Hz, 1H, Ar of PMB; C$_m$), 6.68 (d, J=8.7 Hz, 1H, Ar of PMB; C$_M$), 6.67 (d, J=8.7 Hz, 1H, Ar of PMB; C$_m$), 4.94 (d, J=12.6 Hz, 1H, CH$_2$ of Bn; C$_M$), 4.89 (d, J=12.6 Hz, 1H, CH$_2$ of Bn; C$_m$), 4.86 (d, J=12.6 Hz, 1H, CH$_2$ of Bn; C$_m$), 4.79 (d, J=15.9 Hz, 1H, CH$_2$-Val; C$_M$), 4.79 (d, J=10.6 Hz, 1H, CHPr$^i$; C$_M$), 4.78 (d, J=12.6 Hz, 1H, CH$_2$ of Bn; C$_m$), 4.68 (d, J=18.0 Hz, 1H, CH$_2$-Val; C$_M$), 4.67 (s, 2H, CH$_2$-Val; C$_M$ or C$_m$), 4.67 (d, J=14.8 Hz, 1H, CH$_2$-Val; C$_m$ or C$_M$), 4.66 (d, J=15.9 Hz, 1H, PMB; C$_m$), 4.63 (d, J=14.8 Hz, 1H, CH$_2$-Val; C$_M$ or C$_m$), 4.53 (d, J=18.0 Hz, 1H, CH$_2$-Val; C$_M$), 4.42 (d, J=15.9 Hz, 1H, PMB; C$_m$), 4.07 (d, J=10.6 Hz, 1H, CHPr$^i$; C$_M$, C$_m$), 3.72 (s, 3H, CH$_3$O; C$_M$), 3.72 (s, 3H, CH$_3$O; C$_m$), 2.56 (dt, J=16.0, 8.0 Hz, 1H, 1-CH$_2$ of Bu; C$_M$), 2.42 (dt, J=16.0, 8.0 Hz, 1H, 1-CH$_2$ of Bu; C$_M$), 2.35-2.30 (m, 1H, CHMe$_2$; C$_M$, C$_m$) 2.25 (dt, J=16.0, 8.0 Hz, 1H, 1-CH$_2$ of Bu; C$_M$), 2.16 (dt, J=16.0, 8.0 Hz, 1H, 1-CH$_2$ of Bu; C$_M$), 1.70-1.25 (m, 4H; C$_M$, C$_m$), 1.37 (dquint, J=16.0, 8.0 Hz, 1H, 2-CH$_2$ of Bu; C$_M$), 1.38 (dquint, J=16.0, 8.0 Hz, 1H, 2-CH$_2$ of Bu; C$_M$), 1.26 (quint, J=6.7 Hz, 2H, CH$_2$Me; C$_m$), 0.97 or 0.96 (J=6.7 Hz, 2H, CH$_3$ of i-Pr; C$_m$), d, 0.96 (t, J=6.7 Hz, 3H, CH$_3$ of Bu; C$_m$), 0.92 (d, J=Hz, J=6.7 Hz, 3H, CH$_3$ of i-Pr; C$_M$), 0.88 (d, J=6.7 Hz, 3H, CH$_3$ of i-Pr; C$_M$), 0.84 (t, J=6.7 Hz, 1H, CH$_3$ of Bu; C$_M$) 0.81 (d, J=6.7 Hz, 3H, CH$_3$ of i-Pr; C$_m$).

$^{13}$C-NMR (CDCl$_3$): δ=178 (C=O), 174 (C=O), 170 (C=O), 170 (C=O), 160 (tetrazole), 154 (tetrazole), 141 (quaternary Ar), 141 (quaternary Ar), 138 (quaternary Ar), 138 (quaternary Ar), 137 (quaternary Ar), 137 (quaternary Ar), 135 (quaternary Ar), 135 (quaternary Ar), 132 (CH of Ar), 132 (CH of Ar), 131 (CH of Ar), 130 (CH of Ar), 129 (CH of Ar), 129 (CH of Ar), 129 (CH of Ar), 129 (CH of Ar), 128 (CH of Ar), 128 (CH of Ar), 128 (CH of Ar), 128 (CH of Ar), 128 (CH of Ar), 127 (CH of Ar), 125 (quaternary Ar), 125 (quaternary Ar), 123 (quaternary Ar), 114 (Ar CH of PMB), 114 (Ar CH of PMB), 67 (CH$_2$ of Bn), 67 (CH$_2$ of En), 66 (CHPr$^i$), 63 (CHPr$^i$), 55 (MeO), 50 (CH$_2$), 49 (CH$_2$N), 46 CH$_2$N), 33 (1-CH$_2$ of Bu), 33 (1-CH$_2$ of Bu), 28 (CH of i-Pr), 28 (CH of i-Pr) 27 (2-OH$_2$ of Bu), 27 (2-CH$_2$ of Bu), 22 (3-OH$_2$ of Bu), 22 (3-CH$_2$ of Bu) (Me of i-Pr), 20 (Me of i-Pr), 19 (Me of i-Pr), 19 (Me of i-Pr), 14 (Me of Bu), 14 (Me of Bu).

MS: m/z=646 (MH$^+$)

Example 24

Step 1

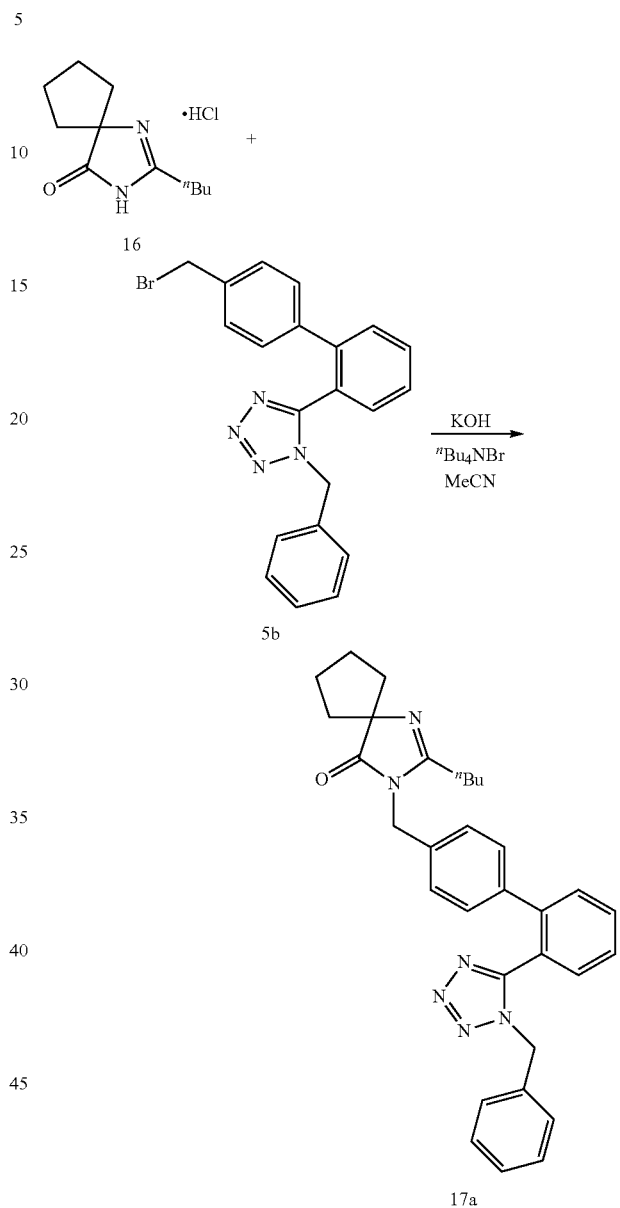

To a mixture of 1-benzyl-5-[4'-(bromomethyl)biphenyl-2-yl]-1H-tetrazole (compound 5b, 749 mg, 1.85 mmol), acetonitrile (4.8 mL), 2-butyl-1,3-diazaspiro[4.4]non-1-en-4-one hydrochloride (compound 16, 512 mg, 2.22 mmol) and tetrabutylammonium bromide (242 mg, 0.75 mmol) were added potassium hydroxide (powder, 699 mg, 12.5 mmol) and acetonitrile (1.2 mL), and the mixture was stirred at room temperature for 7 hr under a nitrogen atmosphere. The reaction was monitored by HPLC. The reaction mixture was left stand for 5 days, and water (10 mL) and tert-butyl methyl ether (30 mL) were added thereto. The organic layer was separated, and the aqueous layer was extracted with tert-butyl methyl ether (20 mL). The combined organic layers were washed successively with 5% citric acid (5.0 mL) and 20% brine (5 mL, twice). The washed organic layer was dried over magnesium sulfate (3.0 g), and concentrated under reduced pressure at 40° C. to give a crude product (0.99 g, 1.0×10²% of the theoretical yield) as a whitish orange solid containing foam. The crude product was dissolved in a mixed solvent of EtOAc (15 mL) and toluene (10 mL), and silica gel (6.0 g) was added thereto. The mixture was stirred for 1 hr, and filtered through silica gel (15 g). The silica gel was washed with ethyl acetate/toluene (3:2-4:1), and the filtrate was concentrated to 1.1 g under reduced pressure.

A part of the concentrated solution was concentrated dryness (45° C.) under reduced pressure to give a crude product (0.42 g, 44% relative to the charged starting material). The crude product was purified by TLC (eluent: ethyl acetate/hexane (2:1); twice) to give compound 17a (287 mg, purification yield 68%).

IR(KBr):1723(000), 1632(CON), 1604 cm⁻¹.

¹H-NMR (CDCl₃): δ=7.64 (td, J=7.7, 1.5 Hz, 1H, biphenyl), 7.54 (dd, J=7.7, 1.5 Hz, 1H, biphenyl), 7.44 (td, J=7.7, 1.5 Hz, 1H, biphenyl), 7.38 (dd, J=7.7, 1.5 Hz, 1H, biphenyl), 7.22 (t, J=7.7 Hz, 1H, p-Ph), 7.16 (t, J=7.7 Hz, 1H, m-Ph), 7.10 (d, J=7.7 Hz, 1H, o-Ph), 7.08 (d, J=7.7 Hz, 2H, biphenyl), 7.07 (d, J=7.7 Hz, 1H, o-Ph), 6.77 (d, J=7.7 Hz, 2H, biphenyl), 4.81 (s, 2H, CH₂N), 4.65 (s, 2H, CH₂N), 2.28 (t, J=7.7 Hz, 2H, 1-CH₂ of Bu), 2.03-1.94 (m, 6H, cyclopentanediyl), 1.83-1.81 (m, 2H, cyclopentanediyl), 1.58 (quint, J=7.7 Hz, 2H, 2-CH₂ of Bu), 1.33 (sext, J=7.7 Hz, 2H, CH₂Me), 1.87 (t, J=7.7 Hz, 2H, CH₃).

¹³C-NMR (CDCl₃): δ=187 (CO), 161 (CBu), 154 (tetrazole), 141 (quaternary Ar), 141 (quaternary Ar), 138 (quaternary Ar), 137 (quaternary Ar), 133 (quaternary Ar), 132 (CH of Ar), 131 (CH of Ar), 131 (CH of Ar), 130 (CH of Ar), 129 (CH of Ar), 129 (CH of Ar), 129 (CH of Ar), 129 (CH of Ar), 128 (CH of Ar), 128 (CH of Ar), 128 (CH of Ar), 127 (CH of Ar), 127 (CH of Ar), 123 (quaternary Ar), 51 (CH₂ of Bn), 43 (CH₂-biphenyl) 37 (CH₂ of 2-CH₂ of cyclopentanediyl), 29 (1-CH₂ of Bu), 28 (2-CH₂ of Bu), 26 (3-CH₂ of cyclopentanediyl), 22 (CH₂Me), 14 (CH₃).

MS: m/z=519 (MH⁺)

Step 2

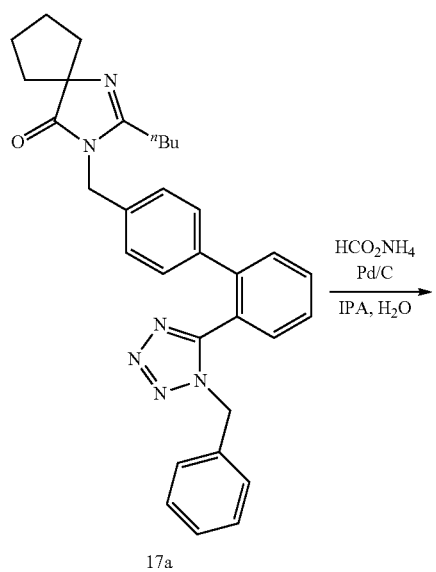

17a

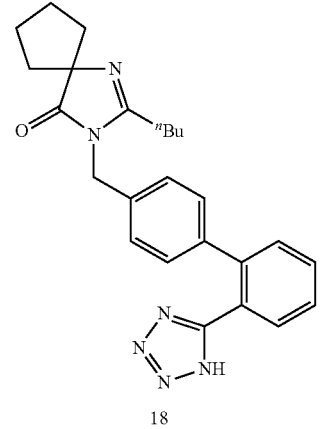

18

A mixture of crude 3-[2'-(1-benzyl-1H-tetrazol-5-yl)biphenyl-4-yl]-2-butyl-1,3-diazaspiro[4.4]non-1-en-4-one (crude product of compound 17a, 153 mg, 0.295 mmol), isopropyl alcohol/purified water (3:2, 2.0 mL), 5% palladium carbon (134 mg, 2.9 mg, 0.028 mmol (Pd conversion)) and ammonium formate (119 mg, 1.88 mmol) was heated with stirring at 55-60° C. for 3 hr. To the reaction mixture was added 5% palladium carbon (136% mg, 3.0 mg (Pd conversion), 0.028 mmol), and the mixture was heated at 80° C. for 4 hr. The reaction was monitored by HPLC and TLC (eluent: chloroform/methanol (20:1)). The reaction mixture was allowed to cool to room temperature, and filtered using isopropyl alcohol (about 20 mL). The filtrate was concentrated to 0.15 g, and 0.5 mol/L aqueous sodium hydroxide solution (1.5 mL), water (1.6 mL), tert-butyl methyl ether (3.0 ml) and 1 mol/L aqueous sodium hydroxide solution (0.2 mL) were added thereto. The organic layer was separated. The aqueous layer was washed with tert-butyl methyl ether (3.0 mL), and 4 mol/L hydrochloric acid (0.17 mL), 0.2 mol/L hydrochloric acid (0.15 mL) and 1 mol/L hydrochloric acid (0.11 mL) were added dropwise thereto to adjust the pH of the mixture to 6.0. The precipitated solid was collected by filtration, washed with water (5.0 mL), and dried under reduced pressure at 40-60° C. to give a crude product of irbesartan (compound 18) (63.9 mg, 50.5% of the theoretical yield).

¹H-NMR (DMSO-d₆): δ=7.68 (t, J=7.8 Hz, 1H, biphenyl), 7.64 (d, J=7.8 Hz, 1H, biphenyl), 7.57 (t, J=7.8 Hz, 1H, biphenyl), 7.04 (d, J=7.8 Hz, 1H, biphenyl), 7.08 (s, 4H, biphenyl), 4.68 (s, 2H, CH₂N), 2.29 (t, J=7.5 Hz, 2H, 1-CH₂ of Bu), 1.86-1.60 (m, 8H, cyclopentanediyl), 1.47 (quint, J=7.5 Hz, 2H, 2-CH₂ of Bu), 1.26 (sext, J=7.5 Hz, 2H, CH₂Me), 0.80 (t, J=7.5 Hz, 2H, CH₂).

IR(KBr): 1725(C=O), 1630(C=N) cm⁻¹
MS: m/z=429 (MH⁺)

Example 25

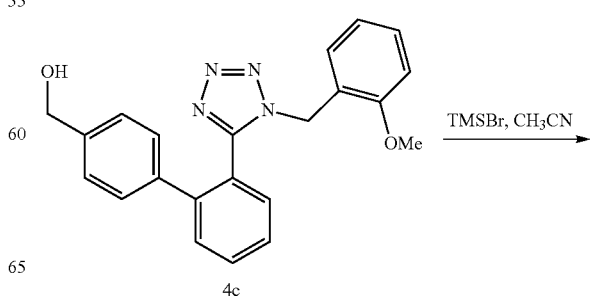

4c

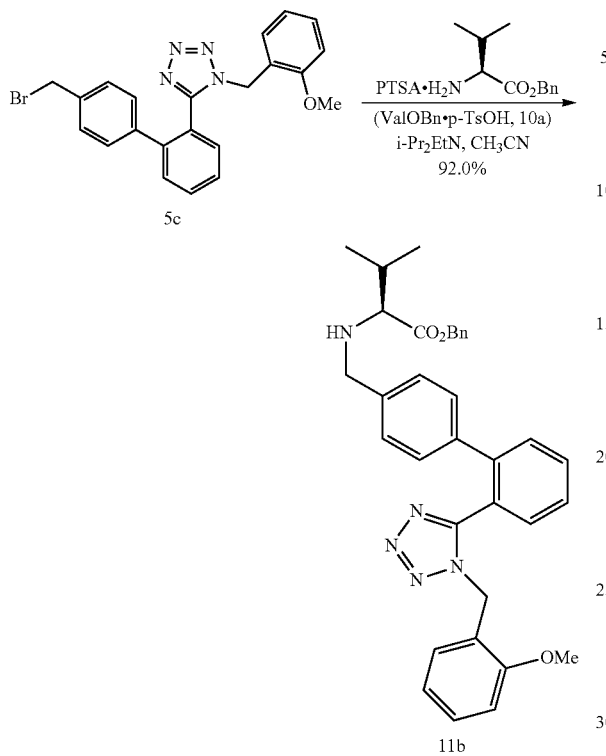

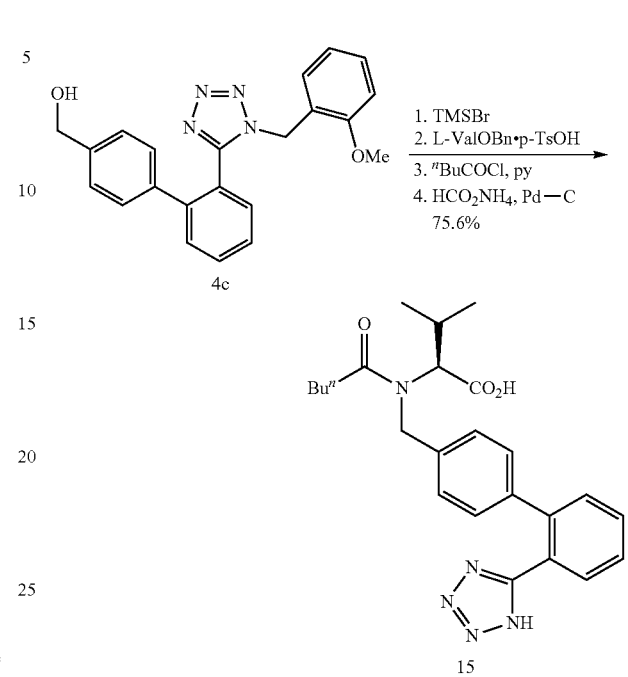

Example 26

A mixture of {2'-[1-(o-methoxybenzyl)-1H-tetrazol-5-yl]biphenyl-4-yl}methanol (compound 4c, 1.00 g, 2.69 mmol), acetonitrile (5.0 mL), bromotrimethylsilane (0.711 mL, 822 mg, 5.37 mmol) was heated with stirring for 4.5 hr in a bath at about 50° C. under a nitrogen atmosphere. The reaction mixture was cooled, and ethyldiisopropylamine (1.57 g, 12.1 mmol) and (S)-1-benzyloxycarbonyl-2-methylpropylammonium p-toluenesulfonate (1.53 g, 4.03 mmol) and acetonitrile (4.0 mL) were added thereto. The mixture was stirred with heating for 2 hr in a bath at 50° C., and allowed to cool to room temperature. Ethyl acetate (20 mL) and water (1.7 mL) were added thereto, and the organic layer was separated. The aqueous layer was extracted with ethyl acetate (10 mL), and the combined organic layers were washed with saturated brine (5.0 mL), and dried over magnesium sulfate (1.3 g). The organic layer was concentrated under reduced pressure, and chloroform (20 mL) was added thereto. The operations were repeated three times. Chloroform (10 mL) was added thereto to give a solution of crude product (assumed containing 1.51 g of the resultant product stoichiometric amount). A part of the chloroform solution (15.3 g, net 1.27 g, 2.26 mmol) of benzyl N-{2'-[1-(o-methoxybenzyl)-1H-tetrazol-5-yl]biphenyl-4-yl}methyl-L-valinate was concentrated under reduced pressure in a bath at about 40° C., and dried. Toluene (6.4 mL), pyridine (0.275 mL, 0.269 g, 3.40 mmol) and pentanoyl chloride (0.376 mL, 0.382 g, 3.17 mmol) were added thereto, and the mixture was stirred for 4 hr under a nitrogen atmosphere. The reaction was monitored by HPLC. The reaction mixture was heated for 2 hr in a bath at 40° C., and the bath was taken off. Pyridine (92.8 mg, 1.17 mmol) and pentanoyl chloride (141 mg, 1.17 mol) were added thereto, and the mixture was heated again for 3.5 hr in a bath at 40° C. The reaction mixture was allowed to cool to room temperature, 1 mol/L hydrochloric acid (5 mL) and ethyl acetate (20 mL) were added thereto, and the organic layer was separated. The aqueous layer was extracted with ethyl acetate (20 mL), and the combined organic layers were washed successively with To a mixture of {2'-[1-(o-methoxybenzyl)-1H-tetrazol-5-yl]biphenyl-4-yl}methanol (compound 4c, 113 mg, 0.303 mmol) and acetonitrile (0.56 ml) was added bromotrimethylsilane (80 μL, 93 mg, 0.61 mmol), and the mixture was stirred for 5 hr in a bath at 50° C. under a nitrogen atmosphere. The reaction was monitored by HPLC. The reaction mixture containing the obtained compound 5c was used for the next step without purification.

To the reaction mixture were added ethyldiisopropylamine (240 μL, 182 mg, 1.41 mmol), (S)-1-benzyloxycarbonyl-2-methylpropylammonium p-toluenesulfonate (compound 10a, 171 mg, 0.452 mmol) and acetonitrile (0.30 mL) at room temperature, and the mixture was stirred with heating for 3 hr in a bath at 50° C. The reaction was monitored by HPLC. The reaction mixture was allowed to cool to room temperature, diluted with ethyl acetate (3.3 mL), and washed with water (1.7 ml). The aqueous layer was extracted with ethyl acetate (3.3 ml). The combined organic layers were washed with saturated brine (2.5 mL), dried over magnesium sulfate (1.3 g), and concentrated under reduced pressure. The resultant product (compound 11b) in this solution (7.43 g) was quantified, and the net weight was 156 mg (92.0%).

HPLC measurement condition:

column Cadenza CD-C18, 3 μm, 4.6×150 mm mobile phase MeCN/30 mM $KH_2PO_4$ (3:2)

flow 1.0 mL/min detector UV 225 nm temperature 40° C.

saturated sodium hydrogen carbonate (10 mL, twice) and 20% brine (10 mL, twice), and dried over magnesium sulfate. The filtrate was concentrated under reduced pressure, and the residue was purified by column chromatography (toluene/ethyl acetate (50:1-5:1)). The obtained product (the concentrate: 1.47 g/the assumed structure and property of this intermediate was shown below) was dissolved in isopropyl alcohol (2-propanol) (4.53 g). A mixture of the isopropyl alcohol solution (24.4%, 800 mg, net 195 mg, 0.302 mmol) of the valerylated compound, palladium-carbon (E 1003 NN/W 5% Pd, water content 58.8%; 128 mg, 2.6 mg (Pd conversion), 25 μmol, 8.2 mol %), ammonium formate (96.2 mg, 1.53 mmol) and purified water (0.51 mL) was stirred at room temperature for 14 min under a nitrogen atmosphere, and heated for 6 hr in a bath at 45° C. Then, the bath temperature was increased to 55° C. The reaction mixture was allowed to cool to room temperature, and isopropyl alcohol (10 mL) was added thereto. The mixture was filtered, and the palladium-carbon was washed with isopropyl alcohol (5 mL). The filtrate was concentrated under reduced pressure, and to the residue were added 0.5 mol/L sodium hydroxide (2.0 mL), water (7 mL) and t-butyl methyl ether (5 mL). The aqueous layer was separated, and washed with t-butyl methyl ether (5 ml). 1 mol/L Hydrochloric acid (1.7 mL) and ethyl acetate (40 mL) were added thereto, and the organic layer was separated. The aqueous layer was extracted twice with ethyl acetate (15 mL), and the combined organic layers were washed twice with 10% brine (10 mL), and dried over magnesium sulfate (2.0 g). The insoluble material was filtered off, and the resultant product in the filtrate (83.0 g) was quantified, and the net weight was 99.5 mg (75.6%). The magnesium sulfate was filtered off, and the filtrate was concentrated to dryness under reduced pressure in a bath at 40° C. to give a crude product (139 mg, 106% of the theoretical yield). To the crude product was added ethyl acetate (0.30 mL), and then added cyclohexane (5.0 mL), and the mixture was cooled for 2 hr in a bath at 9° C. The solid was collected by filtration, washed with cyclohexane (0.30 mL), and dried under reduced pressure at 40° C. or lower to give valsartan (compound 15, 72.2 mg, 54.9%) as a white solid.

IR (KBr): 1730, 1619 cm$^{-1}$

The assumed structure and property of the intermediate:

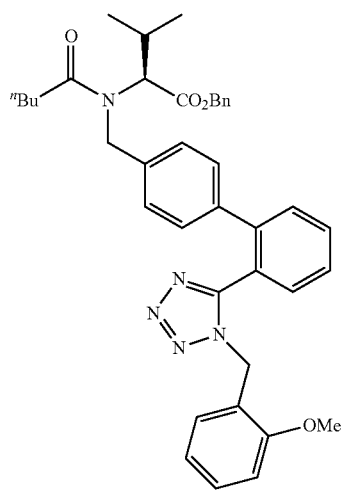

IR (neat): 1652, 1604 cm$^{-1}$

Example 27

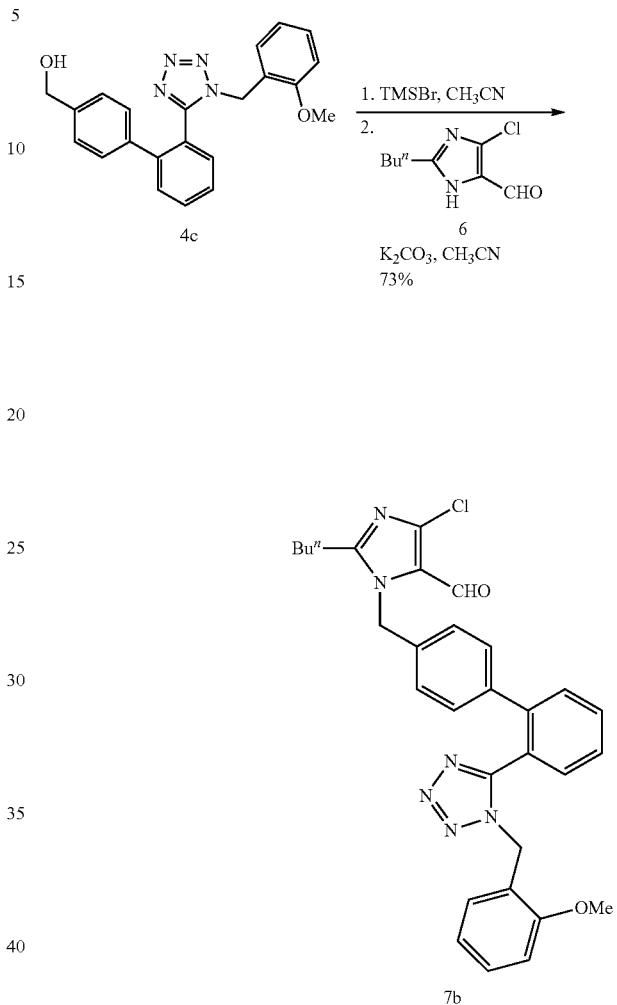

To a mixture (not dissolved) of {2'-[1-(o-methoxybenzyl)-1H-tetrazol-5-yl]biphenyl-4-yl}methanol (compound 4c, 196 mg, 0.525 mmol) and acetonitrile (1.0 mL) was added bromotrimethylsilane (0.140 mL, 162 mg, 1.06 mmol), and the mixture was heated with stirring for 7 hr in a bath at 50-60° C., and allowed to cool to room temperature. Potassium carbonate (74.8 mg, 0.541 mmol), 2-butyl-4-chloro-1H-imidazole-5-carbaldehyde (compound 6, 101 mg, 0.541 mmol) and acetonitrile (0.50 mL) were added thereto, and the mixture was heated with stirring for 3 hr in a bath at 50° C. The reaction mixture was allowed to cool to room temperature, ethyl acetate (20 mL) was added thereto, and the mixture was filtered, and the insoluble material was washed with ethyl acetate (10 mL). The obtained ethyl acetate solution was concentrated under reduced pressure, and the residue was purified by thin layer silica gel column chromatography (hexane/ethyl acetate (1:1)) to give the objective compound (compound 7b, 384 mg, 73%).

IR (neat): 1664, 1604 cm$^{-1}$

Example 28

Step 1

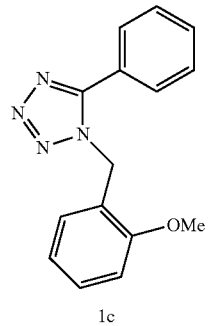
1c

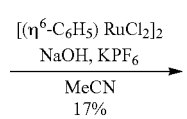

A mixture of 1-(o-methoxybenzyl)-5-phenyl-1H-tetrazole (compound 1c, 206 mg, 0.774 mmol), di-μ-chloro-bis[(η⁶-benzene)chlororuthenium] (Johnson Matthey; 193 mg, 0.773 mmol (monomer conversion)), hexafluoropotassium phosphate (285 mg, 1.55 mmol), sodium hydroxide (31.4 mg, 0.785 mmol) and acetonitrile (6.4 ml) was stirred at room temperature for 1.5 hr under a nitrogen atmosphere, and heated for 1.5 hr in a bath at about 47° C. The reaction mixture was concentrated under reduced pressure, and the residue was purified by alumina column chromatography (dichloromethane/acetonitrile (100:0-2:1)) to give the objective compound (90 mg, 17.2%).

IR (KBr): 2277, 1605, 842 cm⁻¹.

Step 2

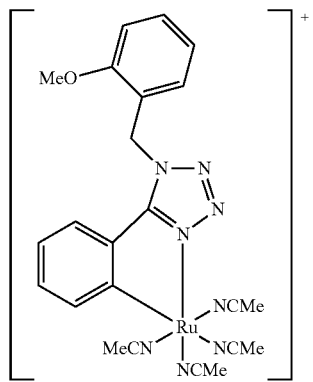

A mixture of tetrakis(acetonitrile){[1-(o-methoxybenzyl)-1H-tetrazol-5-yl]phenyl}ruthenium(II) hexafluorophosphate (69.4 mg, 0.103 mmol), triphenylphosphane (26.9 mg, 0.103 mmol), potassium carbonate (28.4 mg, 0.205 mmol), N-methyl-2-pyrrolidone solution (56.7 mg/mL; 0.831 mL, net 47.1 mg, 0.205 mmol) of p-bromobenzyl acetate (compound 2a), and N-methyl-2-pyrrolidone (138 μL) was heated with stirring for 6 hr in a bath at 140° C. under a nitrogen atmosphere. The reaction was monitored by HPLC. The reaction mixture was allowed to cool to room temperature, and ethyl acetate (5 mL) was added thereto. The mixture was filtered, and the insoluble material was washed with ethyl acetate (5 mL). The resultant product (compound 3c) in the filtrate (9.50 g) was quantified, and the net weight was 16.8 mg (40%). The HPLC analysis conditions for the resultant product are shown below.

TABLE 1

| column | Cadenza CD-C18, 3 μm, 4.6 × 150 mm |
|---|---|
| mobile phase | MeCN/30 mM KH₂PO₄ (3:2) |
| detector | UV 225 nm |
| temperature | 40° C. |
| flow | 1.0 mL/min |

Example 29

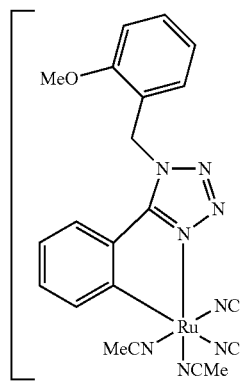
1c

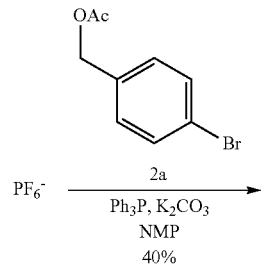

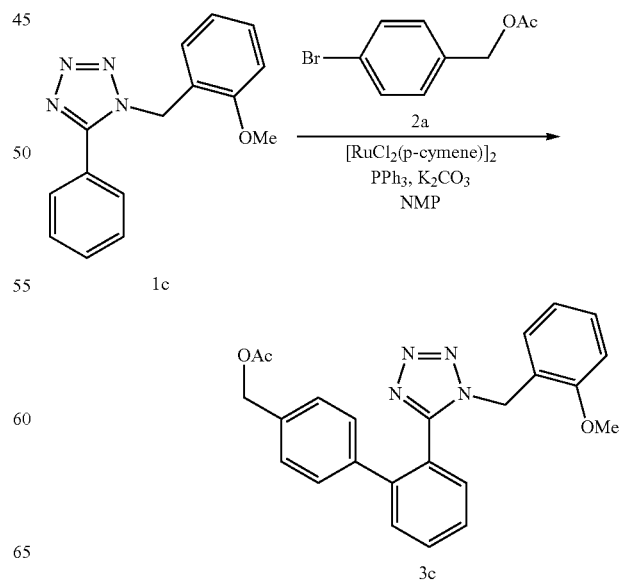
3c

A mixture of di-μ-chloro-bis[chloro(η⁶-p-cymene)ruthenium] (Johnson Matthey; 8.8 mg, 29 mmol (monomer conversion), 0.63 mol %), triphenylphosphane (13.2 mg, 50.3 μmol), 1-(o-methoxybenzyl)-5-phenyl-1H-tetrazole (compound 1c, 1.22 g, 4.60 mmol), potassium carbonate (1.27 g, 9.20 mmol), p-bromobenzyl acetate (compound 2a, 1.16 g, 5.06 mmol) and N-methyl-2-pyrrolidone (4.9 mL) was heated with stirring for 15 hr in a bath at 140° C. under a nitrogen atmosphere. The reaction was monitored by HPLC. The reaction mixture was allowed to cool to room temperature, and ethyl acetate (20 mL) was added thereto. The mixture was filtered, and the insoluble material was washed with ethyl acetate (12 mL). The resultant product (compound 3c) in the obtained filtrate (27.3 g) was quantified, and the net weight was 1.49 g (78.3%).

Example 30

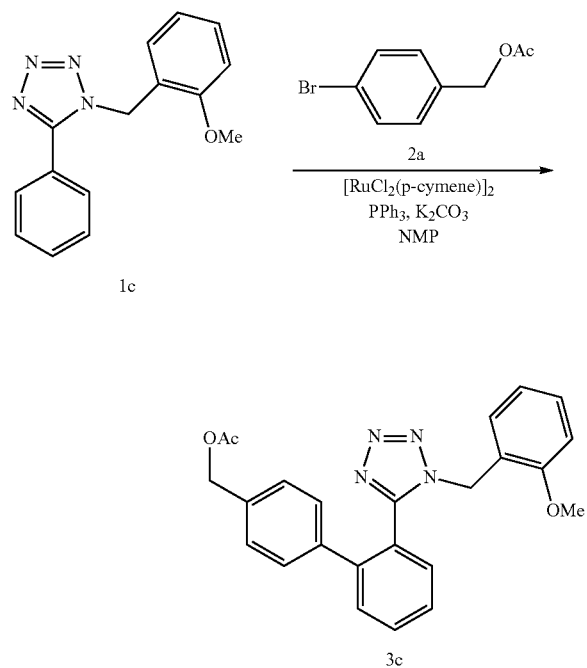

1c

3c

A mixture of di-μ-chloro-bis[chloro(η⁶-p-cymene)ruthenium] (Johnson Matthey; 6.1 mg, 20 mmol (monomer conversion), 0.31 mol %), triphenylphosphane (6.6 mg, 25 μmol), 1-(o-methoxybenzyl)-5-phenyl-1H-tetrazole (compound 1c, 1.70 g, 6.37 mmol), potassium carbonate (1.76 g, 12.7 mmol), p-bromobenzyl acetate (compound 2a, 1.61 g, 7.01 mmol) and N-methyl-2-pyrrolidone (6.8 mL) was heated with stirring for 8 hr in a bath at 140° C. under a nitrogen atmosphere. The reaction was monitored by HPLC. The reaction mixture was allowed to cool to room temperature, and ethyl acetate (20 ml) was added thereto. The mixture was filtered, and the insoluble material was washed with ethyl acetate (13 mL). The resultant product (compound 3c) in the obtained filtrate (30.6 mg) was quantified by HPLC, and the net weight was 1.54 g (58.2%).

Example 31

Step 1

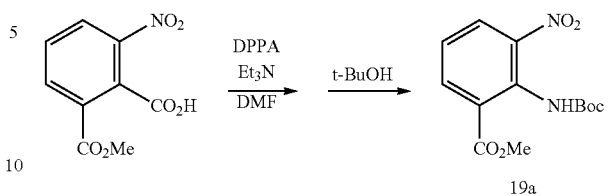

19a

To a solution of 2-methoxycarbonyl-6-nitrobenzoic acid (18.3 g, 81.3 mmol) in N,N-dimethylformamide (24.1 mL) was added dropwise diphenyl azidophosphonate (22.8 g, 83.0 mmol) at room temperature, and the dropping funnel was washed with N,N-dimethylformamide (1.8 mL). Then, triethylamine (9.75 g, 96.4 mmol) was added dropwise thereto at 22-31° C., and the dropping funnel was washed with N,N-dimethylformamide (1.6 mL). The reaction mixture was stirred at 23-28° C. for 5 hr under a nitrogen atmosphere. The reaction was monitored by HPLC. To the reaction mixture was added dropwise tert-butyl alcohol (104 g) at room temperature, and the reaction mixture was heated to about 85° C. over 5 hr, and stirred at 85-87° C. for 4 hr. The reaction was monitored by HPLC. The reaction mixture was concentrated under reduced pressure at 50° C. or lower, and ethyl acetate (156 mL) and 1.3% hydrochloric acid (229 mL) were added thereto. The organic layer was separated, and washed successively with water (74 mL), 5% aqueous sodium hydrogen carbonate solution (117 mL) and water (74 mL), and concentrated under reduced pressure at 40° C. or lower (solidification). The solid was dissolved in methanol (42.3 mL) at about 55° C. Methanol (63.5 mL) was added to the solution, and the solution was cooled from 50° C. to about 5° C. over 3 hr. During cooling, seed crystals were added thereto at 36° C., and the mixture was stirred at about 5° C. for 2 hr. The crystals were collected by filtration, washed with cold methanol (18 mL), and dried under reduced pressure at 50° C. or lower to give methyl 2-(tert-butoxycarbonylamino)-3-nitrobenzoate (compound 19a, 17.5 g, 72.5%) as pale-yellow crystals.
melting point: 92-94° C.
IR (KBr): 3368, 1735, 1608, 1540, 1508 cm⁻¹
¹H-NMR (CDCl₃): δ=9.61 (br s, 1H), 8.16 (dd, J=8.1, 1.5 Hz, 1H), 8.10 (dd, J=8.1, 1.5 Hz, 1H), 7.23 (t, J=8.1 Hz, 1H), to 3.95 (s, 3H), 1.50 (s, 9H)
MS: m/z=314 (MNH₄⁺)

Step 2

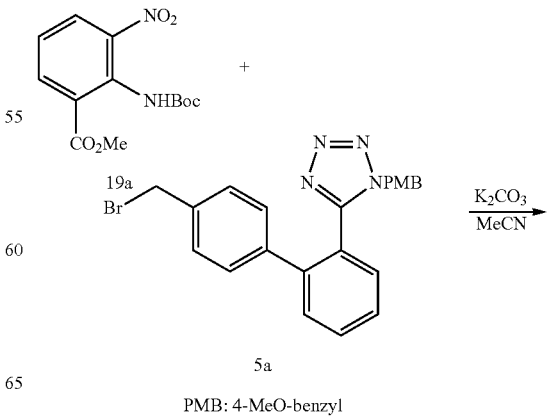

5a

PMB: 4-MeO-benzyl

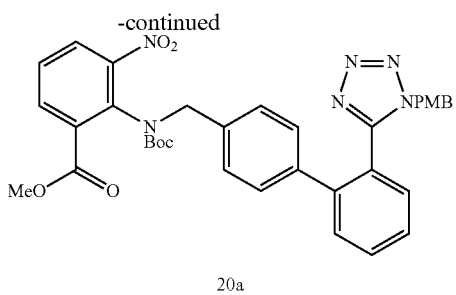

20a

A mixture of 5-[4'-(bromomethyl)biphenyl-2-yl]-1-(p-methoxybenzyl)-1H-tetrazole (compound 5a, 9.25 g, 21.2 mmol), acetonitrile (107 ml), methyl 2-(tert-butoxycarbonylamino)-3-nitrobenzoate (compound 19a, 6.43 g, 21.7 mmol) and potassium carbonate (3.00 g, 21.7 mmol) was heated under reflux for 6 hr under a nitrogen atmosphere. The reaction was monitored by TLC (eluent: toluene/ethyl acetate (4:1)). The reaction mixture was cooled, and filtered, and the cake was washed with acetonitrile (35 mL). The filtrate was concentrated under reduced pressure at 35° C. or lower to give a crude product. The crude product was purified by silica gel column chromatography (eluent: toluene/ethyl acetate (100:0-4:1)), and the fraction was concentrated. To the residue was added chloroform (about 30 ml), and the mixture was concentrated. The operations were repeated four times. The residue was dried under reduced pressure in a bath at 40° C. to give methyl 2-(N-tert-butoxycarbonyl-N-{(2'-[1-(p-methoxybenzyl)-1H-tetrazol-5-yl]biphenyl-4-yl)methyl}amino)-3-nitrobenzoate (compound 20a) as a yellowish brown amorphous solid (9.83 g (71.1%)).

IR (KBr): 1735, 1604, 1513 cm$^{-1}$ $^1$H-NMR (CDCl$_3$): δ=8.06 (dd, J=8.2, 1.7 Hz, 1H), 7.88 (dd, J=8.2, 1.7 Hz, 1H), 7.61 (td, J=7.5, 1.3 Hz, 1H), 7.53 (dd, J=7.5, 1.3 Hz, 1H), 7.50 (t, J=8.2 Hz, 1H), 7.40 (td, J=7.5, 1.3 Hz, 1H), 7.26 (dd, J=7.5 Hz, 1.3 Hz, 1H), 7.05 (d, J=8.2 Hz, 2H), 7.02 (d, J=8.2 Hz, 2H), 6.72-6.74 (m, 2H), 6.68-6.65 (m, 2H), 4.85 (d, J=14.5 Hz, 1H), 4.85 (d, J=14.5 Hz, 1H), 4.67 (d, J=14.5 Hz, 1H), 4.43 (d, J=14.5 Hz, 1H), 3.79 (s, 3H), 3.73 (s, 3H), 1.34 (s, 9H)

$^{13}$C-NMR (CDCl$_3$): δ=165, 159, 154, 154, 149, 141, 138, 136, 135, 135, 132, 131, 131, 130, 130, 129, 129, 128, 128, 125, 123, 114, 81, 55, 53, 53, 51, 28

MS: m/z=651 (MH$^+$)

Step 3

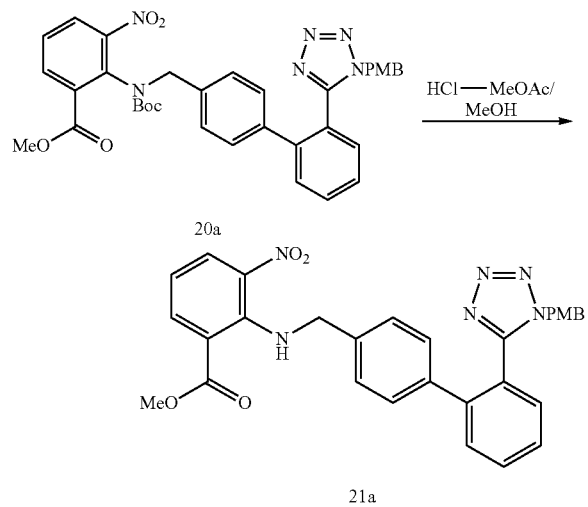

To hydrogen chloride-methanol (30%; 26.9 g, net 8.08 g, 222 mmol) was added methyl 2-(N-tert-butoxycarbonyl-N-{(2'-[1-(p-methoxybenzyl)-1H-tetrazol-5-yl]biphenyl-4-yl)methyl}amino)-3-nitrobenzoate (compound 20a, 5.00 g, 7.68 mmol) over 13 min by four portions at 4-5° C. The mixture was stirred at about 3° C. for 2 hr, and warmed to 9° C. over 1 hr. The reaction was monitored by TLC (eluent: toluene/ethyl acetate (2:1)). The reaction mixture was cooled to 3° C., and saturated aqueous sodium hydrogen carbonate solution (180 mL) was added dropwise thereto at 30° C. or lower. The mixture was extracted twice with ethyl acetate (450 mL, 250 mL), and the combined organic layers were washed with saturated brine (200 mL), dried over magnesium sulfate (10 g), and concentrated under reduced pressure at 40° C. or lower. To the concentrate was added chloroform, and the solvent was evaporated under reduced pressure in a bath at 40° C. to give methyl 2-[({2'-[1-(p-methoxybenzyl)-1H-tetrazol-5-yl]biphenyl-4-yl}methyl)amino]-3-nitrobenzoate (compound 21a, 4.27 g, 101%) as a yellowish brown amorphous solid.

IR: 1701, 1610, 1508, 1345 cm$^{-1}$ $^1$H-NMR (CDCl$_3$): δ=8.85 (br s, 1H), 8.12 (dd, J=8.0, 1.8 Hz, 1H), 7.98 (dd, J=8.0, 1.8 Hz, 1H), 7.65 (td, J=7.8, 1.2 Hz, 1H), 7.58 (dd, J=7.8, 1.2 Hz, 1H), 7.45 (td, J=7.8, 1.2 Hz, 1H), 7.36 (dd, J=7.8, 1.2 Hz, 1H), 7.19 (d, J=8.2, 1.2 Hz, 2H), 7.10 (d, J=8.2 Hz, 2H), 6.74 (t, J=8.0 Hz, 1H), 6.67 (d, J=9.0 Hz, 2H), 6.72 (d, J=9.0 Hz, 2H), 4.68 (s, 2H), 4.20 (d, J=5.0 Hz, 2H), 3.90 (s, 3H), 3.72 (s, 3H)

$^{13}$C-NMR (CDCl$_3$): δ=168, 160, 154, 145, 141, 138, 138, 137, 132, 131, 130, 130, 129, 128, 128, 125, 123, 117, 115, 114, 56, 52, 50, 50

MS: m/z=551 (MH$^+$)

Step 4

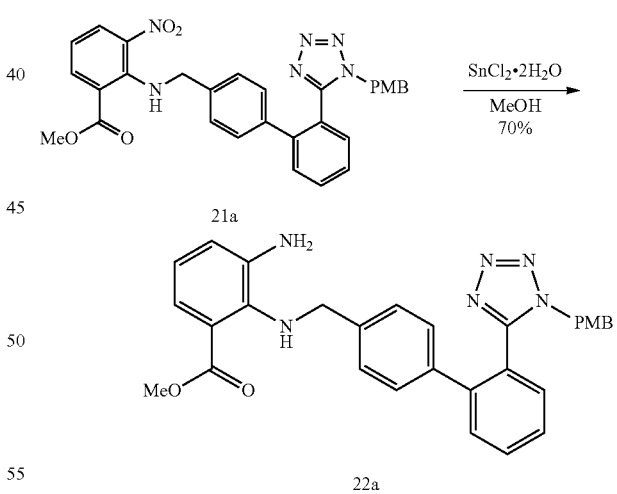

A mixture of methyl 2-[({2'-[1-(p-methoxybenzyl)-1H-tetrazol-5-yl]biphenyl-4-yl}methyl)amino]-3-nitrobenzoate (compound 21a, 2.73 g, 4.96 mmol) and tin(II) chloride dihydrate (4.48 g, 19.9 mmol) in methanol (60 mL) was heated under reflux for 2 hr. The reaction mixture was concentrated under reduced pressure, and to the concentrated residue were added saturated aqueous sodium hydrogen carbonate and ethyl acetate. The mixture was stirred for 1 hr, and filtered, and the insoluble material was washed with ethyl acetate. The filtrate and washing were combined, and concentrated under reduced pressure. The concentrated solution was extracted with ethyl acetate. The ethyl acetate solution of the resultant product was dried magnesium sulfate, and filtered. The filtrate was concentrated under reduced pressure, and the concentrated residue was purified by silica gel column (hexane→hexane:AcOEt=4:1→2:1→3:2) to give methyl 2-[({2'-[1-(p-methoxybenzyl)-1H-tetrazol-5-yl]biphenyl-4-yl}methyl)amino]-3-aminobenzoate (compound 22a) (1.96 g, 70%) as a brown amorphous solid.

IR: 1693, 1514, 1468, 1251 cm$^{-1}$ $^1$H-NMR (CDCl$_3$): δ=7.57-7.65 (m, 2H), 7.36-7.41 (m, 3H), 7.24-7.26 (m, 3H), 7.06-7.08 (m, 2H), 6.86-6.88 (m, 2H), 6.58-6.72 (m, 5H), 4.62 (s, 2H), 4.19 (s, 2H), 3.80 (s, 3H), 3.72 (s, 3H).

MS: m/z=521 (MH$^+$)

Step 5

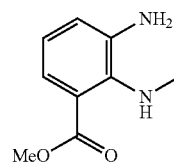

22a

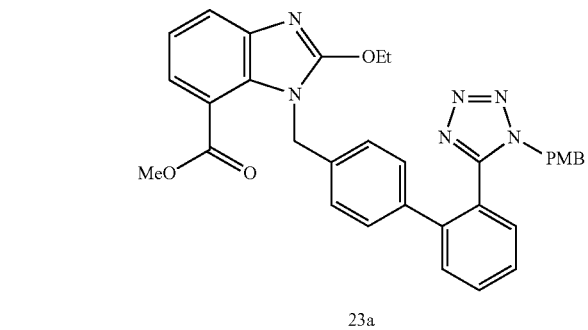

23a

A mixture of methyl 2-[({2'-[1-(p-methoxybenzyl)-1H-tetrazol-5-yl]biphenyl-4-yl}methyl)amino]-3-aminobenzoate (compound 22a, 1.76 g, 3.39 mmol), tetraethoxymethane (1 mL, 4.8 mmol) and acetic acid (2 ml) was stirred at 90° C. for 1 hr. The reaction mixture was cooled, ice and saturated aqueous sodium hydrogen carbonate were added thereto, and the mixture was extracted with chloroform. The extract was dried over magnesium sulfate, and filtered, and the filtrate was concentrated under reduced pressure. The concentrated residue was purified by silica gel column (hexane→hexane:AcOEt=5:1→4:1→3:1→2:1→1:1) to give the objective compound (compound 23a) (1.62 g, 83%) as a brown amorphous solid.

IR: 1716, 1549 cm$^{-1}$ $^1$H-NMR (CDCl$_3$): δ=7.73-7.74 (m, 1H), 7.15-7.56 (m, 6H), 6.99 (d, J=8 Hz, 2H), 6.89 (d, J=8 Hz, 2H), 6.60-6.66 (m, 4H), 5.59 (s, 2H), 4.68 (q, J=4 Hz, 2H), 4.59 (s, 2H), 3.75 (s, 3H), 3.68 (s, 3H), 1.49 (t, J=4 Hz, 3H).

MS: m/z=575 (MH$^+$)

Step 6

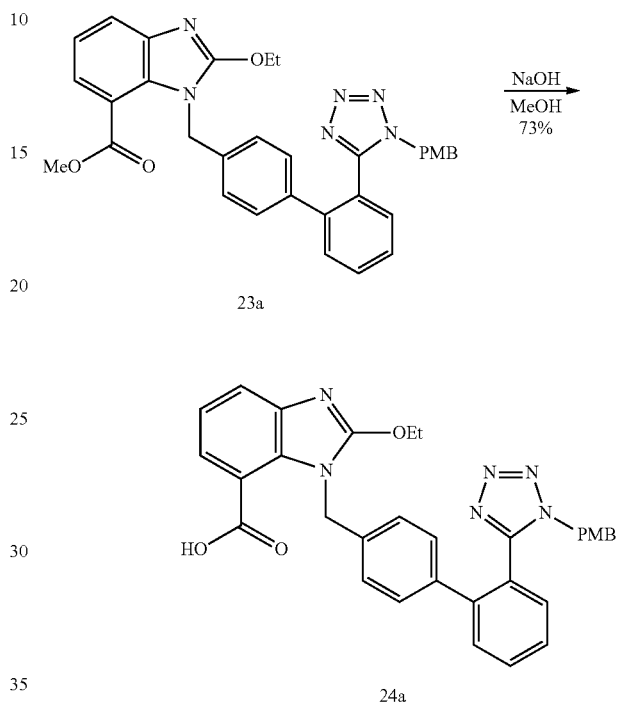

A mixture of the methyl ester form (compound 23a, 1.41 g, 2.45 mmol), 1N sodium hydroxide (15 mL) and methanol (7.5 mL) was stirred for 2 hr at 90° C. The methanol was evaporated under reduced pressure, and 10% hydrochloric acid was added thereto. The resultant product was extracted with a mixture of chloroform and THF. The extract was dried over magnesium sulfate, and filtered, and the filtrate was concentrated under reduced pressure. The concentrated residue was purified by silica gel column (CHCl$_3$→MeOH/CHCl$_3$ 2%→5%). The fractions of the objective compound were collected, and concentrated under reduced pressure. The concentrated residue was crystallized from a mixture of chloroform and diisopropyl ether, and the obtained crystal was washed with diisopropyl ether, and dried to give the objective compound (compound 24a) (1 g, 73%) as a colorless solid.

melting point: 196-198° C.

IR: 1690, 1551, 1465 cm$^{-1}$ $^1$H-NMR (DMSO-d$_5$): δ=7.65-7.72 (m, 2H), 7.49-7.60 (m, 5H), 7.16-7.20 (m, 1H), 6.85-6.90 (m, 4H), 6.71-6.75 (m, $H), 5.59% (s, 2H), 4.89 (s, 2H), 4.58 (q, J=8 Hz, 2H), 3.65 (s, 3H), 1.37 (t, J=8 Hz, 3H).

MS: m/z=561 (NH$^+$)

elemental analysis: Calcd for C$_{31}$H$_{26}$N$_6$O$_3$.0.1iPr$_2$O: C, 68.38; H, 5.21; N, 14.68%. Found: C, 68.10; H, 5.15; N, 14.68%.

Step 7

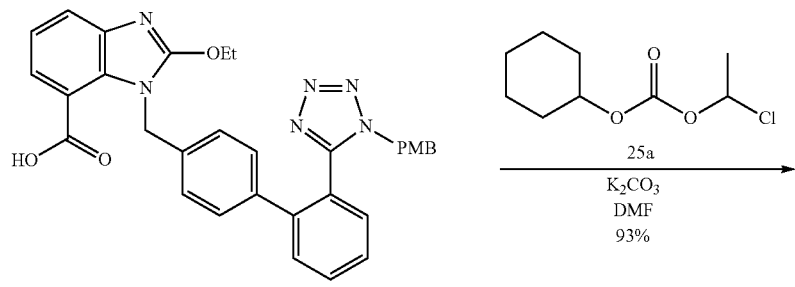

A mixture of the carboxylic acid form (compound 24a, 804 mg, 1.4 mmol), 1-chloroethylcyclohexyl carbonate (compound 25a, 346 mg, 1.7 mmol), potassium carbonate (309 mg, 2.2 mmol) and DMF (5 ml) was stirred at 65° C. for 4 hr. Water was added to the reaction mixture, and the resultant product was extracted with ethyl acetate. The extract was washed with water, dried over magnesium sulfate, and filtered. The filtrate was concentrated under reduced pressure, and the residue was purified by silica gel column (hexane→hexane:AcOEt=4:1→2:1→3:2→1:1) to give the objective compound (compound 26a) (972 mg, 93%) as a colorless amorphous solid.

IR: 1751, 1550, 1462 cm$^{-1}$ $^1$H-NMR (CDCl$_3$): δ=7.74-7.76 (m, 1H), 7.59-7.62 (m, 2H), 7.49-7.51 (m, 1H), 7.38-7.40 (m, 1H), 7.31-7.33 (m, 1H), 7.16-7.20 (m, 1H), 7.01 (d, J=8 Hz, 2H), 6.96 (d, J=8 Hz, 2H), 6.87-6.89 (m, 1H), 6.62-6.68 (m, 4H), 5.56-5.68 (m, 2H), 4.60-4.69 (m, 6H), 3.70 (s, 3H), 1.91-1.93 (m, 2H), 1.71-1.73 (m, 2H), 1.15-1.63 (m, 13H).

MS: m/z=731 (MH$^+$)

Step 8

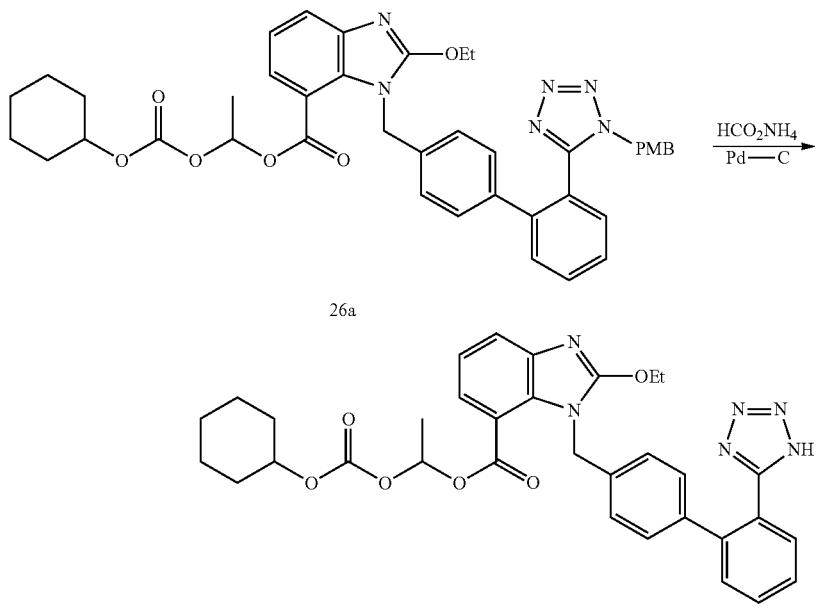

A mixture of the protected form by p-methoxybenzyl (compound 26a, 80.2 mg, 0.11 mmol), isopropanol (0.45 mL), water (0.3 mL), ammonium formate (36 mg, 0.57 mmol), palladium carbon catalyst (17 mg, 0.0033 mmol, Evonik, NN/W 5% Pd, water content 56%) was stirred at 40° C.-50° C. for 4 hr. Palladium carbon catalyst (13.5 mg, 0.0028 mmol, Evonik, NN/W 5% Pd, water content 56%) was added thereto, and the mixture was stirred at 50° C. for 1 hr. Then, palladium carbon catalyst (13.8 mg, 0.0029 mmol, Evonik, NN/W 5% Pd, water content 56%) was added thereto, and the mixture was stirred at 50° C. for 12 hr. After completion of the reaction, to the reaction mixture was added ethyl acetate, and the mixture was filtered. The filtrate was quantified by HPLC, and the content of the objective compound (compound 27, candesartan) was 36.8 mg (yield 55%).

Example 32

Step 1

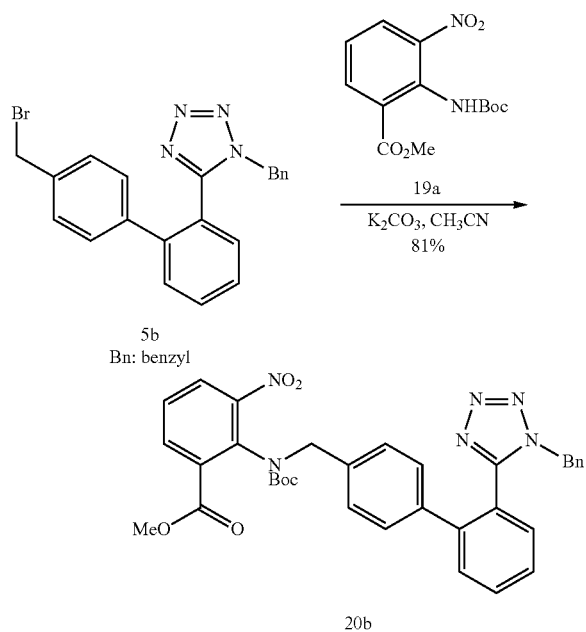

A mixture of 1-benzyl-5-[4'-(bromomethyl)biphenyl-2-yl]-1H-tetrazole (compound 5b, 9.82 g, 24 mmol), methyl 2-(tert-butoxycarbonylamino)-3-nitrobenzoate (compound 19a, 7.32 g, 24.7 mmol) and potassium carbonate (3.68 g, 26.7 mmol) in acetonitrile (100 mL) was heated under reflux for 6 hr under argon stream. To the reaction mixture was added potassium carbonate (1.34 g), and the mixture was heated under reflux for 3 hr. The reaction mixture was cooled and filtered. The insoluble material was washed with chloroform. The filtrate and washing were combined, and concentrated under reduced pressure. The concentrated residue was purified by silica gel column (hexane→hexane:AcOEt=5:1→4:1→3:1→2:1→3:2) to give methyl 2-(N-tert-butoxycarbonyl-N-{(2'-[1-benzyl-1H-tetrazol-5-yl]biphenyl-4-yl)methyl}amino)-3-nitrobenzoate (compound 20b) (12.17 g, 81%) as a yellow amorphous solid.

IR: 1710 cm$^{-1}$.

$^1$H-NMR (CDCl$_3$): δ=8.05-8.11, 7.88-7.90 (m, 2H), 7.60-7.61 (m, 1H), 7.50-7.52 (m. 1H), 7.05-7.26 (m, 10H), 6.78-6.80 (m, 2H), 4.85-4.94, 4.72-4.75 (m, 4H), 3.79 (s, 3H), 1.34 (s, 9H).

MS: m/z=621 (MH$^+$)

Step 2

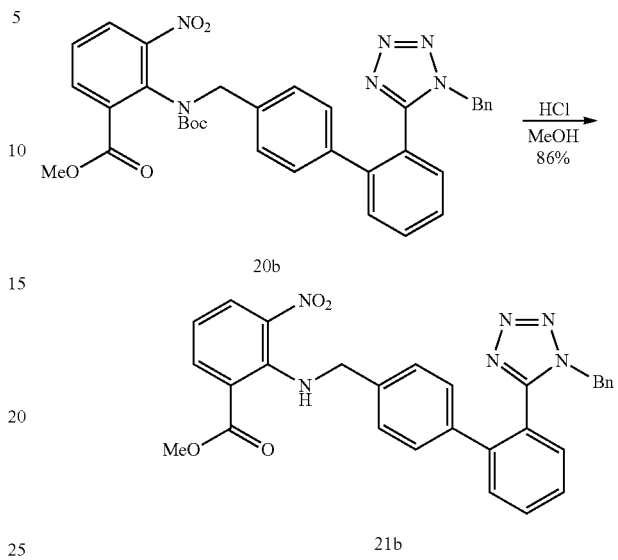

To a solution of methyl 2-(N-tert-butoxycarbonyl-N-{(2'-[1-benzyl-1H-tetrazol-5-yl]biphenyl-4-yl)methyl}amino)-3-nitrobenzoate (compound 20b, 11.93 g, 19.2 mmol) in methanol (15 mL) was added 2NHCl-MeOH (30 mL) under ice-cooling, and the mixture was stirred at the same temperature for 2 hr, and then overnight at room temperature. The reaction mixture was concentrated under reduced pressure, and to the residue were added methanol and diisopropyl ether. The resulting crystals were collected by filtration, washed with diisopropyl ether and hexane, and dried under reduced pressure to give methyl 2-[({2'-[1-benzyl-1H-tetrazol-5-yl]biphenyl-4-yl}methyl)amino]-3-nitrobenzoate (compound 21b) (8.64 g, 86%) as yellow crystals.

melting point: 115-117° C.

IR: 1696, 1530, 1451, 1256 cm$^{-1}$.

$^1$H-NMR (CDCl$_3$): δ=8.59-8.62 (m, 1H), 8.05-8.08 (m, 2H), 7.94-7.96 (m, 2H), 7.73-7.75 (m, 1H), 7.52-7.62 (m, 3H), 7.17-7.26 (m, 4H), 6.94-6.96 (m, 2H), 6.80-6.83 (m, 3H).

MS: m/z=521 (MH$^+$)

elemental analysis: Calcd for C$_{29}$H$_{24}$N$_6$O$_4$: C, 6691; H, 9.65; N: 16.14%. Found: C, 66.75; H, 4.66; N, 16.19%.

Step 3

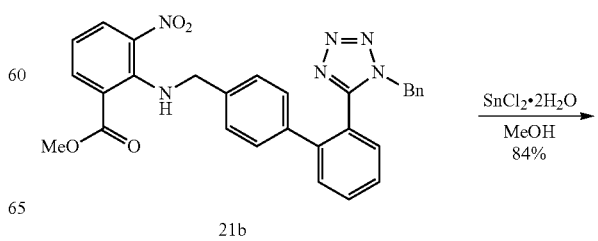

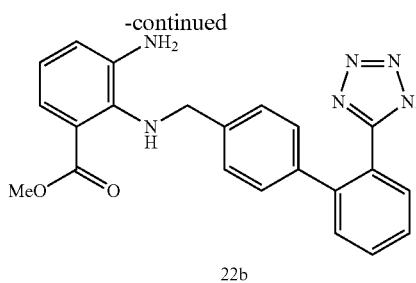

22b

A mixture of methyl 2-[({2'-[1-benzyl-1H-tetrazol-5-yl]biphenyl-4-yl}methyl)amino]-3-nitrobenzoate (compound 21b, 8.396 g) and tin (II) chloride dihydrate (13.56 g) in methanol (155 mL) was heated under reflux for 2 hr. The reaction mixture was concentrated under reduced pressure, and to the concentrated residue were added saturated aqueous sodium hydrogen carbonate and ethyl acetate. The mixture was stirred for 1 hr, and filtered, and the insoluble material was washed with ethyl acetate. The filtrate and washing were combined, and concentrated under reduced pressure, and the concentrated solution was extracted with ethyl acetate. The ethyl acetate solution of the resultant product was dried over magnesium sulfate, and filtered. The filtrate was concentrated under reduced pressure, and the concentrated residue was purified by silica gel column (hexane→thexane:AcOEt=5:1→4:1→3:1→2:1→3:2) to give methyl 2-[({2'-[1-benzyl-1H-tetrazol-5-yl]biphenyl-4-yl}methyl)amino]-3-aminobenzoate (compound 22b) (6.68 g, 84%) as a brown amorphous solid.

IR: 1692, 1468 cm$^{-1}$.

$^1$H-NMR (CDCl$_3$): δ=7.56-7.64 (m, 2H), 7.05-7.43 (m, 10H), 6.86-6.90 (m, 2H), 6.74-6.76 (m, 2H), 4.68 (s, 2H), 4.16 (s, 2H), 3.80 (s, 3H).

MS: m/z=491 (MH$^+$)

Step 4

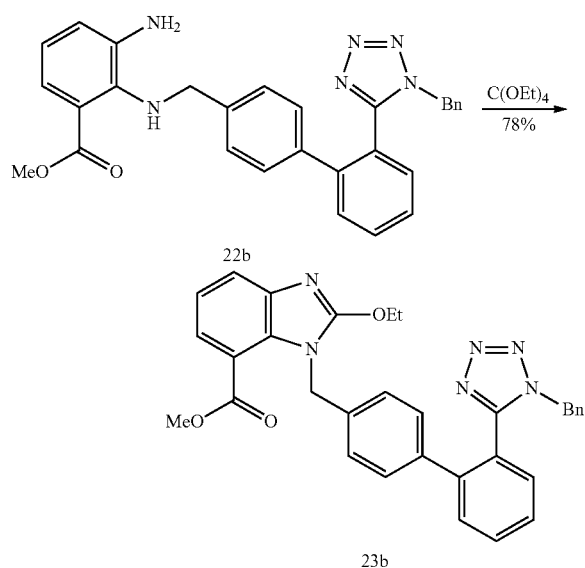

A mixture of methyl 2-[({2'-[1-benzyl-1H-tetrazol-5-yl]biphenyl-4-yl}methyl)amino]-3-aminobenzoate (compound 22b, 6.46 g, 13 mmol), tetraethoxymethane (3.6 mL, 17 mmol) and acetic acid (8 mL) was stirred at 90° C. for 1 hr. The reaction mixture was cooled, ice and saturated aqueous sodium hydrogen carbonate were added thereto, and the mixture was extracted with chloroform. The extract was dried over magnesium sulfate, and filtered, and the filtrate was concentrated under reduced pressure. The concentrated residue was purified by silica gel column (hexane→hexane:AcOEt=5:1→4:1→3:1→2:1→1:1) to give the objective compound (compound 23b) (5.61 g, 78%) as a brown amorphous solid.

IR: 1715, 1548 cm$^{-1}$ $^1$H-NMR (CDCl$_3$): δ=7.72-7.74 (m, 1H), 7.10-7.62 (m, 9H), 6.99 (d, J=8 Hz, 2H), 6.90 (d, J=8 HZ, 2H), 6.70-6.72 (m, 2H), 5.59 (s, 2H), 4.70 (q, J=4 Hz, 2H), 4.65 (s, 2H), 3.76 (s, 3H), 1.50 (t, J=4 Hz, 3H).

MS: m/z=545 (MH$^+$)

Step 5

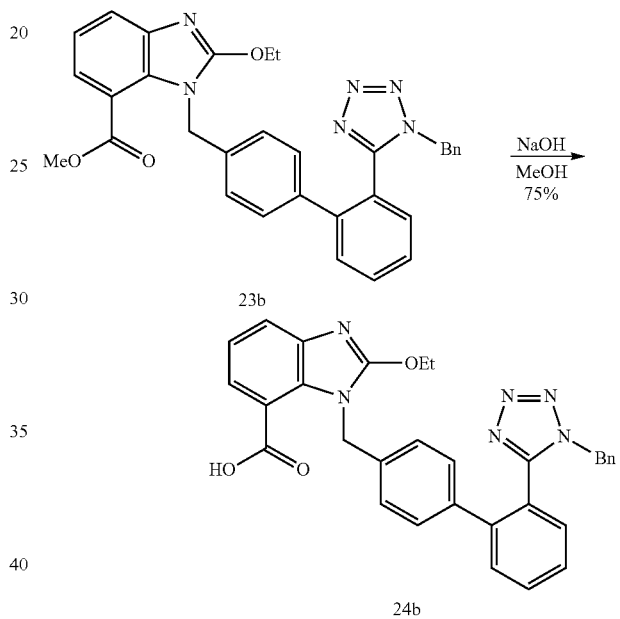

A mixture of methyl ester form (compound 23b, 5.4 g, 9.9 mmol), 1N sodium hydroxide (30 mL) and methanol (15 mL) was stirred at 90° C. for 2 hr. The methanol was evaporated under reduced pressure, 10% hydrochloric acid was added to the residue, and the resultant product was extracted with a mixture of chloroform and THF. The extract was dried over magnesium sulfate, and filtered, and the filtrate was concentrated under reduced pressure. The concentrated residue was purified by silica gel column (MeOH/CHCl$_3$ 2%→4%). The fractions of the objective compound were collected, and concentrated under reduced pressure. To the concentrated residue was added a mixture of chloroform and diisopropyl ether. The resulting crystals were washed with diisopropyl ether, and dried to give the objective compound (compound 24b) (3.96 g, 75%) as a colorless solid.

melting point: 171-173° C.

IR: 1696, 1530, 1451, 1256 cm$^{-1}$ $^1$H-NMR (DMSO-d$_6$): δ=7.65-7.72 (m, 2H), 7.49-7.56 (m, 4H), 7.15-7.23 (m, 4H), 6.86-6.90 (m, 4H), 6.75-6.77 (m, 2H), 5.59 (s, 2H), 4.97 (s, 2H), 4.59 (q, J=8 Hz, 2H), 1.37 (t, J=8 Hz, 3H).

MS: m/z=531 (MH$^+$)

elemental analysis: Calcd for C$_{31}$H$_{26}$N$_6$O$_3$·0.1H$_2$O: C, 69.94; H, 4.96; N, 15.79%. Found: C, 69.83; H, 4.96; N, 15.73%.

Step 6

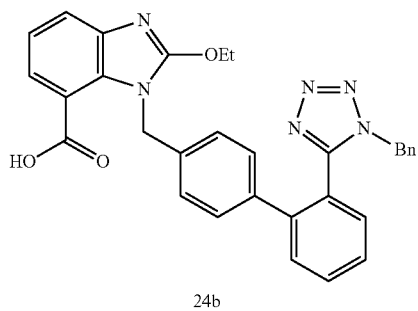

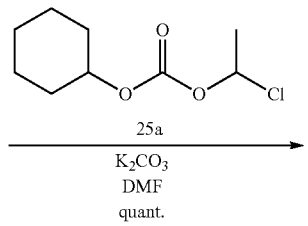

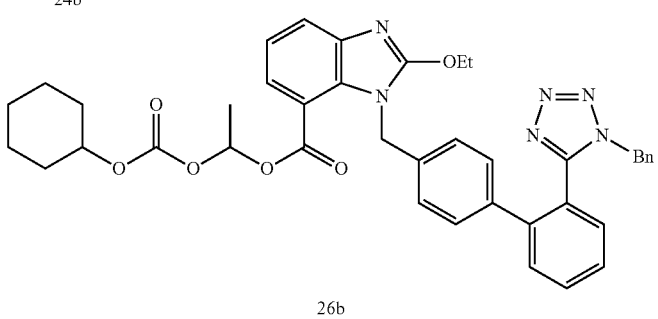

A mixture of the carboxylic acid form (compound 24b, 3.71 g, 6.99 mmol), 1-chloroethylcyclohexyl carbonate (compound 25a, 1.73 g), potassium carbonate (1.54 g) and DMF (20 mL) was stirred at 65° C. for 4 hr. Water was added to the reaction solution, and the resultant product was extracted with ethyl acetate. The extract was washed with water, dried over magnesium sulfate, and filtered. The filtrate was concentrated under reduced pressure, and the concentrated residue was purified by silica gel column (hexane→hexane:AcOEt=4:1→2:1→3:2→4:1) to give the objective compound (compound 26b) (4.9 g, quantitative) as a yellow amorphous solid.

IR: 1751, 1549, 1458 cm$^{-1}$ $^1$H-NMR (CDCl$_3$): δ=7.74-7.76 (m, 1H), 7.57-7.61 (m, 2H), 7.48-7.50 (m, 1H), 7.30-7.40 (m, 2H), 7.13-7.18 (m, 3H), 6.87-7.02 (m, 5H), 6.70-6.72 (m, 2H), 5.56-5.67 (m, 2H), 4.61-4.71 (m, 6H), 1.85-1.93 (m, 2H), 1.65-1.80 (m, 2H), 1.20-1.62 (m, 13H).

MS: m/z=701 (MH$^+$)

INDUSTRIAL APPLICABILITY

According to the present invention, an economical metal compound can be used and a biaryltetrazole derivative useful as an intermediate for an angiotensin II receptor antagonist can be produced under economical conditions suitable for industrial production.

This application is based on patent application Nos. 2009-262149 and 2010-143845 filed in Japan, the contents of which are encompassed in full herein.

The invention claimed is:

1. A production method of a biaryltetrazole derivative represented by the formula [I]:

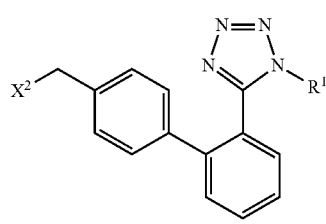

wherein $X^2$ is a halogen atom, and $R^1$ is a tetrazolyl-protecting group selected from a $C_{7-19}$ aralkyl group, a substituted $C_{7-19}$ aralkyl group and a trialkylsilyl group, or a salt thereof, which comprises 1) reacting an aryltetrazole derivative represented by the formula [II]:

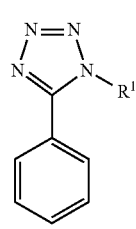

wherein $R^1$ is as defined above with a benzene derivative represented by the formula [III]:

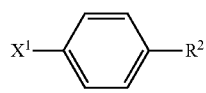

wherein R² is a methyl group, a methyl group substituted by hydroxyl group(s) protected by a protecting group, or a lower alkoxycarbonyl group, and X¹ is a leaving group selected from a halogen atom, a $C_{6-10}$ arylsulfonyloxy group optionally substituted by 1 to 3 $C_{1-6}$ alkyl groups and a $C_{1-6}$ alkylsulfonyloxy group optionally substituted by 1 to 3 halogen atoms in the presence of a ruthenium catalyst, a ligand and a base;

2) in the obtained compound represented by the formula [IV]:

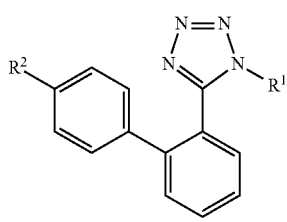

[IV]

wherein the symbols are as defined above,
(a) deprotecting the compound wherein R² is a methyl group substituted by hydroxyl group(s) protected by a protecting group, or
(b) reducing the compound wherein R² is a lower alkoxycarbonyl group, to give a compound represented by the formula [V]:

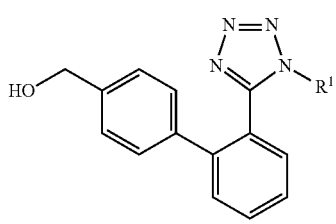

[V]

wherein the symbol is as defined above; and 3) halogenating
the compound represented by the formula [IV] wherein R² is a methyl group, or
the compound represented by the formula [V] when R² in the compound represented by the formula [IV] is a methyl group substituted by hydroxyl group(s) protected by a protecting group, or a lower alkoxycarbonyl group.

2. A production method of a compound represented by the formula [IX]:

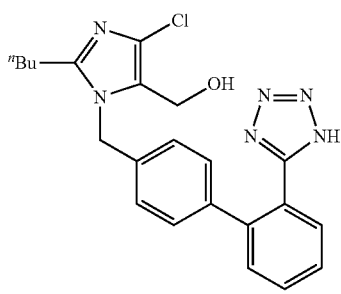

[IX]

or a salt thereof, which comprises
1) reacting a biaryltetrazole derivative represented by the formula [I]:

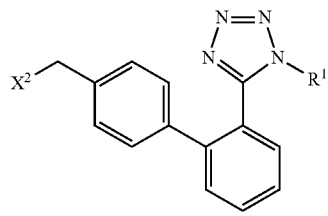

[I]

wherein X² is a halogen atom, and R¹ is a tetrazolyl-protecting group selected from a $C_{7-19}$ aralkyl group, a substituted $C_{7-19}$ aralkyl group and a trialkylsilyl group, or a salt thereof, which is obtained by the production method of claim 1, with a compound represented by the formula [VI]:

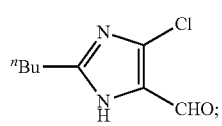

[VI]

and
2-A) reducing the obtained compound represented by the formula [VII]:

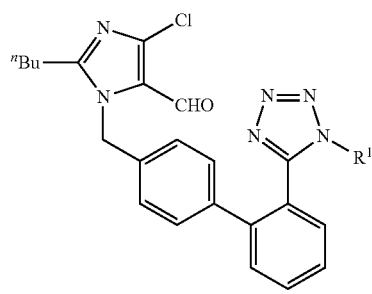

[VII]

wherein the symbol is as defined above to give a compound represented by the formula [VIII]:

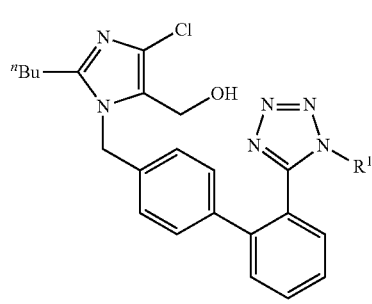

[VIII]

wherein the symbol is as defined above, and
removing R¹ from the compound represented by the formula [VIII]; or
2-B) removing R¹ from the compound represented by the formula [VII] to give a compound represented by the formula [VIII-2]:

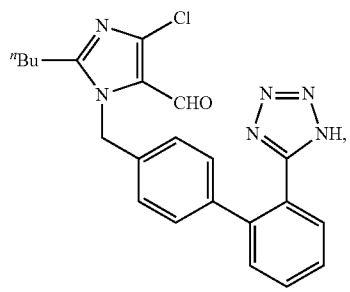
[VIII-2]

and
reducing the compound represented by the formula [VIII-2].

3. A production method of a compound represented by the formula [XV]:

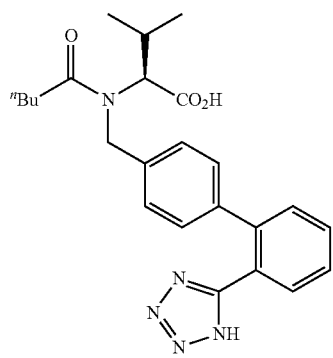
[XV]

or a salt thereof, which comprises
1) reacting a biaryltetrazole derivative represented by the formula [I]:

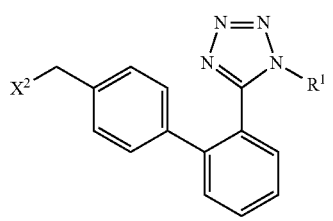
[I]

wherein $X^2$ is a halogen atom, and $R^1$ is a tetrazolyl-protecting group selected from a $C_{7-19}$ aralkyl group, a substituted $C_{7-19}$ aralkyl group and a trialkylsilyl group, or a salt thereof, which is obtained by the production method of claim 1, with a compound represented by the formula [X]:

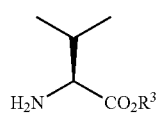
[X]

wherein $R^3$ is a carboxy-protecting group or a salt thereof;

2-A) removing $R^1$ from the obtained compound represented by the formula [XI]:

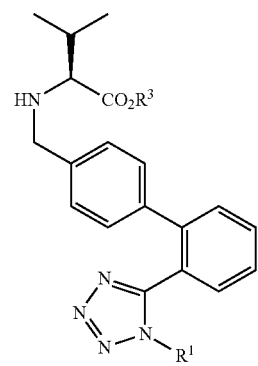
[XI]

wherein the symbols are as defined above,
reacting the obtained compound represented by the formula [XII]:

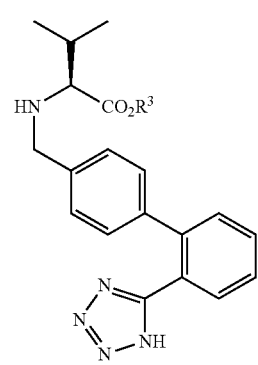
[XII]

wherein the symbol is as defined above with a compound represented by the formula [XIII]:

$CH_3CH_2CH_2CH_2CO—X^3$ wherein $X^3$ is a leaving group, and
removing $R^3$ from the obtained compound represented by the formula [XIV]:

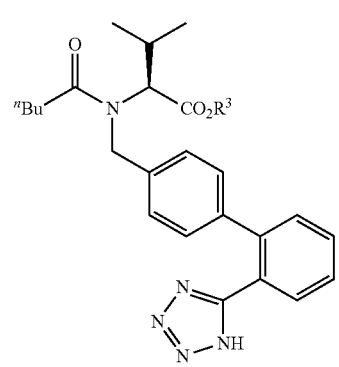
[XIV]

wherein the symbol is as defined above; or
2-B) reacting the compound represented by the formula [XI] with the compound represented by the formula

[XIII], and removing $R^1$ and $R^3$ from the obtained compound represented by the formula [XII-2]:

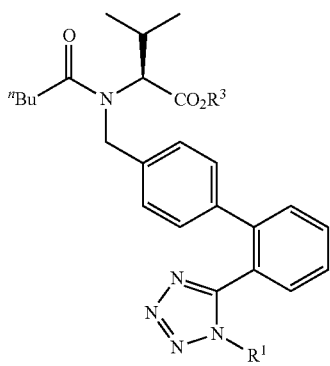

[XII-2]

wherein the symbols are as defined above.

4. A production method of a compound represented by the formula [XVIII]:

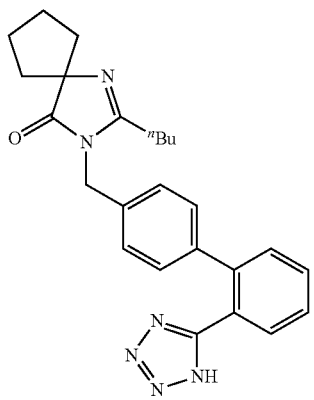

[XVIII]

or a salt thereof, which comprises reacting a biaryltetrazole derivative represented by the formula [I]:

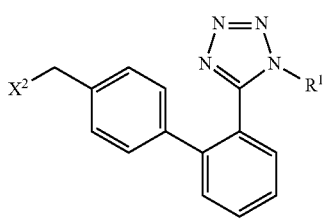

[I]

wherein $X^2$ is a halogen atom, and $R^1$ is a tetrazolyl-protecting group selected from a $C_{7-19}$ aralkyl group, a substituted $C_{7-19}$ aralkyl group and a trialkylsilyl group, or a salt thereof, which is obtained by the production method of claim 1, with a compound represented by the formula [XVI]:

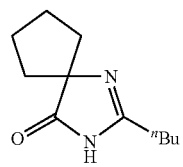

[XVI]

or a salt thereof to give a compound represented by the formula [XVII]:

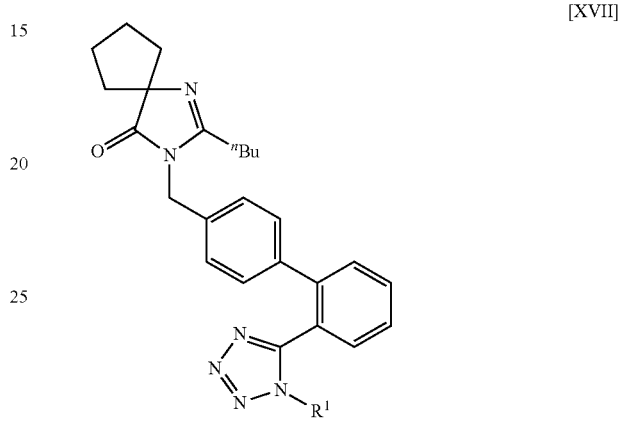

[XVII]

wherein the symbol is as defined above, and
removing $R^1$ from the compound represented by the formula [XVII].

5. A production method of a compound represented by the formula [XXVII]:

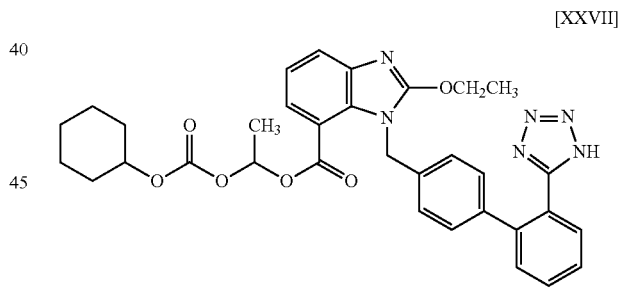

[XXVII]

or a salt thereof, which comprises
1) reacting a biaryltetrazole derivative represented by the formula [I]:

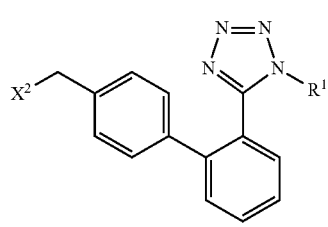

[I]

wherein $X^2$ is a halogen atom, and $R^1$ is a tetrazolyl-protecting group selected from a $C_{7-19}$ aralkyl group, a substituted $C_{7-19}$ aralkyl group and a trialkylsilyl group, or a salt thereof, which is obtained by the production method of claim 1, with a compound represented by the formula [XIX]:

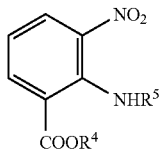

[XIX]

wherein $R^4$ is a carboxy-protecting group, and $R^5$ is an amino-protecting group, 2) removing $R^5$ from the obtained compound represented by the formula [XX]:

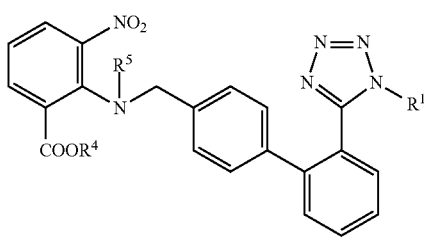

[XX]

wherein the symbols are as defined above to give a compound represented by the formula [XXI]:

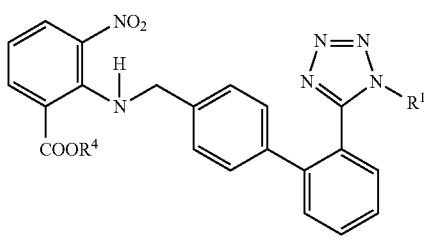

[XXI]

wherein the symbols are as defined above, and reducing the compound represented by the formula [XXI], 3) reacting the obtained compound represented by the formula [XXII]:

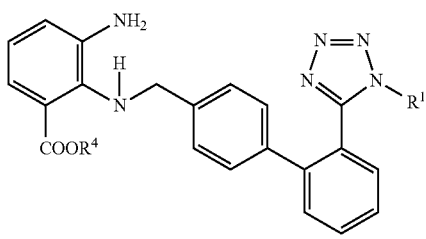

[XXII]

wherein the symbols are as defined above with tetraethoxymethane to give a compound represented by the formula [XXIII]:

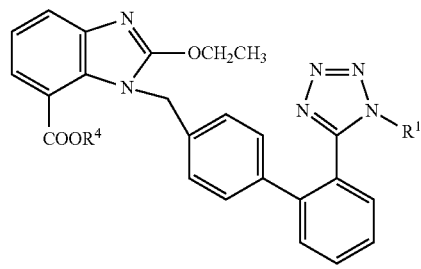

[XXIII]

wherein the symbols are as defined above, and removing $R^4$ from the compound represented by the formula [XXIII], and 4) reacting the obtained compound represented by the formula [XXIV]:

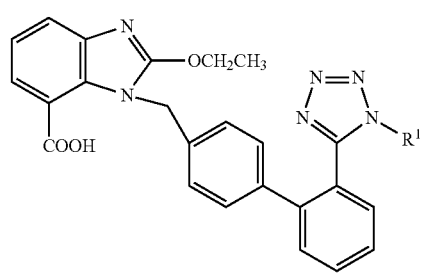

[XXIV]

wherein the symbol is as defined above with a compound represented by the formula [XXV]:

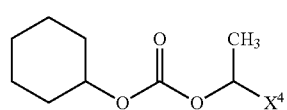

[XXV]

wherein $X^4$ is a leaving group or a hydroxyl group to give a compound represented by the formula [XXVI]:

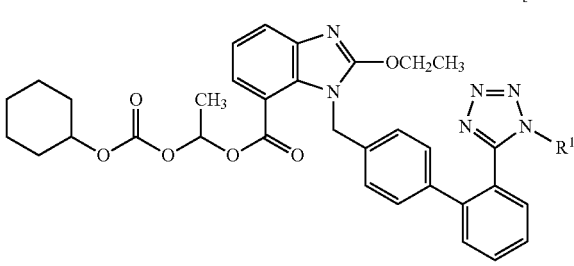

[XXVI]

wherein the symbol is as defined above, and removing $R^1$ from the compound represented by the formula [XXVI].

* * * * *